(12) United States Patent
Shen et al.

(10) Patent No.: US 11,154,040 B2
(45) Date of Patent: Oct. 26, 2021

(54) GENETICALLY MODIFIED NON-HUMAN ANIMAL WITH HUMAN OR CHIMERIC CD137

(71) Applicant: Biocytogen Pharmaceuticals (Beijing) Co., Ltd., Beijing (CN)

(72) Inventors: Yuelei Shen, Beijing (CN); Yanan Guo, Beijing (CN); Yang Bai, Beijing (CN); Lei Zhao, Beijing (CN); Rui Huang, Beijing (CN); Jiawei Yao, Beijing (CN); Meiling Zhang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/434,456

(22) Filed: Jun. 7, 2019

(65) Prior Publication Data

US 2019/0343095 A1 Nov. 14, 2019

Related U.S. Application Data

(63) Continuation of application No. PCT/CN2017/120388, filed on Dec. 30, 2017.

(30) Foreign Application Priority Data

| Dec. 30, 2016 | (CN) | .......................... 201611256707.4 |
| Sep. 25, 2017 | (CN) | .......................... 201710873061.2 |
| Dec. 29, 2017 | (CN) | .......................... 20171147325.1 |

(51) Int. Cl.
| *A01K 67/027* | (2006.01) |
| *A61K 49/00* | (2006.01) |
| *C07K 14/705* | (2006.01) |
| *C12N 15/85* | (2006.01) |

(52) U.S. Cl.
CPC ...... *A01K 67/0278* (2013.01); *A61K 49/0008* (2013.01); *C07K 14/70578* (2013.01); *C12N 15/8509* (2013.01); *A01K 2217/072* (2013.01); *A01K 2227/105* (2013.01); *A01K 2267/0331* (2013.01); *C12N 2015/8572* (2013.01)

(58) Field of Classification Search
CPC ............ A01K 67/0278; A01K 2207/15; A01K 2227/105
USPC ........................................................ 800/21
See application file for complete search history.

(56) References Cited

U.S. PATENT DOCUMENTS

| 4,683,195 A | 11/1987 | Mullis et al. |
| 7,138,500 B1 | 11/2006 | Goodwin et al. |
| 2015/0106961 A1 | 4/2015 | Rojas et al. |

FOREIGN PATENT DOCUMENTS

| CN | 104561095 | 4/2015 | | |
| WO | WO-2004039840 A1 * | 5/2004 | .............. | A61P 29/00 |
| WO | WO 2006088447 | 8/2006 | | |
| WO | WO-2009091826 A2 * | 7/2009 | ....... | C07K 14/70521 |
| WO | WO 2014165452 | 10/2014 | | |
| WO | WO 2015091653 | 6/2015 | | |
| WO | WO 2018001241 | 1/2018 | | |
| WO | WO 2018041118 | 3/2018 | | |
| WO | WO 2018041119 | 3/2018 | | |
| WO | WO 2018041120 | 3/2018 | | |
| WO | WO 2018041121 | 3/2018 | | |
| WO | WO 2018068756 | 4/2018 | | |
| WO | WO 2018086583 | 5/2018 | | |
| WO | WO 2018086594 | 5/2018 | | |
| WO | WO 2018113774 | 6/2018 | | |

OTHER PUBLICATIONS

Maksimenko et al., 2013 (Acta Naturae, vol. 5, No. 1, p. 33-46).*
Sanmamed (2016, Annals of Oncology, 27:1190-1198).*
Lute (Blood. Nov. 1, 2005; 106(9): 3127-3133).*
Chester (2016, Cancer Immunol Immunother, 64:1423-1248).*
Genbank Accession No. NP_001552, May 6, 2012, https://www.ncbi.nlm.nih.gov/protein/5730095?sat=15&satkey=7727244, accessed Dec. 17, 2019).*
Alderson (1994, Eur J Immunol, 24:2219-2227).*
Guest (2005, Journal of Immunotherapy, 28:203-211).*
Hemmi (1994, PNAS, 89:2737-2741).*
Gordley (2016, Curr Opin Struct Biol, 39:106-114).*
Dombrowicz (1996, J Immunol, 157:1645-1651).*
Auerbach et al., "Establishment and Chimera Analysis of 129/SvEv- and C57BL/6-Derived Mouse Embryonic Stem Cell Lines," BioTechniques, 2000, 29:1024-1032.
Broll et al., "11CD137 expression in tumor vessel walls: high correlation with malignant tumors," American journal of clinical pathology, 2001, 115(4):543-549.
Testing et al., "Revised nomenclature for strain 129 mice," Mammalian Genome, 1999, 10:836, 1 page.
International Search Report and Written Opinion in International Appln. No. PCT/CN2017/120388, dated Apr. 8, 2018, 11 pages.
Ito et al., "NOD/SCID/ ycnull mouse: an excellent recipient mouse model for engraftment of human cells," Blood, 2002, 100(9):3175-3182.
Kohrt et al., "Stimulation of natural killer cells with a CD137-specific antibody enhances trastuzu efficacy in xenotransplant models of breast cancer," The Journal of Clinical Investigation, 2012, 122(3):1066-1075.
Palazon et al., "Agonist anti-CD137 mAb act on tumor endothelial cells to enhance recruitment of activated T lymphcytes," Cancer research, 2011, 71(3):801-811.
Wen et al., "4-1BB ligand-mediated costimulation of human T cells induces CD4 and CD8 T cell expansion, cytokine production, and the development of cytolytic effector function," The Journal of Immunology, 2002, 165.10:4897-4906.

(Continued)

*Primary Examiner* — Valarie E Bertoglio
(74) *Attorney, Agent, or Firm* — Fish & Richardson P.C.

(57) ABSTRACT

The present disclosure relates to genetically modified non-human animals that express a human or chimeric (e.g., humanized) CD137, and methods of use thereof.

11 Claims, 22 Drawing Sheets

Specification includes a Sequence Listing.

(56) References Cited

OTHER PUBLICATIONS

Yin et al., "Delivery technologies for genome editing," Nature Reviews Drug Discovery, 2017, 16(6):387-399.
GenBank Accession No. KJ891470.1, "Synthetic construct *Homo sapiens* clone ccsbBroadEn_00864 TNFRSF9 gene, encodes complete protein," GenBank, May 28, 2014, 3 pages.
GenBank Accession No. XM011250228.2, "Predicted: Mus musculus tumor necrosis factor receptor superfamily, member 9 (Tnfrsf9), transcript variant X1, mRNA," GenBank, Jun. 22, 2016, 4 pages.
Baessler, et al., "CD137 ligand mediates opposite effects in human and mouse NK cells and impairs NK-cell reactivity against human acute myeloid leukemia cells," Blood, 2010, 115(15):3058-3069.
Yi et al., "Human and mouse CD137 have predominantly different binding CRDs to their respective ligands," PloS one, 2014, 9(1):e86337.
Zhu et al., "Humanising the mouse genome piece by piece," Nature communications, 2019, 10(1):1-13.
Baessler et al., "CD 137 ligand mediates opposite effects in human and mouse NK cells and impairs NK-cell reactivity against human acute myeloid leukemia cells," Blood, The Journal of the American Society of Hematology, Apr. 15, 2010, 115(15): 13 pages.
PCT International Preliminary Report on Patentability in International Appln. PCT/CN2017/120388, dated Jul. 2, 2019, 6 pages.
Scheer et al., "In vivo responses of the human and murine pregnane X receptor to dexamethasone in mice," Drug metabolism and disposition, Jul. 1, 2010, 38(7):1046-1053.
Yi et al., "Human and mouse CD137 have predominantly different binding CRDs to their respective ligands," PloS one, Jan. 21, 2014, 9(1):e86337, 10 pages.
Zhu et al., "Humanising the mouse genome piece by piece," Nature communications, Apr. 23, 2019, 10(1):1-13.

\* cited by examiner

| Score | Expect | Method | Identities | Positives | Gaps |
|---|---|---|---|---|---|
| 266 bits(681) | 9e-95 | Compositional matrix adjust. | 148/254(58%) | 179/254(70%) | 6/254(2%) |

```
Mouse   1    MGNNCYNVVIVLLLVGCEKVGAVQNSCDNCQPGTFC-RKYNPVCKSCPPSTFSSIGGQP    59
             MGN+CYN+V  +LL++   E+  ++Q+ C NC  GTFC   N +C  CPP++FSS GGQ
Human   1    MGNSCYNIVATLLLVLNFERTRSLQDPCSNCPAGTFCDNNRNQICSPCPPNSFSSAGGQR   60

Mouse   60   NCNICRVCAGYFREKKFCSSTHNAECECIEGFHCLGPQCTRCEKDCRPGQELTKQGCKTC   119
             C+ICR C G  FR +K CSST NAEC+C   GFHCLG  C+ CE+DC+ GQELTK+GCK C
Human   61   TCDICRQCKGVFRTRKECSSTSNAECDCTPGFHCLGAGCSMCEQDCKQGQELTKKGCKDC   120

Mouse   120  SLGTENDQNGTGVCRPWTNCSLDGRSVLKTGTTEKDVVCGPPVVSFSPSTTISVTPEGGP   179
                GTENDQ      G+CRPWTNCSLDG+SVL  GT E+DVVCGP    SP + SVTP
Human   121  CFGTFNDQK-RGICRPWTNCSLDGKSVLVNGTKERDVVCGPSPADLSPGAS-SVTPPAPA   178

Mouse   180  G---GHSLQVLTLFLALTS-ALLLALIFITLLFSVLKWIRKKFPHIFKQPFKKTTGAAQEE   236
                GHS Q+++ FLALTS ALL L E+TL FSV+K  RKK   +IFKQPF +        QEE
Human   179  REPGHSPQIISFFLALTSTALLFLLFFLTLRFSVVKRGRKKLLYIFKQPFMRPVQTTQEE   238

Mouse   237  DACSCRCPQEEEGG   250
             D CSCR P+EEEGG
Human   239  DGCSCRFPEEEEGG   252
```

FIG. 23

SEQUENCE LISTING

<160> NUMBER OF SEQ ID NOS: 50

<210> SEQ ID NO 1
<211> LENGTH: 39
<212> TYPE: DNA
<213> ORGANISM: Artificial
<220> FEATURE:
<223> OTHER INFORMATION: PCR primer

<400> SEQUENCE: 1
cgatggtacc agtactgtgg aactgcttaa atatggttg                    39

<210> SEQ ID NO 2
<211> LENGTH: 46
<212> TYPE: DNA
<213> ORGANISM: Artificial
<220> FEATURE:
<223> OTHER INFORMATION: PCR primer

<400> SEQUENCE: 2
ctatgttgta acagctgttt cccatggcga aatgtcacat gcacag            46

<210> SEQ ID NO 3
<211> LENGTH: 46
<212> TYPE: DNA
<213> ORGANISM: Artificial
<220> FEATURE:
<223> OTHER INFORMATION: PCR primer

<400> SEQUENCE: 3
ctgtgcatgt gacatttcgc catgggaaac agctgttaca acatag            46

<210> SEQ ID NO 4
<211> LENGTH: 40
<212> TYPE: DNA
<213> ORGANISM: Artificial
<220> FEATURE:
<223> OTHER INFORMATION: PCR primer

<400> SEQUENCE: 4
agcggtggct cacacctgta tactcgctgc tatgccccca                   40

<210> SEQ ID NO 5
<211> LENGTH: 40
<212> TYPE: DNA
<213> ORGANISM: Artificial
<220> FEATURE:
<223> OTHER INFORMATION: PCR primer

<400> SEQUENCE: 5
tgggggcata gcagcgagta tacaggtgtg agccaccgct        40

<210> SEQ ID NO 6
<211> LENGTH: 45
<212> TYPE: DNA
<213> ORGANISM: Artificial
<220> FEATURE:
<223> OTHER INFORMATION: PCR primer

<400> SEQUENCE: 6
aggaacaagg taaggacctg caaagagtgt cctgcaaaac acagc        45

<210> SEQ ID NO 7
<211> LENGTH: 45
<212> TYPE: DNA
<213> ORGANISM: Artificial
<220> FEATURE:
<223> OTHER INFORMATION: PCR primer

<400> SEQUENCE: 7
gctgtgtttt gcaggacact ctttgcaggt ccttaccttg ttcct        45

<210> SEQ ID NO 8
<211> LENGTH: 32
<212> TYPE: DNA
<213> ORGANISM: Artificial
<220> FEATURE:
<223> OTHER INFORMATION: PCR primer

<400> SEQUENCE: 8
cgatctcgag caatatcctt gtgggagcaa gc        32

<210> SEQ ID NO 9
<211> LENGTH: 39
<212> TYPE: DNA
<213> ORGANISM: Artificial
<220> FEATURE:
<223> OTHER INFORMATION: PCR primer

<400> SEQUENCE: 9
cgatggatcc aggcctgcaa tgcctggagg cagttgtat        39

<210> SEQ ID NO 10
<211> LENGTH: 37
<212> TYPE: DNA
<213> ORGANISM: Artificial
<220> FEATURE:
<223> OTHER INFORMATION: PCR primer

<400> SEQUENCE: 10
cgatgcggcc gcagtactag gctggggcct agcaaac        37

<210> SEQ ID NO 11
<211> LENGTH: 44
<212> TYPE: DNA
<213> ORGANISM: Artificial
<220> FEATURE:
<223> OTHER INFORMATION: PCR primer

<400> SEQUENCE: 11
gctggtaccg gcgcgcctcg aggtcagaat cccaaggaca gcag    44

<210> SEQ ID NO 12
<211> LENGTH: 37
<212> TYPE: DNA
<213> ORGANISM: Artificial
<220> FEATURE:
<223> OTHER INFORMATION: PCR primer

<400> SEQUENCE: 12
gaggggttct tagatatccc gtgctgttta tccactc    37

<210> SEQ ID NO 13
<211> LENGTH: 35
<212> TYPE: DNA
<213> ORGANISM: Artificial
<220> FEATURE:
<223> OTHER INFORMATION: PCR primer

<400> SEQUENCE: 13
acagcacggg atatctaaga acccctccct acgtc    35

<210> SEQ ID NO 14
<211> LENGTH: 48
<212> TYPE: DNA
<213> ORGANISM: Artificial
<220> FEATURE:
<223> OTHER INFORMATION: PCR primer

<400> SEQUENCE: 14
tcctcttcag acctggcggc cgcgtcctct actctctacc cagttttg    48

<210> SEQ ID NO 15
<211> LENGTH: 2134
<212> TYPE: DNA
<213> ORGANISM: Mus musculus

<400> SEQUENCE: 15
ttcctgaaat tcaggtgctg caggcagccc tcagcacaga gagctgacag ggaccctggg    60
tcaggggttc tgagttccag ctgccactat tcttcttcac ctttggtgtc ctgtgcatgt    120
gacatttcgc catgggaaac aactgttaca acgtggtggt cattgtgctg ctgctagtgg    180
gctgtgagaa ggtgggagcc gtgcagaact cctgtgataa ctgtcagcct ggtactttct    240
gcagaaaata caatccagtc tgcaagagct gccctccaag taccttctcc agcataggtg    300 acagccgaa ctgtaacatc tgcagagtgt gtgcaggcta tttcaggttc aagaagtttt    360
gctcctctac ccacaacgcg gagtgtgagt gcattgaagg attccattgc ttggggccac    420
agtgcaccag atgtgaaaag gactgcaggc ctggccagga gctaacgaag cagggttgca    480
aaacctgtag cttgggaaca tttaatgacc agaacggtac tggcgtctgt cgaccctgga    540
cgaactgctc tctagacgga aggtctgtgc ttaagaccgg gaccacggag aaggacgtgg    600
tgtgtggacc ccctgtggtg agcttctctc ccagtaccac catttctgtg actccagagg    660
gaggaccagg agggcactcc ttgcaggtcc ttaccttgtt cctggcgctg acatcggctt    720
tgctgctggc cctgatcttc attactctcc tgttctctgt gctcaaatgg atcaggaaaa    780 aattcccca catattcaag caaccattta agaagaccac tggagcagct caagaggaag    840
atgcttgtag ctgccgatgt ccacaggaag aagaaggagg aggaggaggc tatgagctgt    900

-continued

```
gatgtactat cctaggagat gtgtgggccg aaaccgagaa gcactaggac cccaccatcc      960
tgtggaacag cacaagcaac cccaccaccc tgttcttaca catcatccta gatgatgtgt     1020
gggcgcgcac ctcatccaag tctcttctaa cgctaacata tttgtcttta cctttttaa      1080 atctttttt aaatttaaat tttatgtgtg tgagtgtttt gcctgcctgt atgcacacgt      1140
gtgtgtgtgt gtgtgtgtga cactcctgat gcctgaggag gtcagaagag aaagggttgg    1200
ttccataaga actggagtta tggatggctg tgagcctttg tgtgggtgct aggaatcaaa    1260
cctgggtcct ctacaagggc agccagtgct cttaaccact gagtcagctt tccagccctg    1320
ccctggacag ttttaaaat ttaacttaat ttttttttt ttttacttaa gcccttaaca      1380
tttttaatag gactgtggga agatcaattt ctagattctc cttaacaata tacatcatat    1440
acatatacac atacatatac atatacatat atattctgag aaaatgacag tttcagttgg    1500
atctcataga ccaatggtcc agttaaaata actgtaaaat cagtgtgtgt gtgtgtgtgt    1560
gtgtgtgtgt gcaaatatga tgcatgacaa tagccataag atgcagtata ttaccctatc    1620 ccatttcct ttggttctc actcactata ataacacctc cactgtctga agggggagac      1680
ccatgcatcc ctgtctggag gaagcctgac agattttgag gggaatcttc agagcagttc    1740
aagggcctgc ttctcctgtt tcctctgtgt caggcttttc aataaaaagg ccgtttagga    1800
aagggacaaa gcactgtgag gtggggaaca cctgtgaact cacagtagga acgcggcctt    1860
ccagtccacc atgggcagac atggctgccg cttgcctctg catgactcct ggacagctca    1920
agagctgaga atggttgtta cttttcttta ttttgagaca gcacctcct ctgtagtgct     1980 ggctggcctg gaagtcacag aaatcctcct gcctctgctt ccagagtact gggtcttaaa    2040
ctgttcacca cgtctcccct ccccaacccc caaactagcc tttccatttt taaaagccag    2100
ctaaaaatat taagttgtg ctcttacaaa agtc                                 2134
```

<210> SEQ ID NO 16
<211> LENGTH: 256
<212> TYPE: PRT
<213> ORGANISM: Mus musculus

<400> SEQUENCE: 16

```
Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160
```

```
Pro Val Val Ser Phe Ser Pro Ser Thr Thr Ile Ser Val Thr Pro Glu
            165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
            195                 200                 205

Ser Val Leu Lys Trp Ile Arg Lys Lys Phe Pro His Ile Phe Lys Gln
            210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 17
<211> LENGTH: 6001
<212> TYPE: DNA
<213> ORGANISM: Homo sapiens

<400> SEQUENCE: 17
caaggaggga tcccacagat gtcacagggc tgtcacagag ctgtggtggg aatttcccat    60
gagaccccgc ccctggctga gtcaccgcac tcctgtgttt gacctgaagt cctctcgagc   120
tgcagaagcc tgaagaccaa ggagtggaaa gttctccggc agccctgaga tctcaagagt   180
gacatttgtg agaccagcta atttgattaa aattctcttg gaatcagctt tgctagtatc   240
atacctgtgc cagatttcat catgggaaac agctgttaca acatagtagc cactctgttg   300
ctggtcctca actttgagag gacaagatca ttgcaggatc cttgtagtaa ctgcccagct   360
ggtacattct gtgataataa caggaatcag atttgcagtc cctgtcctcc aaatagtttc   420
tccagcgcag gtggacaaag gacctgtgac atatgcaggc agtgtaaagg tgttttcagg   480
accaggaagg agtgttcctc caccagcaat gcagagtgtg actgcactcc agggtttcac   540
tgcctggggg caggatgcag catgtgtgaa caggattgta acaaggtcag aactgaca    600 aaaaaaggtt gtaaagactg ttgctttggg acatttaacg atcagaaacg tggcatctgt   660
cgaccctgga caaactgttc tttggatgga agtctgtgc ttgtgaatgg gacgaaggag    720
agggacgtgg tctgtggacc atctccagcc gacctctctc cgggagcatc ctctgtgacc   780
ccgcctgccc ctgcgagaga gccaggacac tctccgcaga tcatctcctt ctttcttgcg   840
ctgacgtcga ctgcgttgct cttcctgctg ttcttcctca cgctccgttt ctctgttgtt   900
aaacggggca gaaagaaact cctgtatata ttcaaacaac catttatgag accagtacaa   960
actactcaag aggaagatgg ctgtagctgc cgatttccag aagaagaaga aggaggatgt  1020
gaactgtgaa atggaagtca atagggctgt tgggactttc ttgaaaagaa gcaaggaaat  1080
atgagtcatc cgctatcaca gctttcaaaa gcaagaacac catcctacat aatacccagg  1140 attccccaa cacacgttct tttctaaatg ccaatgagtt ggcctttaaa aatgcaccac    1200
tttttttttt tttttgacag ggtctcactc tgtcacccag gctggagtgc agtggcacca  1260
ccatggctct ctgcagcctt gacctctggg agctcaagtg atcctcctgc ctcagtctcc  1320
tgagtagctg gaactacaag gaaggccac acacctgac taacttttt gttttttgtt     1380 tggtaaagat ggcatttcac catgttgtac aggctggtct caaactccta ggttcacttt  1440
ggcctcccaa agtgctggga ttacagacat gaactgccag gccggccaa ataatgcac    1500 cactttttaac agaacagaca gatgaggaca gagctggtga taaaaaaaaa aaaaaaaaag  1560
```

```
cattttctag ataccactta acaggtttga gctagttttt ttgaaatcca agaaaatta      1620
tagtttaaat tcaattacat agtccagtgg tccaactata attataatca aaatcaatgc      1680
aggtttgttt tttggtgcta atatgacata tgacaataag ccacgaggtg cagtaagtac      1740
ccgactaaag tttccgtggg ttctgtcatg taacacgaca tgctccaccg tcagggggga      1800
gtatgagcag agtgcctgag tttagggtca aggacaaaaa acctcaggcc tggaggaagt      1860
tttggaaaga gttcaagtgt ctgtatatcc tatggtcttc tccatcctca cacttctgc       1920
cttgtcctg ctccctttta agccaggtta cattctaaaa attcttaact tttaacataa       1980
tattttatac caaagccaat aaatgaactg catatgatag gtatgaagta cagtgagaaa      2040
attaacaccct gtgagctcat tgtcctacca cagcactaga gtgggggccg ccaaactccc     2100
atggccaaac ctggtgcacc atttgccttt gtttgtctgt tggtttgctt gagacagtct      2160
tgctctgttg cccaggctgg aatggagtgg ctattcacag gcacaatcat agcacacttt      2220
agccttaaac tcctgggctc aagtgatcca cccgcctcag tctcccaagt agctgggatt      2280
acaggtgcaa acctggcatg cctgccattg tttggcttat gatctaagga tagctttttta   2340
aattttattc atttttatttt ttttttgagac agtgtctcac tctgtctccc aggctggagt    2400
acagtggtac aatcttggat caccgcctcc cagtttcaag tgatctccct gcctcagcct     2460
cctaagtagc tgggactaca ggtatgtgcc accacgcctg gctaatttt atattttag        2520
tagagacggg gtttcaccat gttgtccagg ctggtctcaa actcctgacc tcaggtgatc      2580
tgcccacctc tgcctcccaa agtgctggga ttacaggcat gagccaccat gcctggccat      2640
ttcttacact tttgtatgac atgcctattg caagcttgcg tgcctctgtc ccatgttatt      2700
ttactctggg atttaggtgg agggagcagc ttctatttgg aacattggcc atcgcatggc     2760
aaatgggtat ctgtcacttc tgctcctatt tagttggttc tactataacc tttagagcaa      2820
atcctgcagc caagccaggc atcaataggg cagaaaagta tattctgtaa ataggggtga     2880
ggagaagata tttctgaaca atagtctact gcagtaccaa attgcttttc aaagtggctg     2940
ttctaatgta ctcccgtcag tcatataagt gtcatgtaag tatcccattg atccacatcc     3000
ttgctaccct ctggtactat caggtgccct taattttgcc aagccagtgg gtatagaatg     3060
agatctcact gtggtcttag tttgcatttg cttggttact gatgagcacc ttgtcaaata     3120
tttatatacc atttgtgttt attttttttaa ataaaatgct tgctcatgct tttttgccca    3180
tttgcaaaaa aacttggggc cgggtgcagt ggctcatgcc tgtagtccca gctctttggg    3240
aggccaaggt gggcagatcg cttgagccca ggagttcgag accagccttg caacatggc      3300
gaaaccctgt ctttacaaaa aatacaaaaa ttagccgggt gtggtggtgt gcacctgaag     3360
tcccagctac tcagtaggtt cgctttgagc ctgggaggca gaggttgcag tgagctggga    3420
ccgcatcact acacttcagc ctgggcaaca gagaaaaacc ttttctcaga acaaacaaa     3480
cccaaatgtg gttgttttgtc ctgattccta aaaggtcttt atgtattcta gataataatc     3540
tttggtcagt tatatgtgtt aaaaaatatc ttctttgtgg ccaggcacgg tagctcacac      3600
ctgtaatccc agcactttgc ggggctgagg tgggtggatc atctgaggtc aagagttcaa      3660
gatcagcctg gccaacacag tgaaacccca tctctactaa acatgtacaa aacttagctg     3720
ggtatggtgg cgggtgcctg taaccccagc tgctccagag gctgtggcag aagaatcgct     3780
tgaacccagg aggcagaggt tgcagcgagc caagattgtg ccattgcact ccagactggg    3840
tgacaagagt gaaattctgc ctatctatct atctatctat ctatatctat atatatatat      3900
atatatatcc tttgtaattt attttttccct ttttaaaatt ttttataaaa ttcttttta      3960
```

```
ttttattttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgtttttctc taattaatgg tgtctttctt tgtctttctg    4140
gtaataagca aaaagttctt catttgattt ggttaaattt ataactgttt tctcatatgg    4200
ttaacatttt ttcttgcctg gctaaagaaa tccttttctg cccaatacta taaagaggtt    4260
tgcccacatt ttattccaaa agttttaagt tttgtctttc atcttgaagt ctaatgtatc    4320
aggaactggc ttttgtgcct gttgggaggt agtgatccaa ttccatgtct gcatgtagg    4380 taaccactgg tccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttcttttt ctacttcaga    4620
agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
ccccatctct actaaaaaat acaaaaatta gtcaggcatg gtggcatgtg cctgtaatcc    4800
cagctatttg ggaggctgag gccggagaat tgcttgaacc cggggggcgg aggttgcagt    4860
gagccgagat cgtaccattg cactccagcc tgggtgacag agcgaaactc tgtctcagga    4920 aaaaaagaa aagagatgtc ttggttattc ttggttcttt attattcaat ataaatttta    4980
gaagctgaat ttgaaaagat ttggattgga atttcattaa atctacaggt caatttaggg    5040
agagttgata attttacaga attgagtcat ctggtgttcc aataagaata agagaacaat    5100
tattggctgt acaattcttg ccaaatagta ggcaaagcaa agcttaggaa gtatactggt    5160
gccatttcag gaacaaagct aggtgcgaat attttttgtct ttctgaatca tgatgctgta    5220
agttctaaag tgatttctcc tcttggcttt ggacacatgg tgtttaatta cctactgctg    5280
actatccaca aacagaaaga gactggtcat gccccacagg gttggggtat ccaagataat    5340
ggagcgaggc tctcatgtgt cctaggttac acaccgaaaa tccacagttt attctgtgaa    5400
gaaaggaggc tatgttatg atacagactg tgatatttt atcatagcct attctggtat    5460
catgtgcaaa agctataaat gaaaaacaca ggaacttggc atgtgagtca ttgctccccc    5520
taaatgacaa ttaataagga aggaacattg agacagaata aaatgatccc cttctgggtt    5580
taatttagaa agttccataa ttaggtttaa tagaaataaa tgtaaatttc tatgattaaa    5640
aataaattag cacatttagg gatacacaaa ttataaatca ttttctaaat gctaaaaaca    5700
agctcaggtt ttttcagaa gaaagtttta atttttttc tttagtggaa gatatcactc    5760
tgacggaaag ttttgatgtg aggggcggat gactataaag tgggcatctt cccccacagg    5820
aagatgtttc catctgtggg tgagaggtgc ccaccgcagc tagggcaggt tacatgtgcc    5880
ctgtgtgtgg taggacttgg agagtgatct ttatcaacgt ttttatttaa aagactatct    5940
aataaaacac aaaactatga tgttcacagg aaaaaaagaa taagaaaaaa agaaaaaaaa    6000
a                                                                   6001
```

<210> SEQ ID NO 18
<211> LENGTH: 255
<212> TYPE: PRT
<213> ORGANISM: Homo sapiens

<400> SEQUENCE: 18

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 19
<211> LENGTH: 4847
<212> TYPE: DNA
<213> ORGANISM: Mus musculus

<400> SEQUENCE: 19
gtcagaatcc caaggacagc agatcaaacc tctgtgactt accgtgacac cagcctccag      60
gacggccaac cactttttctt aagtggaaaa aaatcacaag tgttagtgtg tggggacctt    120
gaaacccttg tttgctacag atggagttgt gaattgatgt agctgcggtg ggaaacagtg    180
agctcaaagt gaaaccgagc tactacttgg cacaggagcc ccaccccttaa atgtacacca    240 aagagaacga ttcagttatg cacacacctg aatggcagca taaaagccat gagtggaacc    300
aattcagatg tccatgaact gctgagtgga taaacagcac gggatatctc tgtctaaagg    360
aatattacta caccaggaaa aggacacatt cgacaacagg aaaggagcct gtcacagaaa    420
accacaggtt ggctaattgt attttatgaa tgtgtagaag agacaagatc attctcaggg    480
agacacaaca tatgtgggat tggtcatgt tgtcccccaa cccgaccacc aaccccagac      540
agggtttctc tgtgttcctg gctgtcctgg aatttgctct gtagaccagg ctgtccttga    600
actcagaaat ctgcctgcct ctgcctcctg agttttggga ttagaagtgt gtgccgctgt    660
gcctggcttt agatattttt gttttaaaat atttcttaaa aagctaggct tgagctgggc    720

```
gtggtggcac acacctttaa tccctgcact cgggacgcag ggtcaggtgg gtttctgagt    780
tcgaggccag cctggtctac agagtgagtt ccaggacagc caggactaca cagagaaact    840
ctgtttcgaa aaaccaaaaa aaaaaaaaaa aaaagctagg cttggtagca catgccttta    900
atccaagcat tcaggaagca gaggcaggta caagtagatc tctggggctt tgagggcagc    960
ctggtcttca cagtgaactc acagctgagg cttcatactg agacactgtc tcaaaaatta   1020
aaaacaaaac aaaacaaaca aaccatgctt atgtgtgttc gcctgtgtat tacaccctat   1080
acatgcaatg ccggtgaagg ccagaagggg gcaccacatt ttctggatct agaggtttag   1140
gcagctgtga gcgggcctgt ggaatgctgg gagtcaaacc taagtcctcc actagaacag   1200
ccagtgctct tgatcacgga accaatccag gatttctttt tgattaatgg gagtgttctg   1260
taatcgactg gagaggacag tttcctgtat agtgaatagt ctagactctt ctgaatgatg   1320
tataactcag atgttgaagg gacctgagct gtgagttaca ggctgctgtg agccacttgg   1380
tatgcactgt gagttgaagc tgggtcctct gcaagggcag tatgtactct taaccacgga   1440
gccgtctctc aagccccttt tatttttaaa ttatgtgtat gttgggggta tgtgtgcatg   1500
aattcaggca tccaaaagag gacaccggat ctccctggac ttaaaggcgc ttgtcagctg   1560
cccagtgtga gtgctggaaa ctaaactgaa gttttctgca ggagcactaa gccaccataa   1620
ccacagagcc atctctccag cctctctatt gcatccttct acggtgagca gtgatgtgac   1680
tggcctcatg cagacccaga cagttttcag catgtgcgtt actaaagggc agctctcttc   1740
cggtctcccg tcttaccgtc caagagcaag cctccatttc tcttgtggaa gaacatttcc   1800
tagtcatttg aattccagtg ggaagtcgtc tatctatttt agataaaact gaccaagccg   1860
ggcagtggtg gcccacgact tggtggccca tgactaatcc cagcacttgg gaggcagggg   1920
caggcggatt tctgagctcg aggccagcct ggtctacaga gtgagttcca ggacagccag   1980
ggctacacag agaaaccctg tctcgaaaaa ccaaaaaaaa aaaaaaaaaa aaaaaaaaaa   2040
aaaaaaaaaa aaagaaaga agaaaagaa aaagaaaag aaaagacaag accgggtctc   2100
gttgcataac ccaggcagac ttggaacttg ggactcgtga tcctcctgct ccagccatac   2160
aagttctgga attacagctg tgtgtatgtc cacgccttct tgctatgacc tctccccagc   2220
tggccatctc ctgagcatct ttagtcacgt gtcatgctcg gtttccatag caaccgcgtc   2280
ctcctcttcc ctttccctcc tccctcccct cttctccttc cttcttcctt ccctcctcat   2340
ctccctcctc tgatcttcct caccctctcc tccctctttc tcctcttcca gttcttcttt   2400
ttttttccac tcaatttaac gtttctctaa aacttacaga tctccacctt gttcagcgac   2460
atcacctatc tcccgccctg cagttttttct tctccccaat ctctcacact cactcacaga   2520
catcacagaa catcctgccc tgctgtcctt tgcctagaca cacagccaga gccttctcac   2580
ttgcataagg gcaccctaat agtaatactg gtgagacaaa ttcctgggct tccagggttg   2640
gatggcactc tccacagtgc agctcagtac tgggtttaag aggtctctct gttcttacgg   2700
ttaggagatg atttgtgaca aaaccacttt gggtcggtct cagtccttaa gtcttcagta   2760
ttttaaggac acatgaaaag ttttgcatgg atgaaggact gtgataagcg accaagtctg   2820
tttcctaaag tcgtccagga aacgtcctaa tgggcaacag ctgattccaa gaaacccttc   2880
agagtggcat tgagtgggga ctgaagctct ggggattttg agggtagcga ggagacaaac   2940
cacctcacag agcagctggg gatttcccag gaggccctgc tcagttgagt cacaggtcct   3000
gtgtttgacc tgtggtcttg tggagcggca gaacctcacc gagctgccaa ggaagcagaa   3060
```

-continued

```
cgctcctcgc tgccctgaga tcgaaaggtt tgtctgctgg ggactagtgg gggactagag    3120
gagtgaggac ggactgtgtg ctccagtgca gatttctaga ctgttcttcc cttgtagttt    3180
ataatttcca tctcatagcc cacgacataa agattaaaaa atgaagttgg tccccccttt    3240 tcttttttc ttttcttga cacaggtct tgtgtagccc agtctagtct caaactctct    3300
gtatagcctg acactgaatt tctgactctc ctgcctccat ctcctgagtg ctaggattac    3360
tactgtacct gattgagtac ctgggttcca tgcatgctag gcaggtgctt caccgcctga    3420
gcttcagcac cagccttaga atttgttttt aattgccttt tttgtttgtt tacaatcctc    3480
aaatctcaaa attggcaagt acaggtctgt gcttaagaaa ccctgacagt gggctggaga    3540
gatggttcgg tggttaagag cactgactgc tcttccagag gtcctgagtt caaatcccag    3600
caaccacatg gtggctcaca actatctgta atgggatctg gtgccctctt ctggtgtgtc    3660
tgaagacagc tacagtgtac ttatatataa taaataaata agtctttttt aaaaaagaa    3720 aagaagaaa ctctgacagt aaattaacag gggtcttta aaatgagccc aattaaatgt    3780
tcagtaaaaa aaaaaaaaaa caaaaacagg gcgatagcca caggctctcc tttcattgag    3840 gggaccccctc agatggcact ggccatctgg actttgcttc aggggcagca tggctgcaat    3900
ctggatgcca acatggatac tctgaaagtt ctaatgcttc tgttctcatt gtccctgtgt    3960
ttgtgaagaa catgagattt caccccttggg ctttgcagat atgcgcaaag ccggtggctg    4020
ctgtagaact ctgaactttg tgcttccata gtatcccagt ttttcttaa aggactttaa    4080 aatgttaaat tgtctttgta tgtttggaca cttgagtgca gacagccgga ggcataggat    4140
cccctggagc tggagttata gacagttgtg agcctcccag tatggggttg ggaatcaaac    4200
ctgggtcctt tacaggagca acgtgtgctt tcaagcattg agccatctct ccagccccaa    4260
tatcccagtc ttaactgctc tttaaaacac tgtggaactg ggggctggag agatggctca    4320
gtggttaaga gcactgactg ttcttccata ggtcctgagt tcaattccca caactacat    4380 ggtggctcac aacctctgt aatgagatct gatgccctct tctgatgtgt ctgaagacag    4440
ctacagtgta ctcatataaa taaaacatat cttaaaaaat actgtggaac tgcttaaata    4500
tggttgatag tgtagacagt tcgggaaagg aaccccaccc cactatagt ttacagaatg    4560 acacttgtga gatatccccc tcttttagag acagggtttc atgtagctca ggttggcctg    4620
gaactttctc tgcagtcggg gatggccttg aactcttgct cctcccgctc ccatctcatg    4680
tgtgctgggg ttacagcatc cactaccact ccgggtatct gcacactggt tcctgtttag    4740
caagcatgct atcagtcaag caacagcagc agccagagga caactcatct gactgagaca    4800
ctttcggaat ctcctttgct agtgtcctgt gcatgtgaca tttcgcc              4847
```

<210> SEQ ID NO 20
<211> LENGTH: 4728
<212> TYPE: DNA
<213> ORGANISM: Mus musculus

<400> SEQUENCE: 20

```
gcaatgcctg gaggcagttg tatagcgaga cttttggttt ctttcttttt tttattaca     60 tattttcctc aattacattt ccaatgctat cccaaaagtc ccccataccc tcccctcac    120 tcccctaccc acccattccc acttttggc cctggcgttc ctctgtactg gggcatataa    180
agtttgcgtg tccaatgggc ctctcttccc agtgatggcc tacaaggcca tcttttgata    240
catttgcagc tagagtcaag agctccaggg tactggttag ttcatattgt tgttccacct    300
acagggttgc agatctcttt agctccttgg atactttttc tagctcctcc attgggggcc    360
```

```
ctgtgatcca tccaatagct gactgtgagc atccacttat gtgtttgcta ggccccagcc      420
tagtctcaca agagacaact atatcagggt cctttcagca aatgcttgct agtgtatgca      480
atggtgtcat cgtttggagg ctaattatgg gatggatccc tggacatggc agtctctaga      540
tggtccatcc ttttgtctca gctccaaact ttgtctctga acttttggt ttctttaaaa       600 acacaggaat attatgtgtt tttgtttaat tccaggtgtg ggatatgggg cagcttcaga      660
ctgtccgcaa cagctgtcta caatttgcct ctaacagggg catgattttg ccagctgcag      720
atggtttccg caagtgtgtg atatatggaa ttctggggac ttttcagagg ttatataaac      780
tatagagccc tgctagaagg ggtttgttaa gtagtagggt gtgaagagaa gaaattaggc      840
aaagatcata attgcaccaa gggacttgct accctagtc taatgatatc attgccctcc       900
ctcccatttt attctttttt ctctcttatc tggtgttagg ggcttggaag aagtgaaggg      960
gtggagaagg aaggaagaaa aaggacccac aaagtagcca agggtctggt gacacagttg      1020
gggtggttgt gacttggtgc tgggaggcat agctggagca agggctgagg aagctgttct      1080
atcccacagt gcagagtggc cactagggca gaaatgaaga cagaacagaa tctagggtac      1140
agataggaca tcagacacat atgccacagt cccagataac tgtgcacatg tgagtgtggg      1200
cacccagtca gcctgtgccc gtggcatgga agaaccggaa aagaacattg ttcagaagct      1260
gggggttgag gggggcatgg ctcagttggc caagtgtaga cacactaacg cccagatccg      1320
tgtaagaagc agtggcatgc tcccaacagt gcaggcagtg acaggcaggt ccctgggtcg      1380
cgctaaccag cctcacctag ttggtgaaat cagagctagt gagagaccct gactcaaaaa      1440 aaaaaaaaa aaaaaaagca agcaaacaaa ggtggacctc tgccctccaa cacacatgtg      1500
cacttgcaca catgtcaatg catgcacacc cctacaccc tatacagagc accaccctac       1560
tcacccagcc ttacctctct ggatggtaga tagcctcggc cttggctcag gtctacactt      1620
aagtagagag aactggaggg tgtggaagtg agtgtaggat ggactgctac ggtgtgaaca      1680
aacgctttca gaggtggatt tcacccactc ataagctaaa taagatgctg ttaagaatca      1740
agctagtgtc tggcactgag tcagtaccct acacaaaagc tttcagggtc tactcgcatt      1800
ttatggtcca agatggggca gcttgtgctc tgactttgtg aaagacagga tgagggcaca      1860
agatggtcag agataaagag catccagatg gcaaaattac agcttcaaat gagagcggac      1920
cgaagtgtcg aaattgatta aaatatttga ggagagctca gtaggttaag acacttgctg      1980
caaagcctga tgacctgagc tccaaccctg ggtagtagga gagagctgac tcccgcgggt      2040
tgtcatctgg cacgcaagca cacgcccgca catgcgcccg cacatgcgca caggcacaca      2100
agcgcactgt aaaagcctga ggctagaacc agagaggtgg tccagcaggg taagggtgct      2160
tgctgttcac tagtcagaga atcatctccc aagctttatt tgtgttttg tttgtttgtt        2220 tgtttgtttg tttgtttgtt ttttaacctg tggcggggg atgtgggaac aaggaactga       2280
ggtcgtgtcc aaggcagtag gtcaaacttt tccgaaatga tggggggggg acggggactg      2340
tactggatgc tcttcagag agcttcgagt tctccacttg ctccgcttcc gtgtgaacgg       2400
ggcagcgcta ttttttatctg tctggtgggt ggggaagagg agctcgttgt gttttgaatt     2460
tacatttcct tgatgatggt tgaagttagc tgccttttgc cttttacat ttgattggct       2520 gtttggattt cttacgctga gaagtcttcc tgccgggcca cctgcccttt ccttatcaat      2580
gaaggggaca ccgtgcatgt ccccagctgt agatgtctgt tccttttctt tggtcgttct     2640
ctctcctgcc caggcttctt tccggcgcag ccctctaaac taccaaaaaa atcctcatca     2700
```

```
caccccactc ccagagagcc aacaaggttt ctatgaacat gtcttcaaag gtattaatta      2760
gtaatgactg acctgcaatt ttataaaaag ctttaaaacc cttttagttt ttatataatt      2820
acacattcac agaaagtcac aaagagcagg atagcgtcac atggcatccg tgagaccta      2880
aggtcaccac gaggccagga caatgatggt gtgaacacac atagctgtca gtcacttcat      2940
tagctgtgta gattcatgta acataactga accaggcagc ttgtaaagtg gggcgtgggg      3000
tgcagatctg gagccccggc atgagagaga ctgaagcagg aggctcatgg ccctagatca      3060
caagactcaa caacaatcaa gcaaacaaaa tgcccccaga ctatccacaa gcaaggtctt      3120
ggcccccgct ggctctcctc agcccctact cctgtccccc tttctctggc agccccctca      3180
tctatttcc attttaactc ctagttgttt aaaaagtata tttattattt aatgtgttac       3240
aattaatttg ttacaaaaac aattgcatga gttttattgt ataaaatgca cgcagggaca      3300
tgtggaggcc agaccctctg gaactggact tacaggcagt gatatgtcac tgtgtggctc      3360
ctctgtgtgg gtgctgggaa ctgatctagg gtcctttgca ggagcagcga gtgctcaact      3420
actgagccag ctctccagcc ctgtgatatt ttactcttac atgtaaaaca atcaacccaa      3480
accaaacaaa aacaacaaca acccacccct aaatctatgg atgcttatgg gtaggtttca      3540
tgtgagggta agttttttgtg tctcttaaga taaatgcacc cagagagtca gatgtttctg      3600
agtttgcttt tgtttacttt gtgtgtgtgc tgagatcaga agaccacctg caaagggaga      3660
ttctctcctc cacttggctg agtctctctt gtatccacca agcaatgtag actagctagc      3720
actgagtctc catccccggc cccaccccca ttccccaccc ctgtctttgc ctctcatcca      3780
tcttgccata ggaatgctgg tctcaccact ggatttggct tcaaaatatt ttcttaatgg      3840
agctggagag atggctcctc tggctgagag cactgaccgt tcttccagag gtcctgagtt      3900
caattcccag ccaccacatg gtgtctgaca gccacctgta atgggatctt atgccctctt      3960
ctggtgtgta ggtgtacatg taaatagagc actgactttt ttttttttcct aaaggaaaaa      4020
tagttttatg tctctccctc cccgagagag agagagagag agagagagag agagagagag      4080
tgtggtggat gtatgagagg aggaggtgta atgaggcatg agtgcgtgcg tgtggggct       4140
atggatgtgt gtgcatggtg gaatgcatgt ggggcacgg gtgtgtgtgg gcagtcacat       4200
gcaagtgcat gtgtgtaggt cagaggagtc cccgtgggag taggtgctct ccttctacca     4260
catggttcac agggattaaa cgcaagcctt caagcttcag cagcaggtgc ttttcgccca      4320
gctacctcgc cagcccacat ctaagaaccc ctccctacgt cctgggtcgg aagggttgag      4380
actttcccca gtggtagtgt ctacgtttta cactttttgtg tttgacattt aaagctataa     4440
gttagctagc tataaagtgt cagaacttaa ggtcgagact ttttcttttt ggggctaggg     4500
agctgtgctt gccatattcc agtgttactc aaagaaacag tctcccttct ctgtctaccc     4560
acatttttat tggctctgtg ctcatgaggg ggtggagtcc ctgattattg gcagttcttg     4620
tgagggggcg gagtcttctg ttacagctgt gtgtctattc ctgcaccatc gagtcttgat      4680
tactgtgatg ataatatcag tctcaaaact gggtagagag tagaggac               4728
```

<210> SEQ ID NO 21
<211> LENGTH: 6706
<212> TYPE: DNA
<213> ORGANISM: Homo sapiens

<400> SEQUENCE: 21

```
atgggaaaca gctgttacaa catagtagcc actctgttgc tggtcctcaa ctttgagagg        60
acaagatcat tgcaggatcc ttgtagtaac tgcccagctg gtgagtaccc agttatcatg        120
```

```
tgcatttgat ctgctctgtt ggaagtatgg ttcagttagt ctagtagtca gggctaacga    180
gctccctttt aaggaaagga aaatgaaaat tcattcattt acaaatgttt attggatgct    240
acaacctagc tgtgtgaaca cagcaaagtc attcaacctc ttgtgccttg actttctcat    300
ctggggataa taagagaacc tgttttatag gatggctggg aggatcaaat gaagggctta    360
gaacagtgca tggcacaagg caagacttca ataaatgtta gttttgtgtg tagggctttg    420
tgctccgact gggggcatag cagcgagtaa gcgcgtagta aagggcttaa cagagtgggg    480
acggtcagtc gcatttaaat tttagtgtag acattgatg tcctcctgga tccagtcata    540
ttcatctcct acatcaatca agataatcat tttgttttat tcaatagata agtattttc     600 tttctgttga tttatttgtt acaatatctg gttttttttgt tttttttgtg tgtgtatgtt   660 ttttttttt tttttgagac acagtctcac tctgtcgccc aggctggagt gcagtggcac     720
gatctcagct cactgcaacc ttggcctccc aggttcaagc aattctcctg cctcagcctc    780
ccgagtagct gggattacag gtgtgcacca ctgcgcctgg ctaattttg tatttttagt     840 agagacagga tttcaccatg ttggccaagc tggtcttgaa ctgctgacct caggtgatct    900
gcccgcttcg gcctcccaaa gtgctgtgat tacaggcgtg agccactgca cctggcctgt    960
attttgttat ttctaattct gtgattacac aaagaataat cttgcaaatg tattgtttta   1020
ggaagtcaat caaactaatg tccaccactg tggcatctag aaaactcatc attcttttat   1080
aatcttattt tattgtaaac ttcggaatgc cttgggtgac gattgcccat tgtcaaacgt   1140
gtaccactat tgtctgcctt tcttaggtac attctgtgat aataacagga atcagatttg   1200
cagtccctgt cctccaaata gtttctccag cgcaggtgga caaggacct gtgacatatg    1260 caggcagtgt aaaggtatga gttcaaagat atttcttct tctagaagat agttgggaag    1320
ataagctttt ctttcccatt tactaactgc tctcttttga aaatctcaag tgtcaaagac   1380
tgattcttct gccaaccagc aggtctagga caataatatc cagtgacagc aattatttgt   1440
ggactgagct ttctaaatat tagaggaaac attcatttga caagagagaa gttttttactt  1500 acctaaatgt aaaaatgtct ttatggagat ttaaaagtaa actttaaaat tactgggaac   1560
actataagta gagtgagcat gattttttact gcagagcata aattcgcttc ctggatttgg  1620
aggtcaagtg taataaaatg ttgggggctg ggggactttt gtaggtgttt tcaggaccag   1680
gaaggagtgt tcctccacca gcaatgcaga gtgtgactgc actccagggt ttcactgcct   1740 ggggcagga tgcagcatgt gtgaacagga ttgtaaacaa ggtcaagaac tgacaaaaaa    1800
aggtacgttt gcgtttcttt gatctagtgt agttttgtga catagacaaa cttagctttg   1860
atcttgatcc tttgaaaata acaaacaga tttgtagaac cttaaagtaa caagggagta    1920
tatgatatat catattttaa ttaataaaat atttcaatta ataaaatatt tccgttattt    1980
cttcataaat ggaaataatt tgaaatcaga acatttgtta attgccagaa ccattaatct   2040
tcacatgttc cagacatata caatacttta tgtacaatta aaataaaaac tagccatctt   2100
agggtgttgt ttcaagaatt attgaacaat ttgtgcagat tgcattatgg taatgactta   2160
tattaagttc atcacaggaa aagttacaaa atgatgaaaa tgcttcccctt ttattattgc   2220 tttcattttt aatacaaggt tgtaaagact gttgctttgg gacatttaac gatcagaaac   2280
gtggcatctg tcgaccctgg acaaagtacg tataatttcc tttagtttat ggaataaaga   2340
atctgggtta aattttttgg aagataagga atgctatcat tgaagctttt ttgcacccat   2400
caagtgtaga cagaatgtaa catactaata ggcagcgtgg gaacactgtg aggtcgtagc   2460
```

-continued

```
aactcaatag gcaaagtggg cattttctcc agaaatagtg cctggaacat ctagatcaga   2520
attgccagtg gaggctgggc acgtgcagtg gttcacgcct gtaatcccag cactttggga   2580
ggctgagaca ggaggactcc ttgagcccag gagttcaaaa ccagcctggg tgagaccctg   2640
tctctacaaa aaatcaaaaa attagccagg cataatggca catgcctgtg gtcccagcta   2700
tagggaaggc tgatgaggca ggaggatcac ctgagtctgg gaggttgagg ctgcaatgag   2760
ctatgatcgc accatcgcac tccagagcag agagcctgtc tcaaaagaaa ggaaaagaat   2820
tgccagtgga actttgccgc tgtctgcctc ttttctgttt ccttctcatt cctttgctgc   2880
ctcttatctt ctctcattga tcagcctgtc tccatgtgtt caatgccagc ccctagaatg   2940
atacagaaga aactaacaat tgctcgttac cctccaaaat gtggcacaga cttgggcaca   3000
caaggccatc acaggtggta aaaagccaat agtatacgag agaatgtgac tgttgttttg   3060
tggaaccaga acttacactg tggtctgtgg atgggtgctg gtccacaaat ggcttgtcct   3120
gtgtccccat cgacagtggt gtagggttag agagtaaaca tttagaaact tttaaggcaa   3180
attggcagag taatgtggtc tgttgactaa gaataaaaat ttgggcgttg tattttatat   3240
gtatttgttc tttttccgtt tcattttctt actagaaaat catttttatt attttacttt   3300
tacattttta ttgtatttca aaagtgtatt ggtttgtaac agactggaaa gtgacttttt   3360
tgagagaaaa taaagtgttt tgaaacagga atcatggtat ctctctgctt ttgtcattta   3420
taatttatca gcatcagagt ggctgacgaa tggaatcatg attcacaaga aaagtattga   3480
ctattttctc ggacttagct gaattctgtc tttggaaagt ggcttttttta aaaaggtctg   3540
tttgtttgtt ttgtttgttt gtttgtttgt ttgttttgag atggagtttc gctcttcttg   3600
cccaggctgg agtgcaatgg cacggtctcg cctcactgca aactctgcct cctgggttca   3660
agagattctc ctgcctcggc ctcctagtag ctgggattac aggtgcacac aaccacgcct   3720
ggctagtgct tttgtatttt tagtagagat gggctttcac catgttagcc aggctggtct   3780
cgcactcctg acctcaagtg atccgcttgc cttggcctcc caaagtgctg ggattacagg   3840
tgtgagccac tgtgcccagc tggaaagtgg ctttttaaaa aaggtctttc aatacaaatt   3900
tttcagagtt gttaagtgag tctgcatgga aaaatgggtt tgaactgggc tctggaggac   3960
gggcggattt ggggtaggta aagggacaag ggaaaggtgt cacaacaaca gcaacaatga   4020
tggcgatgat ggtgataatg atagctacca tttactcagc gtgtcagatg tgcaagagtg   4080
tgtcactgac tctcactcgt ttgttctttg aaacagttct ggcagcacat acaatcctaa   4140
ttttgcagat gagaaaactg aggcttaggg aggtttcttt tttcttttct ttctgagaca   4200
gcgtcaaact cctgggttca agtgatcagc ctcaaactcc tgggttcaag tgatcctccc   4260
acctcagtct cccgagtagc tggggccaca ggcatgcacc atcagttaat ttttgtttgt   4320
cttttaattt ttgtagagat ggggtcttgc tatgttgctc aggctggtct ccaacgcctg   4380
gtctcaagtg atcctctggc ctcagcctac caaagtgttg agattatagg cgtgagccac   4440
catgctgggg ttacagagat ttcttgactt gcccaaagtc attctggaaa gcagcagacc   4500
cagggctcaa accctggttt gcctgatgct agtgctggac ctcctaaccc tatgctagcc   4560
ttcatctgtg ccggagatgg tcaagtccga ttaagaaact gggggtgaga gactaagcag   4620
gcaagacaga ctgaactaag ctgtcactga acagaaggaa gccatggaaa gctgcaggga   4680
gccagatggt caagtggaag tttttcaaaa tatctttgca tcgctttcga acccagaccc   4740
atatatcttt ttcactaggc tacttcattg ggtgaaaaat gacaaagttt taaaccagaa   4800
tcttctggac ctaagttaat tatttaaatt attttcattg aactgtctaa gctgttcttt   4860
```

```
ggatggaaag tctgtgcttg tgaatgggac gaaggagagg gacgtggtct gtggaccatc    4920
tccagccgac ctctctccgg gagcatcctc tgtgaccccg cctgcccctg cgagagagcc    4980
aggtaactgg gctatgcctt tacgccaaag tgcgtatctt atggtgattc cagattgtat    5040
ctaaattgcc ccaatatcat gatatctcat atcaggcacc tcccacgtgc attcttcctg    5100
aatcctgccc tcagggaccc agcagttttc ttcccaggca tttgttattc agtctgagat    5160
acacatttgt aagcggtgcc agaggacact cacccaaac agagtctata tctttatcaa     5220
tgccaaggaa aggggattat agggtcccat attttttctt ttcttttctt ttctttttttt    5280 ttgtttttaa gagagtgtct tgctctgtgc caggctggag tgcagtggtg cagtctcagc    5340
tcactgcaat ctccacctcc tgggttcaag tgattctcct gcctcagcct cccaagtagc    5400
tgggattata ggcatgcacc accacgcccg gctaattttt gtattttag tagagatgag     5460 gtttcaccat gctggccagt ctggtcttga actcctgacc gcatgatccg cccacctcgg    5520
cctcccaaag tgctgggatt acaggtgtga gccaccacgc ccgtccaggg tcccatattt    5580
tcttttcttt tttctttctc tctctcgctt ttttttttccc ccgagagtgc cttgttctgt    5640
gccaggctgg agtgcagtgg cttgatattg gctcactgca acctccacct cctgtgctca    5700
accaatcctc ccacctcagc ctccccagta gctgggacta taggcactca ccactacacc    5760
tggctaattt tttatttttt tggcagagtc ggggtcttgc tatgttgctc aggctgctct    5820
caaactcttg ggctcaagca atcctcctgc cttgggctcc caaagtgttg ggattacagg    5880
cataagccgc cacgcctggt ccccaggtcc catatttttct atgtgctaga aaggataaac    5940
tgctcaatta ttaagtttct tttattttt tgggggggtg gacagagtct ctctctgtca     6000
cccaggctgg agtgcaatgg cgcaatctcg gctcactgca acctctacct cccaggttca    6060
agcgattctc ctgactcagc ctcctgagta gctgggatta caggcgccca ccacggcacc    6120
cagctaattt ttgtattttt agtagagatg gagtttctcc atgttggcca ggctggtttc    6180
aaactcttga cctcaggtga tctgcccacc ttggcctccc aaagtgctag gattacaggt    6240
gtgagccacc gctccctgcc attaagtttc tcttttctt ttctttctt tcttttttt       6300 gagatggagt ctcactctgt tgcccaggtt ggagtgcagt ggcaccatct tagctcactg    6360
caacctccgc ctcccgggtt caagccattc tcctgcctca tcctgccaag tagctgggat    6420
tacaagttcc tgccaccact atgttggcca ggctggtctt gaactcctga ctctaagtga    6480
tcctcctgcc tcggccttcc aaagtgttgg gattacaggc gtgagccacc atgtctggcc    6540
tctttaaaag ttttctaagt ttactccatt agcaggttgg agatgcccaa ggctgtgatt    6600
cttctcatgc ttagaaattt accaatgtaa atatatacat gggtgtatga gtgtcaacac    6660
atttctgcat gcgtttctcc ttttgctgtg ttttgcagga cactct                   6706
```

<210> SEQ ID NO 22
<211> LENGTH: 774
<212> TYPE: DNA
<213> ORGANISM: Artificial
<220> FEATURE:
<223> OTHER INFORMATION: Homo sapiens and Mus musculus

<400> SEQUENCE: 22

```
atgggaaaca gctgttacaa catagtagcc actctgttgc tggtcctcaa ctttgagagg      60
acaagatcat tgcaggatcc ttgtagtaac tgcccagctg gtacattctg tgataataac     120
aggaatcaga tttgcagtcc ctgtcctcca aatagtttct ccagcgcagg tggacaaagg     180
```

-continued

| | |
|---|---|
| acctgtgaca tatgcaggca gtgtaaaggt gttttcagga ccaggaagga gtgttcctcc | 240 |
| accagcaatg cagagtgtga ctgcactcca gggtttcact gcctgggggc aggatgcagc | 300 |
| atgtgtgaac aggattgtaa acaaggtcaa gaactgacaa aaaaaggttg taaagactgt | 360 |
| tgctttggga catttaacga tcagaaacgt ggcatctgtc gaccctggac aaactgttct | 420 |
| ttggatggaa agtctgtgct tgtgaatggg acgaaggaga gggacgtggt ctgtggacca | 480 |
| tctccagccg acctctctcc gggagcatcc tctgtgaccc cgcctgcccc tgcgagagag | 540 |
| ccaggacact cttttgcaggt ccttaccttg ttcctggcgc tgacatcggc tttgctgctg | 600 |
| gccctgatct tcattactct cctgttctct gtgctcaaat ggatcaggaa aaaattcccc | 660 |
| cacatattca agcaaccatt taagaagacc actggagcag ctcaagagga agatgcttgt | 720 |
| agctgccgat gtccacagga agaagaagga ggaggaggag gctatgagct gtga | 774 |

<210> SEQ ID NO 23
<211> LENGTH: 2137
<212> TYPE: DNA
<213> ORGANISM: Artificial
<220> FEATURE:
<223> OTHER INFORMATION: Homo sapiens and Mus musculus

<400> SEQUENCE: 23

| | |
|---|---|
| ttcctgaaat tcaggtgctg caggcagccc tcagcacaga gagctgacag ggaccctggg | 60 |
| tcaggggttc tgagttccag ctgccactat tcttcttcac ctttggtgtc ctgtgcatgt | 120 |
| gacatttcgc catgggaaac agctgttaca acatagtagc cactctgttg ctggtcctca | 180 |
| actttgagag gacaagatca ttgcaggatc cttgtagtaa ctgcccagct ggtacattct | 240 |
| gtgataataa caggaatcag atttgcagtc cctgtcctcc aaatagtttc tccagcgcag | 300 |
| gtggacaaag gacctgtgac atatgcaggc agtgtaaagg tgttttcagg accaggaagg | 360 |
| agtgttcctc caccagcaat gcagagtgtg actgcactcc agggtttcac tgcctggggg | 420 |
| caggatgcag catgtgtgaa caggattgta acaaggtcaa gaactgaca aaaaaaggtt | 480 |
| gtaaagactg ttgctttggg acatttaacg atcagaaacg tggcatctgt cgaccctgga | 540 |
| caaactgttc tttggatgga agtctgtgc ttgtgaatgg gacgaaggag agggacgtgg | 600 |
| tctgtggacc atctccagcc gacctctctc cgggagcatc ctctgtgacc ccgcctgccc | 660 |
| ctgcgagaga gccaggacac tcttttgcagg tccttacctt gttcctggcg ctgacatcgg | 720 |
| ctttgctgct ggccctgatc ttcattactc tcctgttctc tgtgctcaaa tggatcagga | 780 |
| aaaaattccc ccacatattc aagcaaccat ttaagaagac cactggagca gctcaagagg | 840 |
| aagatgcttg tagctgccga tgtccacagg aagaagaagg aggaggagga ggctatgagc | 900 |
| tgtgatgtac tatcctagga gatgtgtggg ccgaaaccga gaagcactag gaccccacca | 960 |
| tcctgtggaa cagcacaagc aaccccacca ccctgttctt acacatcatc ctagatgatg | 1020 |
| tgtgggcgcg cacctcatcc aagtctcttc taacgctaac atatttgtct ttacttttttt | 1080 |
| taaatctttt tttaaattta aatttttatgt gtgtgagtgt tttgcctgcc tgtatgcaca | 1140 |
| cgtgtgtgtg tgtgtgtgtg tgacactcct gatgcctgag gaggtcagaa gagaaagggt | 1200 |
| tggttccata agaactggag ttatggatgg ctgtgagcct ttgtgtgggt gctaggaatc | 1260 |
| aaacctgggt cctctacaag ggcagccagt gctcttaacc actgagtcag ctttccagcc | 1320 |
| ctgccctgga cagttttttaa aatttaactt aatttttttt tttttttact taagcccta | 1380 |
| acatttttaa taggactgtg ggaagatcaa tttctagatt ctccttaaca atatacatca | 1440 |
| tatacatata cacatacata tacatataca tatatattct gagaaaatga cagtttcagt | 1500 |

```
tggatctcat agaccaatgg tccagttaaa ataactgtaa atcagtgtg tgtgtgtgtg   1560 tgtgtgtgtg tgtgcaaata tgatgcatga caatagccat aagatgcagt atattaccct   1620
atcccatttt cctttggttt ctcactcact ataataacac ctccactgtc tgaaggggga   1680
gacccatgca tccctgtctg gaggaagcct gacagatttt gagggaatc ttcagagcag   1740 ttcaagggcc tgcttctcct gtttcctctg tgtcaggctt ttcaataaaa aggccgttta   1800
ggaaagggac aaagcactgt gaggtgggga cacctgtga actcacagta ggaacgcggc   1860
cttccagtcc accatgggca gacatggctg ccgcttgcct ctgcatgact cctggacagc   1920
tcaagagctg agaatggttg ttactttct ttattttgag acagcacctc cctctgtagt   1980
gctggctggc ctggaagtca cagaaatcct cctgcctctg cttccagagt actgggtctt   2040
aaactgttca ccacgtctcc cctcccaac ccaaaacta gcctttccat ttttaaaagc   2100
cagctaaaaa tattaaagtt gtgctcttac aaaagtc                           2137
```

<210> SEQ ID NO 24
<211> LENGTH: 256
<212> TYPE: PRT
<213> ORGANISM: Artificial
<220> FEATURE:
<223> OTHER INFORMATION: Homo sapiens and Mus musculus

<400> SEQUENCE: 24

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Leu Gln Val Leu Thr Leu Phe Leu
            180                 185                 190

Ala Leu Thr Ser Ala Leu Leu Leu Ala Leu Ile Phe Ile Thr Leu Leu
        195                 200                 205

Phe Ser Val Leu Lys Trp Ile Arg Lys Lys Phe Pro His Ile Phe Lys
    210                 215                 220

Gln Pro Phe Lys Lys Thr Thr Gly Ala Ala Gln Glu Glu Asp Ala Cys
225                 230                 235                 240

Ser Cys Arg Cys Pro Gln Glu Glu Glu Gly Gly Gly Gly Gly Tyr Glu
```

<210> SEQ ID NO 25
<211> LENGTH: 8989
<212> TYPE: DNA
<213> ORGANISM: Artificial
<220> FEATURE:
<223> OTHER INFORMATION: Homo sapiens and Mus musculuswith modification

<400> SEQUENCE: 25

| | | | | | |
|---|---|---|---|---|---|
| atgggaaaca | gctgttacaa | catagtagcc | actctgttgc | tggtcctcaa | ctttgagagg | 60 |
| acaagatcat | tgcaggatcc | ttgtagtaac | tgcccagctg | gtgagtaccc | agttatcatg | 120 |
| tgcatttgat | ctgctctgtt | ggaagtatgg | ttcagttagt | ctagtagtca | gggctaacga | 180 |
| gctcccttt | aaggaaagga | aaatgaaaat | tcattcattt | acaaatgttt | attggatgct | 240 |
| acaacctagc | tgtgtgaaca | cagcaaagtc | attcaacctc | ttgtgccttg | actttctcat | 300 |
| ctggggataa | taagagaacc | tgttttatag | gatggctggg | aggatcaaat | gaagggctta | 360 |
| gaacagtgca | tggcacaagg | caagacttca | ataaatgtta | gttttgtgtg | tagggctttg | 420 |
| tgctccgact | gggggcatag | cagcgagtaa | gcgcgtagta | aagggcttaa | cagagtgggg | 480 |
| acggtcagtc | gcatttaaat | tttagtgtag | gacattgatg | tcctcctgga | tccagtcata | 540 |
| ttcatctcct | acatcaatca | agataatcat | tttgttttat | tcaatagata | aagtattttc | 600 |
| tttctgttga | tttatttgtt | acaatatctg | gttttttgt | ttttttttgtg | tgtgtatgtt | 660 |
| ttttttttt | ttttgagac | acagtctcac | tctgtcgccc | aggctggagt | gcagtggcac | 720 |
| gatctcagct | cactgcaacc | ttggcctccc | aggttcaagc | aattctcctg | cctcagcctc | 780 |
| ccgagtagct | gggattacag | gtgtgcacca | ctgcgcctgg | ctaattttg | tatttttagt | 840 |
| agagacagga | tttcaccatg | ttggccaagc | tggtcttgaa | ctgctgacct | caggtgatct | 900 |
| gcccgcttcg | gcctcccaaa | gtgctgtgat | tacaggcgtg | agccactgca | cctggcctgt | 960 |
| attttgttat | ttctaattct | gtgattacac | aaagaataat | cttgcaaatg | tattgttta | 1020 |
| ggaagtcaat | caaactaatg | tccaccactg | tggcatctag | aaaactcatc | attctttat | 1080 |
| aatcttattt | tattgtaaac | ttcggaatgc | cttgggtgac | gattgcccat | tgtcaaacgt | 1140 |
| gtaccactat | tgtctgcctt | tcttaggtac | attctgtgat | aataacagga | atcagatttg | 1200 |
| cagtccctgt | cctccaaata | gtttctccag | cgcaggtgga | caaaggacct | gtgacatatg | 1260 |
| caggcagtgt | aaaggtatga | gttcaaagat | atttctttct | tctagaagat | agttgggaag | 1320 |
| ataagctttt | ctttcccatt | tactaactgc | tctcttttga | aaatctcaag | tgtcaaagac | 1380 |
| tgattcttct | gccaaccagc | aggtctagga | caataatatc | cagtgacagc | aattatttgt | 1440 |
| ggactgagct | ttctaaatat | tagaggaaac | attcatttga | caagagagaa | gttttactt | 1500 |
| acctaaatgt | aaaaatgtct | ttatggagat | ttaaaagtaa | actttaaaat | tactgggaac | 1560 |
| actataagta | gagtgagcat | gattttttact | gcagagcata | aattcgcttc | ctggatttgg | 1620 |
| aggtcaagtg | taataaaatg | ttggggggctg | ggggggacttt | gtaggtgttt | tcaggaccag | 1680 |
| gaaggagtgt | tcctccacca | gcaatgcaga | gtgtgactgc | actccagggt | tcactgcct | 1740 |
| gggggcagga | tgcagcatgt | gtgaacagga | ttgtaaacaa | ggtcaagaac | tgacaaaaaa | 1800 |
| aggtacgttt | gcgtttcttt | gatctagtgt | agttttgtga | catagacaaa | cttagctttg | 1860 |
| atcttgatcc | tttgaaaata | aacaaacaga | tttgtagaac | cttaaagtaa | caagggagta | 1920 |
| tatgatatat | catattttaa | ttaataaaat | atttcaatta | ataaaatatt | tccgttattt | 1980 |
| cttcataaat | ggaaataatt | tgaaatcaga | acatttgtta | attgccagaa | ccattaatct | 2040 |

```
tcacatgttc cagacatata caatacttta tgtacaatta aaataaaaac tagccatctt    2100
agggtgttgt ttcaagaatt attgaacaat ttgtgcagat tgcattatgg taatgactta    2160
tattaagttc atcacaggaa aagttacaaa atgatgaaaa tgcttccctt ttattattgc    2220
tttcattttt aatacaaggt tgtaaagact gttgctttgg gacatttaac gatcagaaac    2280
gtggcatctg tcgaccctgg acaaagtacg tataatttcc tttagtttat ggaataaaga    2340 atctggggtta aatttttttgg aagataagga atgctatcat tgaagctttt ttgcacccat    2400
caagtgtaga cagaatgtaa catactaata ggcagcgtgg gaacactgtg aggtcgtagc    2460
aactcaatag gcaaagtggg cattttctcc agaaatagtg cctggaacat ctagatcaga    2520
attgccagtg gaggctgggc acgtgcagtg gttcacgcct gtaatcccag cactttggga    2580
ggctgagaca ggaggactcc ttgagcccag gagttcaaaa ccagcctggg tgagaccctg    2640
tctctacaaa aaatcaaaaa attagccagg cataatggca catgcctgtg gtcccagcta    2700
tagggaaggc tgatgaggca ggaggatcac ctgagtctgg gaggttgagg ctgcaatgag    2760
ctatgatcgc accatcgcac tccagagcag agagcctgtc tcaaaagaaa ggaaaagaat    2820
tgccagtgga actttgccgc tgtctgcctc ttttctgttt ccttctcatt cctttgctgc    2880
ctcttatctt ctctcattga tcagcctgtc tccatgtgtt caatgccagc ccctagaatg    2940
atacagaaga aactaacaat tgctcgttac cctccaaaat gtggcacaga cttgggcaca    3000
caaggccatc acaggtggta aaaagccaat agtatacgag agaatgtgac tgttgttttg    3060
tggaaccaga acttacactg tggtctgtgg atgggtgctg gtccacaaat ggcttgtcct    3120
gtgtccccat cgacagtggt gtagggttag agagtaaaca tttagaaact tttaaggcaa    3180
attggcagag taatgtggtc tgttgactaa gaataaaaat ttgggcgttg tattttatat    3240
gtatttgttc ttttttccgtt tcattttctt actagaaaat cattttttatt attttacttt    3300 tacatttttta ttgtatttca aaagtgtatt ggtttgtaac agactggaaa gtgacttttt    3360
tgagagaaaa taaagtgttt tgaaacagga atcatggtat ctctctgctt ttgtcattta    3420
taatttatca gcatcagagt ggctgacgaa tggaatcatg attcacaaga aaagtattga    3480 ctatttttctc ggacttagct gaattctgtc tttggaaagt ggcttttttta aaaaggtctg    3540 tttgtttgtt ttgtttgttt gtttgtttgt ttgttttgag atggagtttc gctcttcttg    3600
cccaggctgg agtgcaatgg cacggtctcg cctcactgca aactctgcct cctgggttca    3660
agagattctc ctgcctcggc ctcctagtag ctgggattac aggtgcacac aaccacgcct    3720
ggctagtgct tttgtatttt tagtagagat gggctttcac catgttagcc aggctggtct    3780
cgcactcctg acctcaagtg atccgcttgc cttggcctcc caaagtgctg ggattacagg    3840
tgtgagccac tgtgcccagc tggaaagtgg cttttttaaaa aaggtctttc aatacaaatt    3900
tttcagagtt gttaagtgag tctgcatgga aaaatgggtt tgaactgggc tctggaggac    3960
gggcggattt ggggtaggta aagggacaag ggaaaggtgt cacaacaaca gcaacaatga    4020
tggcgatgat ggtgataatg atagctacca tttactcagc gtgtcagatg tgcaagagtg    4080
tgtcactgac tctcactcgt tgttctttg aaacagttct ggcagcacat acaatcctaa    4140
ttttgcagat gagaaaactg aggcttaggg aggtttcttt tttctttttct ttctgagaca    4200 gcgtcaaact cctgggttca agtgatcagc ctcaaactcc tgggttcaag tgatcctccc    4260
acctcagtct cccgagtagc tggggccaca ggcatgcacc atcagttaat ttttgtttgt    4320 ctttttaattt ttgtagagat ggggtcttgc tatgttgctc aggctggtct ccaacgcctg    4380
```

```
gtctcaagtg atcctctggc ctcagcctac caaagtgttg agattatagg cgtgagccac   4440
catgctgggg ttacagagat ttcttgactt gcccaaagtc attctggaaa gcagcagacc   4500
cagggctcaa accctggttt gcctgatgct agtgctggac ctcctaaccc tatgctagcc   4560
ttcatctgtg ccggagatgg tcaagtccga ttaagaaact gggggtgaga gactaagcag   4620
gcaagacaga ctgaactaag ctgtcactga acagaaggaa gccatggaaa gctgcaggga   4680
gccagatggt caagtggaag ttttttcaaaa tatctttgca tcgctttcga acccagaccc   4740
atatatcttt ttcactaggc tacttcattg ggtgaaaaat gacaaagttt taaaccagaa   4800
tcttctggac ctaagttaat tatttaaatt attttcattg aactgtctaa gctgttcttt   4860
ggatggaaag tctgtgcttg tgaatgggac gaaggagagg gacgtggtct gtggaccatc   4920
tccagccgac ctctctccgg gagcatcctc tgtgaccccg cctgccctg cgagagagcc   4980 aggtaactgg gctatgcctt tacgccaaag tgcgtatctt atggtgattc cagattgtat   5040
ctaaattgcc caatatcat gatatctcat atcaggcacc tcccacgtgc attcttcctg   5100
aatcctgccc tcagggaccc agcagttttc ttcccaggca tttgttattc agtctgagat   5160
acacatttgt aagcggtgcc agaggacact tcacccaaac agagtctata tctttatcaa   5220
tgccaaggaa aggggattat agggtcccat attttttctt ttcttttctt ttcttttttt   5280
ttgtttttaa gagagtgtct tgctctgtgc caggctggag tgcagtggtg cagtctcagc   5340
tcactgcaat ctccacctcc tgggttcaag tgattctcct gcctcagcct cccaagtagc   5400
tgggattata ggcatgcacc accacgcccg gctaattttt gtattttag tagagatgag   5460 gtttcaccat gctggccagt ctggtcttga actcctgacc gcatgatccg cccacctcgg   5520
cctcccaaag tgctgggatt acaggtgtga gccaccacgc ccgtccaggg tcccatattt   5580
tcttttcttt tttcttttctc tctctcgctt ttttttccc ccgagagtgc cttgttctgt   5640
gccaggctgg agtgcagtgg cttgatattg gctcactgca acctccacct cctgtgctca   5700
accaatcctc ccacctcagc ctccccagta gctgggacta taggcactca ccactacacc   5760
tggctaattt tttatttttt tggcagagtc ggggtcttgc tatgttgctc aggctgctct   5820
caaactcttg ggctcaagca atcctcctgc cttgggctcc caaagtgttg ggattacagg   5880
cataagccgc cacgcctggt ccccaggtcc catattttct atgtgctaga aaggataaac   5940
tgctcaatta ttaagtttct tttattttt tggggggtg gacagagtct ctctctgtca   6000
cccaggctgg agtgcaatgg cgcaatctcg gctcactgca acctctacct cccaggttca   6060
agcgattctc ctgactcagc ctcctgagta gctgggatta caggcgccca ccacggcacc   6120
cagctaattt ttgtattttt agtagagatg agtttctcc atgttggcca ggctggtttc   6180
aaactcttga cctcaggtga tctgcccacc ttggcctccc aaagtgctag gattacaggt   6240
gtgagccacc gctccctgcc attaagtttc tcttttctt ttctttcttt tctttttttt   6300
gagatggagt ctcactctgt tgcccaggtt ggagtgcagt ggcaccatct tagctcactg   6360
caacctccgc ctcccgggtt caagccattc tcctgcctca tcctgccaag tagctgggat   6420
tacaagttcc tgccaccact atgttggcca ggctggtctt gaactcctga ctctaagtga   6480
tcctcctgcc tcggccttcc aaagtgttgg gattacaggc gtgagccacc atgtctggcc   6540
tctttaaaag ttttctaagt ttactccatt agcaggttgg agatgcccaa ggctgtgatt   6600
cttctcatgc ttagaaattt accaatgtaa atatatacat gggtgtatga gtgtcaacac   6660
atttctgcat gcgtttctcc ttttgctgtg ttttgcagga cactctttgc aggtccttac   6720
cttgttcctg gcgctgacat cggctttgct gctggccctg atcttcatta ctctcctgtt   6780
```

```
ctctgtgctc aaatggatca ggaaaaaatt cccccacata ttcaagcaac gtaaggccaa   6840
cacagcatgg gatgtggggg caggcaggac acacgtctgg agtcagagga cagtctctct   6900
ctcggaatgt gttgtcttcc tgtttcaggg actggatgga cgcaggtcct caggctttcg   6960
tggtgggaat gcctttactc acccatccat attgcaggct tggattttt ttttttttaag   7020 ttatgggcat acagttggct agcccatggt tgcaaagcca gaacaagctt gctcccacaa   7080
ggatattgct cgaggtcgac ggtatcgata agcttgatat cgaattccga agttcctatt   7140
ctctagaaag tataggaact tcaggtctga agaggagttt acgtccagcc aagctagctt   7200
ggctgcaggt cgtcgaaatt ctaccgggta ggggaggcgc ttttcccaag gcagtctgga   7260
gcatgcgctt tagcagcccc gctgggcact ggcgctaca caagtggcct ctggcctcgc   7320
acacattcca catccaccgg taggcgccaa ccggctccgt tctttggtgg ccccttcgcg   7380
ccaccttcta ctcctcccct agtcaggaag ttcccccccg cccgcagct cgcgtcgtgc   7440 aggacgtgac aaatggaagt agcacgtctc actagtctcg tgcagatgga cagcaccgct   7500
gagcaatgga agcgggtagg cctttggggc agcggccaat agcagctttg ctccttcgct   7560
ttctgggctc agaggctggg aaggggtggg tccggggcg ggctcagggg cgggctcagg   7620
ggcggggcgg gcgcccgaag gtcctccgga ggcccggcat tctgcacgct tcaaaagcgc   7680
acgtctgccg cgctgttctc ctcttcctca tctccgggcc tttcgacctg cagcctgttg   7740
acaattaatc atcggcatag tatatcggca tagtataata cgacaaggtg aggaactaaa   7800
ccatgggatc ggccattgaa caagatggat tgcacgcagg ttctccggcc gcttgggtgg   7860
agaggctatt cggctatgac tgggcacaac agacaatcgg ctgctctgat gccgccgtgt   7920
tccggctgtc agcgcagggg cgcccggttc ttttgtcaa gaccgacctg tccggtgccc   7980
tgaatgaact gcaggacgag gcagcgcggc tatcgtggct ggccacgacg ggcgttcctt   8040
gcgcagctgt gctcgacgtt gtcactgaag cgggaaggga ctggctgcta ttgggcgaag   8100
tgccggggca ggatctcctg tcatctcacc ttgctcctgc cgagaaagta tccatcatgg   8160
ctgatgcaat gcggcggctg catacgcttg atccggctac ctgcccattc gaccaccaag   8220
cgaaacatcg catcgagcga gcacgtactc ggatggaagc cggtcttgtc gatcaggatg   8280
atctggacga agagcatcag gggctcgcgc cagccgaact gttcgccagg ctcaaggcgc   8340
gcatgcccga cggcgatgat ctcgtcgtga cccatggcga tgcctgcttg ccgaatatca   8400
tggtggaaaa tggccgcttt tctggattca tcgactgtgg ccggctgggt gtggcggacc   8460
gctatcagga catagcgttg gctacccgtg atattgctga agagcttggc ggcgaatggg   8520
ctgaccgctt cctcgtgctt tacggtatcg ccgctcccga ttcgcagcgc atcgccttct   8580
atcgccttct tgacgagttc ttctgagggg atcaattctc tagagctcgc tgatcagcct   8640
cgactgtgcc ttctagttgc cagccatctg ttgtttgccc ctcccccgtg ccttccttga   8700
ccctggaagg tgccactccc actgtccttt cctaataaaa tgaggaaatt gcatcgcatt   8760
gtctgagtag gtgtcattct attctggggg gtggggtggg gcaggacagc aaggggagg   8820 attgggaaga caatagcagg catgctgggg atgcggtggg ctctatggct tctgaggcgg   8880
aaagaaccag ctggggctcg actagagctt gcggaaccct cgaagttcc tattctctag   8940 aaagtatagg aacttcatca gtcaggtaca taatggtgga tccaggcct                8989
```

<210> SEQ ID NO 26
<211> LENGTH: 1862
<212> TYPE: DNA

<213> ORGANISM: Artificial
<220> FEATURE:
<223> OTHER INFORMATION: Synthesized sequence

<400> SEQUENCE: 26

```
gaattccgaa gttcctattc tctagaaagt ataggaactt caggtctgaa gaggagttta      60
cgtccagcca agctagcttg gctgcaggtc gtcgaaattc taccgggtag gggaggcgct     120
tttcccaagg cagtctggag catgcgcttt agcagcccg ctgggcactt ggcgctacac      180
aagtggcctc tggcctcgca cacattccac atccaccggt aggcgccaac cggctccgtt     240
ctttggtggc cccttcgcgc caccttctac tcctccccta gtcaggaagt tccccccgc      300
cccgcagctc gcgtcgtgca ggacgtgaca aatggaagta gcacgtctca ctagtctcgt     360
gcagatggac agcaccgctg agcaatgaaa gcgggtaggc ctttggggca gcggccaata     420
gcagctttgc tccttcgctt tctgggctca gaggctggga aggggtgggt ccggggggcgg   480
gctcagggc gggctcaggg gcggggcggg cgcccgaagg tcctccggag gcccggcatt      540
ctgcacgctt caaaagcgca cgtctgccgc gctgttctcc tcttcctcat ctccgggcct     600
ttcgacctgc agcctgttga caattaatca tcggcatagt atatcggcat agtataatac     660
gacaaggtga ggaactaaac catgggatcg gccattgaac aagatggatt gcacgcaggt     720
tctccggccg cttgggtgga gaggctattc ggctatgact gggcacaaca gacaatcggc    780
tgctctgatg ccgccgtgtt ccggctgtca gcgcaggggc gcccggttct ttttgtcaag    840
accgacctgt ccggtgccct gaatgaactg caggacgagg cagcgcggct atcgtggctg    900
gccacgacgg gcgttccttg cgcagctgtg ctcgacgttg tcactgaagc gggaagggac    960
tggctgctat tgggcgaagt gccggggcag gatctcctgt catctcacct tgctcctgcc   1020
gagaaagtat ccatcatggc tgatgcaatg cggcggctgc atacgcttga tccggctacc   1080
tgcccattcg accaccaagc gaaacatcgc atcgagcgag cacgtactcg gatggaagcc   1140
ggtcttgtcg atcaggatga tctggacgaa gagcatcagg ggctcgcgcc agccgaactg   1200
ttcgccaggc tcaaggcgcg catgcccgac ggcgatgatc tcgtcgtgac ccatggcgat   1260
gcctgcttgc cgaatatcat ggtggaaaat ggccgctttt ctggattcat cgactgtggc   1320
cggctgggtg tggcggaccg ctatcaggac atagcgttgg ctacccgtga tattgctgaa   1380
gagcttggcg gcgaatgggc tgaccgcttc ctcgtgcttt acggtatcgc cgctcccgat   1440
tcgcagcgca tcgccttcta tcgccttctt gacgagttct tctgagggga tcaattctct   1500
agagctcgct gatcagcctc gactgtgcct tctagttgcc agccatctgt tgtttgcccc   1560
tcccccgtgc cttccttgac cctggaaggt gccactccca ctgtcctttc ctaataaaat   1620
gaggaaattg catcgcattg tctgagtagg tgtcattcta ttctgggggg tggggtgggg   1680
caggacagca agggggagga ttgggaagac aatagcaggc atgctgggga tgcggtgggc   1740
tctatggctt ctgaggcgga aagaaccagc tggggctcga ctagagcttg cggaacccctt  1800
cgaagttcct attctctaga aagtatagga acttcatcag tcaggtacat aatggtggat   1860
cc                                                                 1862
```

<210> SEQ ID NO 27
<211> LENGTH: 27
<212> TYPE: DNA
<213> ORGANISM: Artificial
<220> FEATURE:
<223> OTHER INFORMATION: PCR primer

<400> SEQUENCE: 27

-continued

```
gtttagcaag catgctatca gtcaagc                                        27

<210> SEQ ID NO 28
<211> LENGTH: 27
<212> TYPE: DNA
<213> ORGANISM: Artificial
<220> FEATURE:
<223> OTHER INFORMATION: PCR primer

<400> SEQUENCE: 28
ctgaactgag tcttcaacag tcatgtc                                        27

<210> SEQ ID NO 29
<211> LENGTH: 23
<212> TYPE: DNA
<213> ORGANISM: Artificial
<220> FEATURE:
<223> OTHER INFORMATION: PCR primer

<400> SEQUENCE: 29
cacacagcta ggttgtagca tcc                                            23

<210> SEQ ID NO 30
<211> LENGTH: 24
<212> TYPE: DNA
<213> ORGANISM: Artificial
<220> FEATURE:
<223> OTHER INFORMATION: PCR primer

<400> SEQUENCE: 30
gacacacgtc tggagtcaga ggac                                           24

<210> SEQ ID NO 31
<211> LENGTH: 24
<212> TYPE: DNA
<213> ORGANISM: Artificial
<220> FEATURE:
<223> OTHER INFORMATION: PCR primer

<400> SEQUENCE: 31
ctcgctatac aactgcctcc aggc                                           24

<210> SEQ ID NO 32
<211> LENGTH: 25
<212> TYPE: DNA
<213> ORGANISM: Artificial
<220> FEATURE:
<223> OTHER INFORMATION: PCR primer

<400> SEQUENCE: 32
gacaagcgtt agtaggcaca tatac                                          25

<210> SEQ ID NO 33
<211> LENGTH: 24
<212> TYPE: DNA
<213> ORGANISM: Artificial
<220> FEATURE:
<223> OTHER INFORMATION: PCR primer

<400> SEQUENCE: 33
gctccaattt cccacaacat tagt                                           24

<210> SEQ ID NO 34
<211> LENGTH: 20
<212> TYPE: DNA
```

```
<213> ORGANISM: Artificial
<220> FEATURE:
<223> OTHER INFORMATION: PCR primer

<400> SEQUENCE: 34
gaacggtact ggcgtctgtc                                                    20

<210> SEQ ID NO 35
<211> LENGTH: 20
<212> TYPE: DNA
<213> ORGANISM: Artificial
<220> FEATURE:
<223> OTHER INFORMATION: PCR primer

<400> SEQUENCE: 35
ggtcctccct ctggagtcac                                                    20

<210> SEQ ID NO 36
<211> LENGTH: 20
<212> TYPE: DNA
<213> ORGANISM: Artificial
<220> FEATURE:
<223> OTHER INFORMATION: PCR primer

<400> SEQUENCE: 36
ctgcactcca gggtttcact                                                    20

<210> SEQ ID NO 37
<211> LENGTH: 20
<212> TYPE: DNA
<213> ORGANISM: Artificial
<220> FEATURE:
<223> OTHER INFORMATION: PCR primer

<400> SEQUENCE: 37
agtttgtcca gggtcgacag                                                    20

<210> SEQ ID NO 38
<211> LENGTH: 25
<212> TYPE: DNA
<213> ORGANISM: Artificial
<220> FEATURE:
<223> OTHER INFORMATION: PCR primer

<400> SEQUENCE: 38
cttccacatg agcgtggtca gggcc                                              25

<210> SEQ ID NO 39
<211> LENGTH: 25
<212> TYPE: DNA
<213> ORGANISM: Artificial
<220> FEATURE:
<223> OTHER INFORMATION: PCR primer

<400> SEQUENCE: 39
ccaagggact attttagatg ggcag                                              25

<210> SEQ ID NO 40
<211> LENGTH: 26
<212> TYPE: DNA
<213> ORGANISM: Artificial
<220> FEATURE:
<223> OTHER INFORMATION: PCR primer

<400> SEQUENCE: 40
gaagctacaa gctcctaggt aggggg                                             26
```

<210> SEQ ID NO 41
<211> LENGTH: 23
<212> TYPE: DNA
<213> ORGANISM: Artificial
<220> FEATURE:
<223> OTHER INFORMATION: PCR primer

<400> SEQUENCE: 41
acgggttggc tcaaaccatt aca                                            23

<210> SEQ ID NO 42
<211> LENGTH: 20
<212> TYPE: DNA
<213> ORGANISM: Artificial
<220> FEATURE:
<223> OTHER INFORMATION: PCR primer

<400> SEQUENCE: 42
ccgtgcagaa ctcctgtgat                                                20

<210> SEQ ID NO 43
<211> LENGTH: 20
<212> TYPE: DNA
<213> ORGANISM: Artificial
<220> FEATURE:
<223> OTHER INFORMATION: PCR primer

<400> SEQUENCE: 43
gttttgcaac cctgcttcgt                                                20

<210> SEQ ID NO 44
<211> LENGTH: 20
<212> TYPE: DNA
<213> ORGANISM: Artificial
<220> FEATURE:
<223> OTHER INFORMATION: PCR primer

<400> SEQUENCE: 44
cctggctcac agtgtcagag                                                20

<210> SEQ ID NO 45
<211> LENGTH: 20
<212> TYPE: DNA
<213> ORGANISM: Artificial
<220> FEATURE:
<223> OTHER INFORMATION: PCR primer

<400> SEQUENCE: 45
cagggctctc ctcgattttt                                                20

<210> SEQ ID NO 46
<211> LENGTH: 20
<212> TYPE: DNA
<213> ORGANISM: Artificial
<220> FEATURE:
<223> OTHER INFORMATION: PCR primer

<400> SEQUENCE: 46
ccctgctcgt ggtgaccgaa                                                20

<210> SEQ ID NO 47
<211> LENGTH: 20
<212> TYPE: DNA
<213> ORGANISM: Artificial
<220> FEATURE:

```
<223> OTHER INFORMATION: PCR primer

<400> SEQUENCE: 47
gcaggctctc tttgatctgc                                              20

<210> SEQ ID NO 48
<211> LENGTH: 25
<212> TYPE: DNA
<213> ORGANISM: Artificial
<220> FEATURE:
<223> OTHER INFORMATION: PCR primer

<400> SEQUENCE: 48
ccagggaggt ggcccactga taata                                        25

<210> SEQ ID NO 49
<211> LENGTH: 25
<212> TYPE: DNA
<213> ORGANISM: Artificial
<220> FEATURE:
<223> OTHER INFORMATION: PCR primer

<400> SEQUENCE: 49
cacccctgca tcctgcaatt tcaca                                        25

<210> SEQ ID NO 50
<211> LENGTH: 25
<212> TYPE: DNA
<213> ORGANISM: Artificial
<220> FEATURE:
<223> OTHER INFORMATION: PCR primer

<400> SEQUENCE: 50
actaacgcaa gcaggtccag ctccc                                        25
```

GENETICALLY MODIFIED NON-HUMAN ANIMAL WITH HUMAN OR CHIMERIC CD137

CLAIM OF PRIORITY

This application is a continuation of and claims priority to international Application No. PCT/CN2017/120388, filed on Dec. 30, 2017, which claims the benefit of Chinese Patent Application App. No. 201611256707.4, filed on Dec. 30, 2016, Chinese Patent Application App. No. 201710873061.2, filed on Sep. 25, 2017, and Chinese Patent Application App. No. 201711473251.1, filed on Dec. 29, 2017. The entire contents of the foregoing are incorporated herein by reference.

TECHNICAL FIELD

This disclosure relates to genetically modified animal expressing human or chimeric (e.g., humanized) CD137, and methods of use thereof.

BACKGROUND

The immune system has developed multiple mechanisms to prevent deleterious activation of T cells. One such mechanism is the intricate balance between positive and negative costimulatory signals delivered to T cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human CD137 or chimeric CD137. The animal model can express human CD137 or chimeric CD137 (e.g., humanized CD137) protein in its body. It can be used in the studies on the function of CD137 gene, and can be used in the screening and evaluation of anti-human CD137 antibodies. In addition, the animal models prepared by the methods described herein can be used in drug screening, pharmacodynamics studies, treatments for immune-related diseases (e.g., autoimmune disease), and cancer therapy for human CD137 target sites; they can also be used to facilitate the development and design of new drugs, and save time and cost. In summary, this disclosure provides a powerful tool for studying the function of CD137 protein and a platform for screening cancer drugs.

The disclosure also provides CD137 gene knockout mice. In addition, the mice described in the present disclosure can be mated with the mice containing other human or chimeric genes (e.g., chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy. In one aspect, the disclosure relates to genetically-modified, non-human animals whose genome comprises at least one chromosome comprising a sequence encoding a human or chimeric CD137. In some embodiments, the sequence encoding the human or chimeric CD137 is operably linked to an endogenous regulatory element at the endogenous CD137 gene locus in the at least one chromosome. In some embodiments, the sequence encoding a human or chimeric CD137 comprises a sequence encoding an amino acid sequence that is at least 50%, 55%, 65%, 70%, 75%, 80%, 85%, 90%, 95%, 99%, or 100% identical to human CD137 (NP_001552.2 (SEQ ID NO: 18)). In some embodiments, the sequence encoding a human or chimeric CD137 comprises a sequence encoding an amino acid sequence that is at least 50%, 55%, 65%, 70%, 75%, 80%, 85%, 90%, 95%, 99%, or 100% identical to SEQ ID NO: 24. In some embodiments, the sequence encoding a human or chimeric CD137 comprises a sequence encoding an amino acid sequence that corresponds to amino acids 1-184 of SEQ ID NO: 18.

In some embodiments, the animal is a mammal, e.g., a monkey, a rodent or a mouse. In some embodiments, the animal is a C57BL/6 mouse. In some embodiments, the animal does not express endogenous CD137. In some embodiments, the animal has one or more cells expressing human or chimeric CD137. In some embodiments, the expressed human or chimeric CD137 can bind to or interact with human protein CD137L (also known as 4-1BB Ligand or 4-1BBL). In some embodiments, the expressed human or chimeric CD137 can bind to or interact with endogenous CD137L.

In one aspect, the disclosure relates to genetically-modified, non-human animals, wherein the genome of the animals comprises a replacement, at an endogenous CD137 gene locus, of a sequence encoding a region of endogenous CD137 with a sequence encoding a corresponding region of human CD137. In some embodiments, the sequence encoding the corresponding region of human CD137 is operably linked to an endogenous regulatory element at the endogenous CD137 locus, and one or more cells of the animal expresses a chimeric CD137. In some embodiments, the animal does not express endogenous CD137. In some embodiments, the locus of endogenous CD137 is the extracellular region of CD137. In some embodiments, the animal has one or more cells expressing a chimeric CD137 having an extracellular region, a transmembrane region, and a cytoplasmic region, wherein the extracellular region comprises a sequence that is at least 50%, 60%, 70%, 80%, 90%, 95%, or 99% identical to the extracellular region of human CD137. In some embodiments, the extracellular region of the chimeric CD137 has a sequence that has at least 10, 20, 30, 40, 50, 60, 70, 80, 90, 100, 110, 120, 130, 140, 150, 160, 170, or 180 contiguous amino acids that are identical to a contiguous sequence present in the extracellular region of human CD137. In some embodiments, the animal is a mouse, and the sequence encoding the region of endogenous CD137 is exon 2, exon 3, exon 4, exon 5, exon 6, exon 7, and/or exon 8 of the endogenous mouse CD137 gene. In some embodiments, the animal is heterozygous with respect to the replacement at the endogenous CD137 gene locus. In some embodiments, the animal is homozygous with respect to the replacement at the endogenous CD137 gene locus.

In one aspect, the disclosure relates to methods for making a genetically-modified, non-human animal. The methods involve replacing in at least one cell of the animal, at an endogenous CD137 gene locus, a sequence encoding a region of an endogenous CD137 with a sequence encoding a corresponding region of human CD137. In some embodiments, the sequence encoding the corresponding region of human CD137 comprises exon 3, exon 4, exon 5, exon 6, exon 7, exon 8, and/or exon 9 of a human CD137 gene. In some embodiments, the sequence encoding the corresponding region of CD137 comprises exon 3, exon 4, exon 5, exon 6, exon 7, and/or exon 8 (or part thereof, e.g., part of exon 8) of a human CD137 gene. In some embodiments, the sequence encoding the corresponding region of human CD137 encodes amino acids 1-184 of SEQ ID NO: 18. In some embodiments, the region is located within the extracellular region of CD137. In some embodiments, the animal is a mouse, and the sequence encoding the region of the endogenous CD137 locus is exon 2, exon 3, exon 4, exon 5, exon 6, exon 7, and/or exon 8 of mouse CD137 gene (e.g., exon 2, exon 3, exon 4, exon 5, exon 6, and part of exon 7).

In one aspect, the disclosure relates to non-human animals comprising at least one cell comprising a nucleotide sequence encoding a chimeric CD137 polypeptide, wherein the chimeric CD137 polypeptide comprises at least 50 contiguous amino acid residues that are identical to the corresponding contiguous amino acid sequence of a human CD137, wherein the animal expresses the chimeric CD137. In some embodiments, the chimeric CD137 polypeptide has at least 50 contiguous amino acid residues that are identical to the corresponding contiguous amino acid sequence of a human CD137 extracellular region. In some embodiments, the chimeric CD137 polypeptide comprises a sequence that is at least 90%, 95%, or 99% identical to amino acids 1-184 of SEQ ID NO: 18. In some embodiments, the nucleotide sequence is operably linked to an endogenous CD137 regulatory element of the animal. In some embodiments, the chimeric CD137 polypeptide comprises an endogenous CD137 transmembrane region and/or an endogenous CD137 cytoplasmic region. In some embodiments, the nucleotide sequence is integrated to an endogenous CD137 gene locus of the animal. In some embodiments, the chimeric CD137 has at least one mouse CD137 activity (e.g., interacting with mouse CD137L, and promoting immune responses in mice) and/or at least one human CD137 activity (e.g., interacting with human CD137L, and promoting immune responses in human).

In one aspect, the disclosure relates to methods of making a genetically-modified mouse cell that expresses a chimeric CD137, the method including: replacing, at an endogenous mouse CD137 gene locus, a nucleotide sequence encoding a region of mouse CD137 with a nucleotide sequence encoding a corresponding region of human CD137, thereby generating a genetically-modified mouse cell that includes a nucleotide sequence that encodes the chimeric CD137, wherein the mouse cell expresses the chimeric CD137. In some embodiments, the chimeric CD137 comprises a signal peptide sequence (e.g., a mouse signal peptide sequence or a human signal peptide sequence), an extracellular region of mouse CD137, an extracellular region of human CD137, a transmembrane and/or a cytoplasmic region of a mouse CD137. In some embodiments, the nucleotide sequence encoding the chimeric CD137 is operably linked to an endogenous CD137 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, T-Cell Immunoreceptor With Ig And ITIM Domains (TIGIT), Glucocorticoid-Induced TNFR-Related Protein (GITR), T-cell immunoglobulin and mucin-domain containing-3 (TIM-3), or TNF Receptor Superfamily Member 4 (TNFRSF4 or OX40).

In one aspect, the disclosure relates to methods of determining effectiveness of an anti-CD137 antibody for the treatment of cancer, including: administering the anti-CD137 antibody to the animal as described herein, wherein the animal has a tumor, and determining the inhibitory effects of the anti-CD137 antibody to the tumor. In some embodiments, the animal has one or more cells (e.g., antigen presenting cells (APC)) that express CD137L. In some embodiments, the animal has one or more tumor cells (e.g., tumor endothelial cells) that express CD137.

In some embodiments, the tumor comprises one or more cancer cells that are injected into the animal. In some embodiments, determining the inhibitory effects of the anti-CD137 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or refractory solid tumor cells. In some embodiments, the tumor cells are lymphoma cells, colorectal cancer cells, or oropharyngeal cancer cells. In some embodiments, the animal has metastatic solid tumors, NSCLC, melanoma, lymphoma (e.g., non-Hodgkin lymphoma), colorectal cancer, or multiple myeloma.

In one aspect, the disclosure relates to methods of determining effectiveness of an anti-CD137 antibody for the treatment of various immune-related disorders, e.g., autoimmune diseases.

In one aspect, the disclosure relates to methods of determining effectiveness of an anti-CD137 antibody and an additional therapeutic agent for the treatment of a tumor, including administering the anti-CD137 antibody and the additional therapeutic agent to the animal as described herein, wherein the animal has a tumor, and determining the inhibitory effects on the tumor. In some embodiments, the animal or mouse further comprises a sequence encoding an additional human or chimeric protein. In some embodiments, the additional human or chimeric protein is PD-1, CTLA-4, LAG-3, BTLA, PD-L1, CD27, CD28, CD47, TIGIT, TIM-3, GITR, or OX40. In some embodiments, the animal further comprises a sequence encoding a human or chimeric PD-1, PD-L1, or CTLA-4.

In some embodiments, the additional therapeutic agent is an antibody (e.g., human antibody) the specifically binds to PD-1, CTLA-4, LAG-3, BTLA, PD-L1, CD27, CD28, CD47, TIGIT, TIM-3, GITR, OX40, CD20, EGFR, or CD319. In some embodiments, the additional therapeutic agent is an anti-PD-1 antibody (e.g., nivolumab), an anti- PD-L1 antibody, an anti-CTLA4 antibody (e.g., ipilimumab), an anti-CD20 antibody (e.g., rituximab), an anti-EGFR antibody (e.g., cetuximab), or an anti-CD319 antibody (e.g., elotuzumab).

In some embodiments, the animal comprises one or more cells (e.g., T cells, natural killer (NK) cells, neutrophils, and dendritic cells, or tumor endothelial cells) that express CD137. In some embodiments, the animal comprises one or more cells (e.g., APC cells) that express CD137L. In some embodiments, the tumor comprises one or more tumor cells that express PD-L1 or PD-L2. In some embodiments, the tumor comprises one or more tumor cells that express CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells). In some embodiments, the animal has metastatic solid tumors, NSCLC, melanoma, lymphoma (e.g., non-Hodgkin lymphoma), colorectal cancer, or multiple myeloma.

In one aspect, the disclosure relates to proteins comprising an amino acid sequence, wherein the amino acid sequence is one of the following: (a) an amino acid sequence set forth in SEQ ID NO: 24; (b) an amino acid sequence that is at least 90% identical to SEQ ID NO: 24; (c) an amino acid sequence that is at least 91%, 92%, 93%, 94%, 95%, 96%, 97%, 98%, or 99% identical to SEQ ID NO: 24; (d) an amino acid sequence that is different from the amino acid sequence set forth in SEQ ID NO: 24 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 24. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 22; (c) SEQ ID NO: 23; (d) a sequence that is at least 90% identical to SEQ ID NO: 22 or SEQ ID NO: 23; (e) a sequence that is at least 91%, 92%, 93%, 94%, 95%, 96%, 97%, 98%, or 99% identical to SEQ ID NO: 22; and (f) a sequence that is at least 91%, 92%, 93%, 94%, 95%, 96%, 97%, 98%, or 99% identical to SEQ ID NO: 23. In some embodiments, provided herein are cells comprising the nucleic acids disclosed herein. In some embodiments, provided herein are animals having the nucleic acids disclosed herein.

In one aspect, the disclosure relates to a targeting vector, including a) a DNA fragment homologous to the 5' end of a region to be altered (5' arm), which is selected from the CD137 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD137 gene genomic DNAs in the length of 100 to 10,000 nucleotides.

In some embodiments, a) the DNA fragment homologous to the 5' end of a region to be altered (5' arm) is selected from the nucleotide sequences that have at least 90% homology to the NCBI accession number NC_000070.6; c) the DNA fragment homologous to the 3' end of the region to be altered (3' arm) is selected from the nucleotide sequences that have at least 90% homology to the NCBI accession number NC_000070.6.

In some embodiments, a) the DNA fragment homologous to the 5' end of a region to be altered (5' arm) is selected from the nucleotides from the position 150924999 to the position 150929845 of the NCBI accession number NC_000070.6; c) the DNA fragment homologous to the 3' end of the region to be altered (3' arm) is selected from the nucleotides from the position 150935815 to the position 150940542 of the NCBI accession number NC_000070.6.

In some embodiments, a length of the selected genomic nucleotide sequence is about 3 kb, 3.5 kb, 4 kb, 4.5 kb, or 5 kb. In some embodiments, the length is about 4847 bp or 4728 bp. In some embodiments, the region to be altered is exon 2, exon 3, exon 4, exon 5, exon 6, and/or exon 7 of mouse CD137 gene.

In some embodiments, the sequence of the 5' arm is shown in SEQ ID NO: 19. In some embodiments, the sequence of the 3' arm is shown in SEQ ID NO: 20.

In some embodiments, the targeting vector further includes a selectable gene marker.

In some embodiments, the target region is derived from human. In some embodiments, the target region is a part or entirety of the nucleotide sequence of a humanized CD137. In some embodiments, the nucleotide sequence is shown as one or more of exon 3, exon 4, exon 5, exon 6, exon 7, and exon 8 of the human CD137.

In some embodiments, the nucleotide sequence of the human CD137 encodes the human CD137 protein with the NCBI accession number NP_001552.2 (SEQ ID NO: 18). In some emboldens, the nucleotide sequence of the human CD137 is selected from the nucleotides from the position 7939994 to the position 7933289 of NC_000001.11 (SEQ ID NO: 21).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a CD137 gene humanized animal model to obtain a CD137 gene genetically modified humanized mouse;

(b) mating the CD137 gene genetically modified humanized mouse obtained in step (a) with another humanized mouse, and then screening to obtain a double humanized mouse model.

In some embodiments, in step (b), the CD137 gene genetically modified humanized mouse obtained in step (a) is mated with a PD-1 or PD-L1 humanized mouse to obtain a CD137 and PD-1 double humanized mouse model or a CD137 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD137 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD137 amino acid sequence of a humanized mouse, wherein the amino acid sequence is selected from the group consisting of:

a) an amino acid sequence shown in SEQ ID NO: 24;
b) an amino acid sequence having a homology of at least 90% with the amino acid sequence shown in SEQ ID NO: 24;
c) an amino acid sequence encoded by a nucleic acid sequence, wherein the nucleic acid sequence is able to hybridize to a nucleotide sequence encoding the amino acid shown in SEQ ID NO: 24 under a low stringency condition or a strict stringency condition;
d) an amino acid sequence having a homology of at least 90%, 91%, 92%, 93%, 94%, 95%, 96%, 97%, 98%, or at least 99% with the amino acid sequence shown in SEQ ID NO: 24;
e) an amino acid sequence that is different from the amino acid sequence shown in SEQ ID NO: 24 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 24.

The disclosure also relates to a CD137 nucleic acid sequence of a humanized mouse, wherein the nucleic acid sequence is selected from the group consisting of:

a) a nucleic acid sequence that encodes the CD137 amino acid sequence of a humanized mouse;
b) a nucleic acid sequence that is set forth in SEQ ID NO: 23;
c) a nucleic acid sequence having a coding DNA sequence (CDS) as shown in SEQ ID NO: 22;
d) a nucleic acid sequence that can hybridize to the nucleotide sequence as shown in SEQ ID NO: 22 or SEQ ID NO: 23 under a low stringency condition or a strict stringency condition;
e) a nucleic acid sequence that has a homology of at least 90%, 91%, 92%, 93%, 94%, 95%, 96%, 97%, 98%, or at least 99% with the nucleotide sequence as shown in SEQ ID NO: 22 or SEQ ID NO: 23;
f) a nucleic acid sequence that encodes an amino acid sequence, wherein the amino acid sequence has a homology of at least 90% with the amino acid sequence shown in SEQ ID NO: 24;
g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 24;
h) a nucleic acid sequence that encodes an amino acid sequence, wherein the amino acid sequence is different from the amino acid sequence shown in SEQ ID NO: 24 by no more than 10, 9, 8, 7, 6, 5, 4, 3, 2 or no more than 1 amino acid; and/or
i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 24.

The disclosure further relates to a CD137 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD137 gene function, human CD137 antibodies, the drugs or efficacies for human CD137 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

In FIGS. 17A-17B, M indicates the marker, + indicates a positive control mouse that is heterozygous for humanized CD137, and − indicates a wildtype control mouse; In FIGS. 17C-17D, WT indicates wildtype mouse; +/− indicates a control mouse that is heterozygous for humanized PD-1; and −/− indicates a control mouse that is homozygous for humanized PD-1.

FIGS. 18A and 18D show the results of a C57BL/6 wildtype mouse without anti-CD3 antibody stimulation. FIGS. 18B and 18E show the results of a C57BL/6 wildtype mouse with anti-CD3 antibody stimulation. FIGS. 18C and 18F show the results of a humanized mouse that is homozygous for both humanized CD137 and humanized PD-1 with anti-CD3 antibody stimulation. The cells were stained with 1) antibody against mouse CD137 (m4-1BB APC) and antibody against mouse TcRβ (mTcRβ PerCP) (FIGS. 18A-18C); and 2) antibody against human CD137 (h4-1BB PE), and antibody against mouse TcRβ (mTcRβ PerCP) (FIGS. 18D-18F).

FIGS. 19A and 19D show the results of a C57BL/6 wildtype mouse without anti-CD3 antibody stimulation. FIGS. 19B and 19E show the results of a C57BL/6 wildtype mouse with anti-CD3 antibody stimulation. FIGS. 19C and 19F show the results of a humanized mouse that is homozygous for both humanized CD137 and humanized PD-1 with anti-CD3 antibody stimulation. The cells were stained with 1) antibody against mouse PD-1 (mPD-1 PE) and antibody against mouse TcRβ (mTcRβ PerCP) (FIGS. 19A-19C); and 2) antibody against human PD-1 (hPD-1 FITC), and antibody against mouse TcRβ (mTcRβ PerCP) (FIGS. 19D-19F).

In FIGS. 22A-22B, M indicates the marker, − indicates a control wildtype mouse, and + indicates a positive control mouse that is homozygous for humanized CD137; In FIGS. 22C-22D, M indicates the marker, − indicates a control wildtype mouse, and + indicates a positive control mouse that is heterozygous for humanized PD-L1.

FIG. 23 shows the alignment between mouse CD137 amino acid sequence (NP_035742.1; SEQ ID NO: 16) and human CD137 amino acid sequence (NP_001552.2; SEQ ID NO: 18).

DETAILED DESCRIPTION

Figure 1:
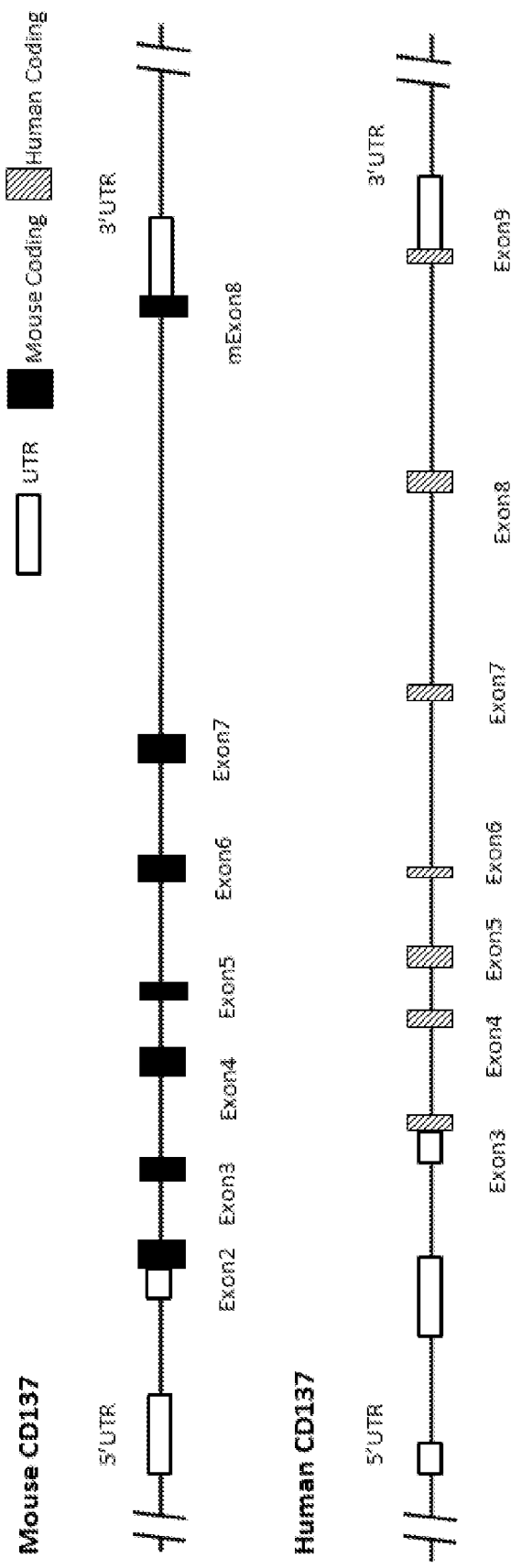
FIG. 1 is a schematic diagram showing human and mouse CD137 genes.

This disclosure relates to transgenic non-human animal with human or chimeric (e.g., humanized) CD137, and methods of use thereof.

CD137 (also known as tumor necrosis factor receptor superfamily member 9, TNFRSF9, or 4-1BB) is a member of the tumor necrosis factor (TNF) receptor family. CD137 are expressed on activated T cells, dendritic cells, B cells, follicular dendritic cells, natural killer cells, and granulocytes. It is known as a costimulatory receptor for activated T cells. Activation of CD137 can enhance T cell proliferation, IL-2 secretion, T cell survival and/or cytolytic activity.

Certain anti-CD137 antibodies can activate T-cells and promote immune response. These antibodies (e.g., Utomilumab or Urelumab (BMS-663513)) can be used to treat various cancers, e.g., lymphoma (e.g., non-Hodgkin lymphoma, follicular lymphoma, diffuse large B-Cell lymphoma, relapsed/refractory CD20+ Non-Hodgkin's lymphoma), advanced/metastatic solid tumors, colorectal cancer, neoplasms, malignant neoplasms of digestive organs, malignant neoplasms of lip oral cavity and pharynx, malignant neoplasms of bone and articular cartilage, malignant neoplasm of breast, breast carcinoma (e.g., HER2 Positive Breast Carcinoma, recurrent breast carcinoma, Stage III breast cancer), ovarian cancer, and/or oropharyngeal cancer. However, not all antibodies have similar effects. Some anti-CD137 antibodies may disrupt the interaction of CD137 and its ligand, and inhibit immune response instead.

Experimental animal models are an indispensable research tool for studying the effects of these antibodies. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD137

CD137 (4-1BB) is a member of the tumor necrosis factor (TNF) receptor family. It has three N-glycosylation sites and one potential O-glycosylation site. It is a type I transmembrane protein, and is mainly expressed on the surface of T cells, natural killer (NK) cells, neutrophils, and dendritic cells (DC) cells. The human CD137 gene is located on 1P36 region (chromosome 1) with NCBI gene ID 3604, and encodes 255 amino acids. The human CD137 protein molecule has two forms: membrane-bound and soluble, encoded by the 2.8 kb and 1.4 kb mRNAs, respectively. The soluble form does not have the transmembrane domain. The ligand for CD137 is CD137L (4-1BBL). CD137L belongs to the TNF superfamily and is expressed on the surface of antigen presenting cells, including e.g., dendritic cells, B cells, and macrophages. The synergistic stimulatory signal produced by the interaction of CD137 and its receptor CD137L induces activation and proliferation of T cells and NK cells, and the production of cytokines.

The mouse CD137 gene is located on 4E2 region (chromosome 4) with the NCBI gene ID 21942. Human CD137 protein is about 58% identical to mouse CD137 protein (FIG. 23). Human CD137 contains notable differences in its cytoplasmic tail from mouse CD137. In particular, the single tyrosine residue in the cytoplasmic domain of CD137 is found at position 220 of human CD137 and at position 254 of mouse CD137. Human CD137 also diverges from mouse CD137 at the putative Lck binding site, with mouse CD137 expressing the CXCP Lck binding motif, whereas in human CD137 this sequence is altered to CXFP. Both human and mouse CD137 have in common two sites for binding TNFR-associated factor 2, an adaptor protein that is essential for mediating downstream signaling events leading to cytokine (e.g., IL-2) production in response to CD137L signaling.

The abnormal expression of CD137 and its ligand in tumor tissue indicates that CD137 and its ligand may have co-stimulatory signal disruption or inactivation during tumorigenesis. Particularly, CD137 expression in tumor vessel walls is correlated with tumor malignancy, and evidence shows that agonist anti-CD137 antibody can act on tumor endothelial cells to enhance recruitment of activated T lymphocytes, which suggests an additional mechanism of action that can explain the immunotherapeutic effects of agonist CD137 antibodies.

A large number of studies have shown that CD137 is one of the potential targets for antitumor biological therapy. Anti-CD137 antibody can kill tumor cells or inhibit tumor growth probably by inducing activation and proliferation of T cells and NK cells, increasing the production of cytokines, upregulating the immune response, and/or recruiting activated T lymphocytes to the tumor. To date, two antibodies to the CD137 pathway (Urelumab (BMS-663513) from Bristol-Myers Squibb and Utomilumab (PF-05082566) from Pfizer) have been tested in clinical trials for treating melanoma, lymphoma, non-Hodgkin lymphoma and some advanced solid tumor. Some clinical trials already have promising preliminary clinical results. For example, PF-05082566 can reduce 40% of follicular lymphomas (FL) with minimal side effects similar to PD-1 inhibitors; it has been used in combination with other drugs, including e.g., anti-PD-1 antibody, or anti-OX40 antibody. Preliminary experimental evidence also shows that cancer-targeting drugs can increase the expression of CD137 on the surface of NK cells. Thus, if anti-CD137 antibody is administered in combination with cancer-targeting drugs, it can enhance the killing effect of NK cells and improve the therapeutic effect. However, despite the antitumor activity, trials using BMS-663513 to treat non-small cell lung cancer (NSCLC) have been terminated due to severe hepatotoxicity.

A detailed description of CD137 and its function can be found, e.g., in Wen et al., "4-1BB ligand-mediated costimulation of human T cells induces CD4 and CD8 T cell expansion, cytokine production, and the development of cytolytic effector function," The Journal of Immunology 168.10 (2002): 4897-4906; Broll et al., "CD137 expression in tumor vessel walls: high correlation with malignant tumors," American journal of clinical pathology 115.4 (2001): 543-549; and Palazón et al., "Agonist anti-CD137 mAb act on tumor endothelial cells to enhance recruitment of activated T lymphocytes," Cancer research 71.3 (2011): 801-811; each of which is incorporated by reference in its entirety.

In human genomes, CD137 gene (Gene ID: 3604) locus has nine exons, exon 1, exon 2, exon 3, exon 4, exon 5, exon 6, exon 7, exon 8, and exon 9 (FIG. 1). Among them, exon 1 and exon 2 do not encode amino acid sequences of CD137 protein. Only part of exon 3, exons 4-8, and part of exon 9 encode amino acid sequence of CD137 protein.

The CD137 protein also has an extracellular region, a transmembrane region, and a cytoplasmic region, and the signal peptide is located at the extracellular region of CD137. The nucleotide sequence for human CD137 mRNA is NM_001561.5 (SEQ ID NO: 17), and the amino acid sequence for human CD137 is NP_001552.2 (SEQ ID NO: 18). The location for each exon and each region in human CD137 nucleotide sequence and amino acid sequence is listed below:

TABLE 1

| Human CD137 (approximate location) | NM_001561.5 6001bp (SEQ ID NO: 17) | NP_001552.2 255aa (SEQ ID NO: 18) |
| --- | --- | --- |
| Exon 1 | 1-27 | Non-coding |
| Exon 2 | 28-177 | Non-coding |
| Exon 3 | 178-361 | 1-33 |
| Exon 4 | 362-469 | 34-69 |
| Exon 5 | 470-607 | 70-115 |
| Exon 6 | 608-674 | 116-138 |
| Exon 7 | 675-805 | 139-181 |
| Exon 8 | 806-940 | 182-226 |
| Exon 9 | 941-5993 | 227-255 |
| Signal peptide | 262-330 | 1-23 |
| Extracellular region (excluding signal peptide region) | 331-819 | 24-186 |
| Transmembrane region | 820-900 | 187-213 |
| Cytoplasmic region | 901-1026 | 214-255 |
| Donor region | 262-813 | 1-184 |

In mice, CD137 gene locus has eight exons, exon 1, exon 2, exon 3, exon 4, exon 5, exon 6, exon 7 and exon 8 (FIG. 1). Among them, exon 1 does not encode amino acid sequence of mouse CD137 protein. The mouse CD137 protein also has an extracellular region, a transmembrane region, and a cytoplasmic region, and the signal peptide is located at the extracellular region of CD137. The nucleotide sequence for mouse CD137 cDNA is NM_011612.2 (SEQ ID NO: 15), the amino acid sequence for mouse CD137 is NP_035742.1 (SEQ ID NO: 16). The location for each exon and each region in the mouse CD137 nucleotide sequence and amino acid sequence is listed below:

TABLE 2

| Mouse CD137 (approximate location) | NM_011612.2 2134bp (SEQ ID NO: 15) | NP_035742.1 256 aa (SEQ ID NO: 16) |
| --- | --- | --- |
| Exon 1 | 1-106 | Non-coding |
| Exon 2 | 107-231 | 1-33 |
| Exon 3 | 232-336 | 34-68 |
| Exon 4 | 337-474 | 69-114 |
| Exon 5 | 475-544 | 115-138 |
| Exon 6 | 545-669 | 139-179 |
| Exon 7 | 670-804 | 180-224 |
| Exon 8 | 805-2134 | 225-256 |
| Signal peptide | 132-200 | 1-23 |
| Extracellular region (excluding signal peptide region) | 201-692 | 24-187 |
| Transmembrane region | 693-755 | 188-208 |
| Cytoplasmic region | 756-899 | 209-256 |
| Replaced region in Example | 132-680 | 1-183 |

The mouse CD137 gene (Gene ID: 21942) is located in Chromosome 4 of the mouse genome, which is located from 150920155 to 150946104, of NC_000070.6 (GRCm38.p4 (GCF_000001635.24)). The 5'-UTR is from 150,920,190 to 150,920,260 and 150,929,821 to 150,929,845, exon 1 is from 150,920,190 to 150,920,260, the first intron is from 150,920,261 to 150,929,820, exon 2 is from 150,929,821 to 150,929,945, the second intron is from 150,929,946 to 150,930,728, exon 3 is from 150,930,729 to 150,930,833, the third intron is from 150,930,834 to 150,932,307, exon 4 is from 150,932,308 to 150,932,445, the fourth intron is from 150,932,446 to 150,933,032, exon 5 is from 150,933,033 to 150,933,102, the fifth intron is from 150,933,103 to 150,934,286, exon 6 is from 150,934,287 to 150,934,411, the sixth intron is from 150,934,412 to 150,935,421, exon 7 is from the 150,935,422 to 150,935,556, the seventh intron is from 150,935,557 to 150,944,772, exon 8 is from the 150,944,773 to 150,946,102, and 3'-UTR is from 150,944,871 to 150,946,102, based on transcript NM_011612.2. All relevant information for mouse CD137 locus can be found in the NCBI website with Gene ID: 21942, which is incorporated by reference herein in its entirety.

FIG. 23 shows the alignment between mouse CD137 amino acid sequence (NP_035742.1; SEQ ID NO: 16) and human CD137 amino acid sequence (NP_001552.2; SEQ ID NO: 18). Thus, the corresponding amino acid residue or region between human and mouse CD137 can also be found in FIG. 23. In addition, exon 1 in mouse CD137 gene, and exon 1 and exon 2 in human CD137 gene are non-coding sequences. Thus, exon 2 in mouse approximately corresponds to exon 3 in human, exon 3 in mouse approximately corresponds to exon 4 in human, exon 4 in mouse approximately corresponds to exon 5 in human, exon 5 in mouse approximately corresponds to exon 6 in human, exon 6 in mouse approximately corresponds to exon 7 in human, exon 7 in mouse approximately corresponds to exon 8 in human, and exon 8 in mouse approximately corresponds to exon 9 in human.

CD137 genes, proteins, and locus of the other species are also known in the art. For example, the gene ID for CD137 in *Rattus norvegicus* is 500590, the gene ID for CD137 in *Macaca mulatta* (Rhesus monkey) is 708281, the gene ID for CD137 in *Canis lupus familiaris* (dog) is 608274, and the gene ID for CD137 in *Cavia porcellus* (domestic guinea pig) is 100730923. The relevant information for these genes (e.g., intron sequences, exon sequences, amino acid residues of these proteins) can be found, e.g., in NCBI database.

The present disclosure provides human or chimeric (e.g., humanized) CD137 nucleotide sequence and/or amino acid sequences. In some embodiments, the entire sequence of mouse exon 1, exon 2, exon 3, exon 4, exon 5, exon 6, exon 7, exon 8, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, exon 8, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, signal peptide, extracellular region, transmembrane region, or cytoplasmic region. In some embodiments, a region, a portion, or the entire sequence of mouse exon 2, exon 3, exon 4, exon 5, exon 6, exon 7, and/or exon 8 (e.g., exon 2, exon 3, exon 4, exon 5, exon 6, exon 7) are replaced by the human exon 3, exon 4, exon 5, exon 6, exon 7, exon 8, and/or exon 9 (e.g., exon 3, exon 4, exon 5, exon 6, exon 7, exon 8) sequence.

In some embodiments, the present disclosure also provides a chimeric (e.g., humanized) CD137 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD137 mRNA sequence (e.g., SEQ ID NO: 15), mouse CD137 amino acid sequence (e.g., SEQ ID NO: 16), or a portion thereof (e.g., exon 2, exon 3, exon 4, exon 5, exon 6, and exon 7); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD137 mRNA sequence (e.g., SEQ ID NO: 17), human CD137 amino acid sequence (e.g., SEQ ID NO: 18), or a portion thereof (e.g., exon 3, exon 4, exon 5, exon 6, exon 7, exon 8).

In some embodiments, the sequence encoding amino acids 1-183 of mouse CD137 (SEQ ID NO: 16) is replaced. In some embodiments, the sequence is replaced by a sequence encoding a corresponding region of human CD137 (e.g., amino acids 1-184 of human CD137 (SEQ ID NO: 18).

In some embodiments, the nucleic acids as described herein are operably linked to a promotor or regulatory element, e.g., an endogenous mouse CD137 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD137 nucleotide sequence (e.g., exon 2, exon 3, exon 4, exon 5, exon 6, exon 7, or NM_011612.2 (SEQ ID NO: 15)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD137 nucleotide sequence (e.g., exon 2, exon 3, exon 4, exon 5, exon 6, exon 7, or NM_011612.2 (SEQ ID NO: 15)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD137 nucleotide sequence (e.g., exon 3, exon 4, exon 5, exon 6, exon 7, exon 8, or NM_001561.5 (SEQ ID NO: 17)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD137 nucleotide sequence (e.g., exon 3, exon 4, exon 5, exon 6, exon 7, exon 8, or NM_001561.5 (SEQ ID NO: 17)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD137 amino acid sequence (e.g., exon 2, exon 3, exon 4, exon 5, exon 6, exon 7, or NP_035742.1 (SEQ ID NO: 16)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD137 amino acid sequence (e.g., exon 2, exon 3, exon 4, exon 5, exon 6, exon 7, or NP_035742.1 (SEQ ID NO: 16)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD137 amino acid sequence (e.g., exon 3, exon 4, exon 5, exon 6, exon 7, exon 8, or NP_001552.2 (SEQ ID NO: 18)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD137 amino acid sequence (e.g., exon 3, exon 4, exon 5, exon 6, exon 7, exon 8, or NP_001552.2 (SEQ ID NO: 18)).

The present disclosure also provides a humanized CD137 mouse amino acid sequence, wherein the amino acid sequence is selected from the group consisting of: a) an amino acid sequence shown in SEQ ID NO: 24;

b) an amino acid sequence having a homology of at least 90% with or at least 90% identical to the amino acid sequence shown in SEQ ID NO: 24;

c) an amino acid sequence encoded by a nucleic acid sequence, wherein the nucleic acid sequence is able to hybridize to a nucleotide sequence encoding the amino acid shown in SEQ ID NO: 24 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 24;

e) an amino acid sequence that is different from the amino acid sequence shown in SEQ ID NO: 24 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 24.

The present disclosure also relates to a CD137 nucleic acid (e.g., DNA or RNA) sequence, wherein the nucleic acid sequence can be selected from the group consisting of:

a) a nucleic acid sequence as shown in SEQ ID NO: 22, or a nucleic acid sequence encoding a homologous CD137 amino acid sequence of a humanized mouse;

b) a nucleic acid sequence that is shown in SEQ ID NO: 23;

c) a nucleic acid sequence that is able to hybridize to the nucleotide sequence as shown in SEQ ID NO: 22 or SEQ ID NO: 23 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 22 or SEQ ID NO: 23;

e) a nucleic acid sequence that encodes an amino acid sequence, wherein the amino acid sequence has a homology of at least 90% with or at least 90% identical to the amino acid sequence shown in SEQ ID NO: 24;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 24;

g) a nucleic acid sequence that encodes an amino acid sequence, wherein the amino acid sequence is different from the amino acid sequence shown in SEQ ID NO: 24 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 24.

The present disclosure further relates to a CD137 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 22 or SEQ ID NO: 23.

The disclosure also provides an amino acid sequence that has a homology of at least 90% with, or at least 90% identical to the sequence shown in SEQ ID NO: 24, and has protein activity. In some embodiments, the homology with the sequence shown in SEQ ID NO: 24 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 24 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 23, and encodes a polypeptide that has protein activity. In some embodiments, the homology with the sequence shown in SEQ ID NO: 23 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 23 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of identical residues (percent identity) and the percentage of residues conserved with similar physicochemical properties (percent homology), e.g. leucine and isoleucine, can be used to measure sequence similarity. Residues conserved with similar physicochemical properties are well known in the art. The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) CD137 from an endogenous non-human CD137 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous CD137 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD137 gene or a humanized CD137 nucleic acid. In some embodiments, at least one or more portions of the gene or the nucleic acid is from the human CD137 gene, at least one or more portions of the gene or the nucleic acid is from a non-human CD137 gene. In some embodiments, the gene or the nucleic acid comprises a sequence that encodes a CD137 protein. The encoded CD137 protein is functional or has at least one activity of the human CD137 protein or the non-human CD137 protein, e.g., binding to human or non-human CD137L, inducing activation and proliferation of T cells and NK cells, increasing the production of cytokines, upregulating the immune response, and/or recruiting activated T lymphocytes to the tumor.

In some embodiments, the chimeric protein or the chimeric polypeptide is a humanized CD137 protein or a humanized CD137 polypeptide. In some embodiments, at least one or more portions of the amino acid sequence of the protein or the polypeptide is from a human CD137 protein, and at least one or more portions of the amino acid sequence of the protein or the polypeptide is from a non-human CD137 protein. The humanized CD137 protein or the humanized CD137 polypeptide is functional or has at least one activity of the human CD137 protein or the non-human CD137 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 129S4/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD137 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD137 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature CD137 coding sequence with human mature CD137 coding sequence.

Genetically modified non-human animals that comprise a modification of an endogenous non-human CD137 locus. In some embodiments, the modification can comprise a human nucleic acid sequence encoding at least a portion of a mature CD137 protein (e.g., at least 10%, 20%, 30%, 40%, 50%, 60%, 70%, 80%, 90%, 95%, 96%, 97%, 98%, or 99% identical to the mature CD137 protein sequence). Although genetically modified cells are also provided that can comprise the modifications described herein (e.g., ES cells, somatic cells), in many embodiments, the genetically modified non-human animals comprise the modification of the endogenous CD137 locus in the germline of the animal.

Genetically modified animals can express a human CD137 and/or a chimeric (e.g., humanized) CD137 from endogenous mouse loci, wherein the endogenous mouse CD137 gene has been replaced with a human CD137 gene and/or a nucleotide sequence that encodes a region of human CD137 sequence or an amino acid sequence that is at least 10%, 20%, 30%, 40%, 50%, 60%, 70&, 80%, 90%, 95%, 96%, 97%, 98%, or 99% identical to the human CD137 sequence. In various embodiments, an endogenous non-human CD137 locus is modified in whole or in part to comprise human nucleic acid sequence encoding at least one protein-coding sequence of a mature CD137 protein.

In some embodiments, the genetically modified mice express the human CD137 and/or chimeric CD137 (e.g., humanized CD137) from endogenous loci that are under control of mouse promoters and/or mouse regulatory elements. The replacement(s) at the endogenous mouse loci provide non-human animals that express human CD137 or chimeric CD137 (e.g., humanized CD137) in appropriate cell types and in a manner that does not result in the potential pathologies observed in some other transgenic mice known in the art. The human CD137 or the chimeric CD137 (e.g., humanized CD137) expressed in animal can maintain one or more functions of the wildtype mouse or human CD137 in the animal. For example, human or non-human CD137 ligands (e.g., CD137L) can bind to the expressed CD137 and upregulate immune response, e.g., upregulate immune response by at least 10%, 20%, 30%, 40%, or 50%. Furthermore, in some embodiments, the animal does not express endogenous CD137. As used herein, the term "endogenous CD137" refers to CD137 protein that is expressed from an endogenous CD137 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human CD137 (NP_001552.2) (SEQ ID NO: 18). In some embodiments, the genome comprises a sequence encoding an amino acid sequence that is at least 70%, 75%, 80%, 85%, 90%, 95%, 99%, or 100% identical to SEQ ID NO: 24.

The genome of the genetically modified animal can comprise a replacement at an endogenous CD137 gene locus of a sequence encoding a region of endogenous CD137 with a sequence encoding a corresponding region of human CD137. In some embodiments, the sequence that is replaced is any sequence within the endogenous CD137 gene locus, e.g., exon 1, exon 2, exon 3, exon 4, exon 5, exon 6, exon 7, exon 8, 5'-UTR, 3'UTR, the first intron, the second intron, and the third intron, the fourth intron, the fifth intron, the sixth intron, the seventh intron etc. In some embodiments, the sequence that is replaced is within the regulatory region of the endogenous CD137 gene. In some embodiments, the sequence that is replaced is exon 2, exon 3, exon 4, exon 5, exon 6, exon 7 or part thereof, of an endogenous mouse CD137 gene locus.

The genetically modified animal can have one or more cells expressing a human or chimeric CD137 (e.g., humanized CD137) having an extracellular region and a cytoplasmic region, wherein the extracellular region comprises a sequence that is at least 50%, 60%, 70%, 80%, 90%, 95%, 99% identical to the extracellular region of human CD137. In some embodiments, the extracellular region of the humanized CD137 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD137. Because human CD137 and non-human CD137 (e.g., mouse CD137) sequences, in many cases, are different, antibodies that bind to human CD137 will not necessarily have the same binding affinity with non-human CD137 or have the same effects to non-human CD137. Therefore, the genetically modified animal having a human or a humanized extracellular region can be used to better evaluate the effects of anti-human CD137 antibodies in an animal model. In some embodiments, the genome of the genetically modified animal comprises a sequence encoding an amino acid sequence that corresponds to part or the entire sequence of exon 3, exon 4, exon 5, exon 6, exon 7, and/or exon 8 of human CD137, part or the entire sequence of extracellular region of human CD137 (with or without signal peptide), or part or the entire sequence of amino acids 1-184 of SEQ ID NO: 18.

In some embodiments, the non-human animal can have, at an endogenous CD137 gene locus, a nucleotide sequence encoding a chimeric human/non-human CD137 polypeptide, wherein a human portion of the chimeric human/non-human CD137 polypeptide comprises a portion of human CD137 extracellular domain, and wherein the animal expresses a functional CD137 on a surface of a cell of the animal. The human portion of the chimeric human/non-human CD137 polypeptide can comprise a portion of exon 3, exon 4, exon 5, exon 6, exon 7, and/or exon 8 of human CD137. In some embodiments, the human portion of the chimeric human/non-human CD137 polypeptide can comprise a sequence that is at least 80%, 85%, 90%, 95%, or 99% identical to amino acids 1-184 of SEQ ID NO: 18.

In some embodiments, the non-human portion of the chimeric human/non-human CD137 polypeptide comprises transmembrane and/or cytoplasmic regions of an endogenous non-human CD137 polypeptide. There may be several advantages that are associated with the transmembrane and/or cytoplasmic regions of an endogenous non-human CD137 polypeptide. For example, once a CD137 ligand (e.g., CD137L) binds to CD137, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of CD137 are also derived from endogenous sequence. These amino acids can also be important for transmembrane signal transmission.

Furthermore, the genetically modified animal can be heterozygous with respect to the replacement at the endogenous CD locus, or homozygous with respect to the replacement at the endogenous CD locus.

In some embodiments, the humanized CD137 locus lacks a human CD137 5'-UTR. In some embodiment, the humanized CD137 locus comprises a rodent (e.g., mouse) 5'-UTR. In some embodiments, the humanization comprises a human 3'-UTR. In appropriate cases, it may be reasonable to presume that the mouse and human CD137 genes appear to be similarly regulated based on the similarity of their 5'-flanking sequence. As shown in the present disclosure, humanized CD137 mice that comprise a replacement at an endogenous mouse CD137 locus, which retain mouse regulatory elements but comprise a humanization of CD137 encoding sequence, do not exhibit pathologies. Both genetically modified mice that are heterozygous or homozygous for humanized CD137 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD137 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD137 in the genome of the animal.

Figure 2:
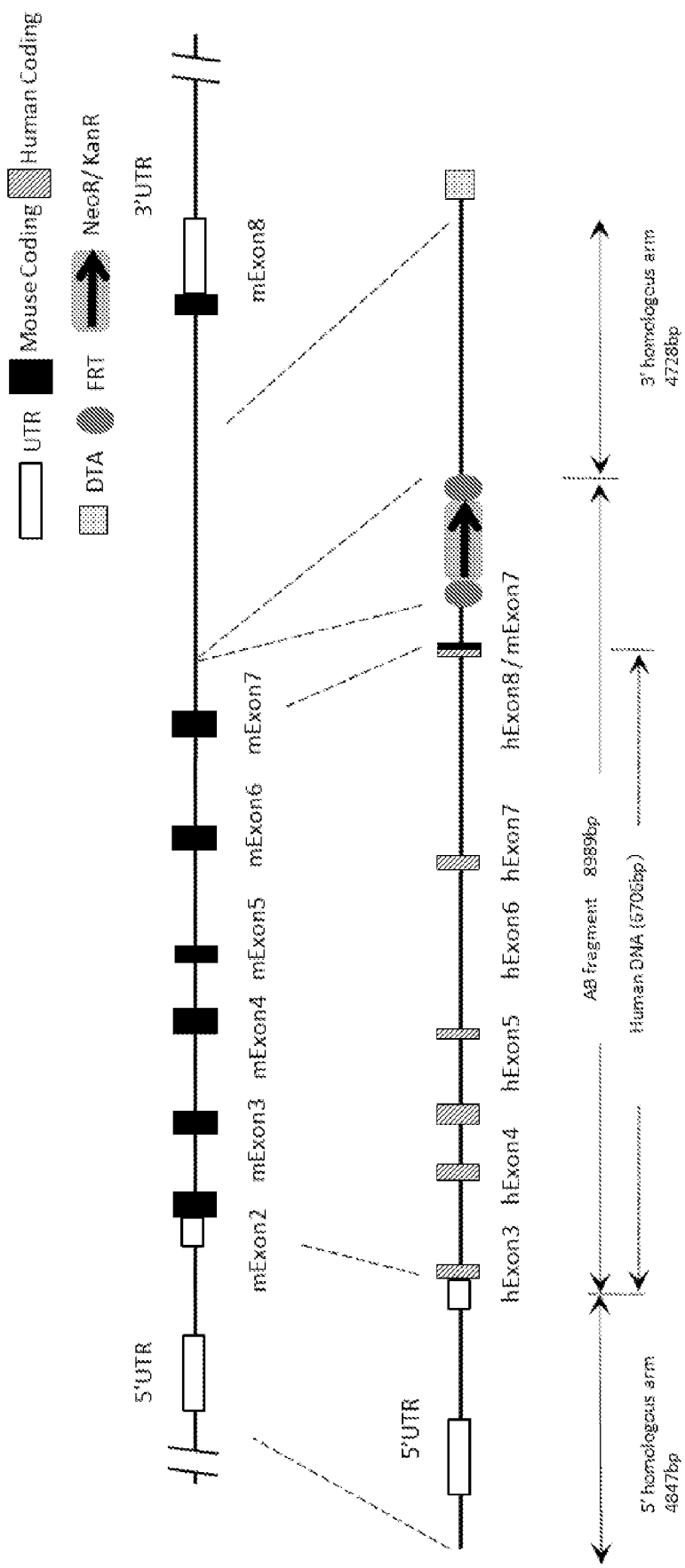
FIG. 2 is a schematic diagram showing mouse CD137 gene targeting strategy.
Figure 3:
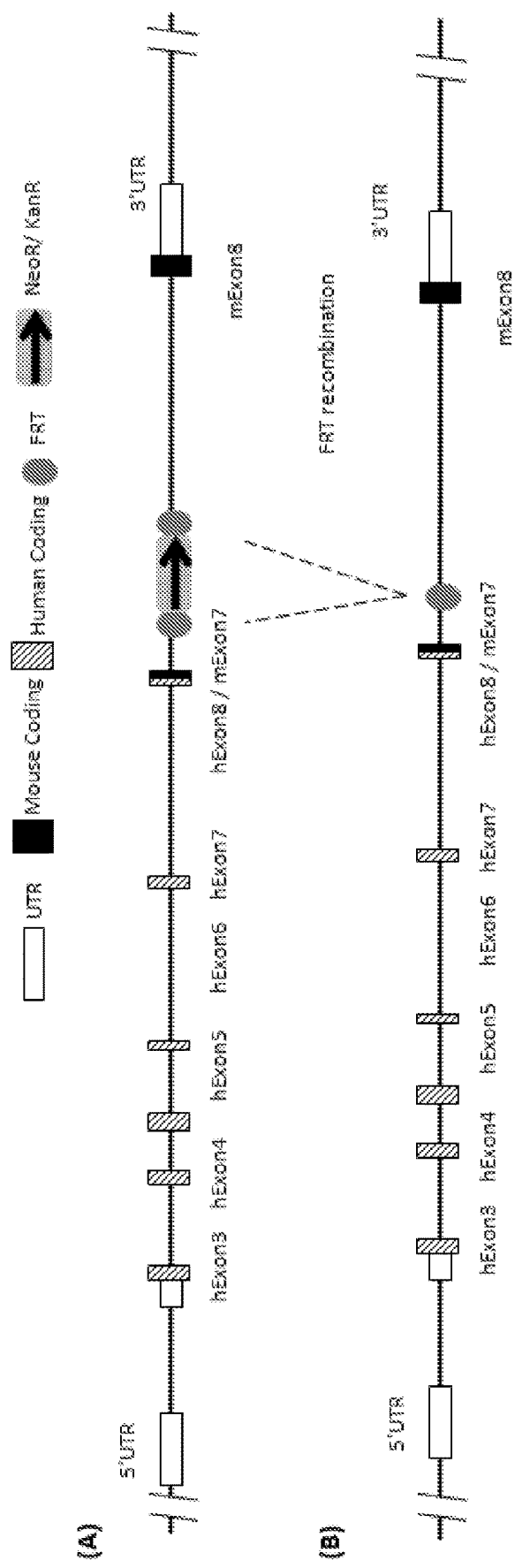
FIG. 3 is a schematic diagram showing humanized CD137 mouse gene map and FRT recombination.

In some embodiments, the non-human mammal comprises the genetic construct as described herein (e.g., gene construct as shown in FIG. 2 or FIG. 3). In some embodiments, a non-human mammal expressing human or humanized CD137 is provided. In some embodiments, the tissue-specific expression of human or humanized CD137 protein is provided.

In some embodiments, the expression of human or humanized CD137 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD137 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized CD137 protein.

Vectors

The present disclosure relates to a targeting vector, comprising: a) a DNA fragment homologous to the 5' end of a region to be altered (5' arm), which is selected from the CD137 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD137 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000070.6; c) the DNA fragment homologous to the 3' end of the region to be altered (3' arm) is selected from the nucleotide sequences that have at least 90% homology to the NCBI accession number NC_000070.6.

In some embodiments, a) the DNA fragment homologous to the 5' end of a region to be altered (5' arm) is selected from the nucleotides from the position 150924999 to the position 150929845 of the NCBI accession number NC_000070.6; c) the DNA fragment homologous to the 3' end of the region to be altered (3' arm) is selected from the nucleotides from the position 150935815 to the position 150940542 of the NCBI accession number NC_000070.6.

In some embodiments, the length of the selected genomic nucleotide sequence in the targeting vector can be about 3 kb, about 3.5 kb, about 4 kb, about 4.5 kb, or about 5 kb. In some embodiments, the length is about 4847 bp or about 4728 bp.

In some embodiments, the region to be altered is exon 1, exon 2, exon 3, exon 4, exon 5, exon 6, exon 7, and/or exon 8 of CD137 gene (e.g., exon 2, exon 3, exon 4, exon 5, exon 6, and/or exon 7 of mouse CD137 gene).

The targeting vector can further include a selected gene marker.

In some embodiments, the sequence of the 5' arm is shown in SEQ ID NO: 19; and the sequence of the 3' arm is shown in SEQ ID NO: 20.

In some embodiments, the sequence is derived from human (e.g., 7939994-7933289 of NC_000001.11). For example, the target region in the targeting vector is a part or entirety of the nucleotide sequence of a human CD137, preferably exon 3, exon 4, exon 5, exon 6, exon 7, and/or exon 8 of the human CD137. In some embodiments, the nucleotide sequence of the humanized CD137 encodes the entire or the part of human CD137 protein with the NCBI accession number NP_001552.2 (SEQ ID NO: 18).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD137 gene locus, a sequence encoding a region of an endogenous CD137 with a sequence encoding a corresponding region of human or chimeric CD137. In some embodiments, the replacement occurs in a germ cell, a somatic cell, a blastocyst, or a fibroblast, etc. The nucleus of a somatic cell or the fibroblast can be inserted into an enucleated oocyte.

FIG. 2 shows a humanization strategy for a mouse CD137 locus. In FIG. 2, the targeting strategy involves a vector comprising the 5' end homologous arm, human CD137 gene fragment, 3' homologous arm. The process can involve replacing endogenous CD137 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD137 sequence with human CD137 sequence.

Thus, in some embodiments, the methods for making a genetically modified, humanized animal, can include the step of replacing at an endogenous CD137 locus (or site), a nucleic acid encoding a sequence encoding a region of endogenous CD137 with a sequence encoding a corresponding region of human CD137. The sequence can include a region (e.g., a part or the entire region) of exon 1, exon 2, exon 3, exon 4, exon 5, exon 6, exon 7, exon 8, and/or exon 9 of a human CD137 gene. In some embodiments, the sequence includes a region of exon 3, exon 4, exon 5, exon 6, exon 7, and exon 8 of a human CD137 gene (e.g., amino acids 1-184 of SEQ ID NO: 18). In some embodiments, the region is located within the extracellular region of CD137. In some embodiments, the endogenous CD137 locus is exon 2, exon 3, exon 4, exon 5, exon 6, and/or exon 7 of mouse CD137.

In some embodiments, the methods of modifying a CD137 locus of a mouse to express a chimeric human/mouse CD137 peptide can include the steps of replacing at the endogenous mouse CD137 locus a nucleotide sequence encoding a mouse CD137 with a nucleotide sequence encoding a human CD137, thereby generating a sequence encoding a chimeric human/mouse CD137.

In some embodiments, the nucleotide sequence encoding the chimeric human/mouse CD137 can include a first nucleotide sequence encoding an extracellular region of mouse CD137 (with or without the mouse or human signal peptide sequence); a second nucleotide sequence encoding an extracellular region of human CD137; a third nucleotide sequence encoding a transmembrane and a cytoplasmic region of a mouse CD137.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD137 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD137 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized CD137, which are useful for testing agents that can decrease or block the interaction between CD137 and CD137L or the interaction between CD137 and other ligands, testing whether an agent can increase or decrease the immune response, and/or determining whether an agent is an CD137 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD137 antibody for the treatment of cancer. The methods involve administering the anti-CD137 antibody to the animal as described herein, wherein the animal has a tumor; and determining the inhibitory effects of the anti-CD137 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-CD137 antibody or anti-CD137L antibody prevents CD137L from binding to CD137. In some embodiments, the anti-CD137 antibody or anti-CD137L antibody does not prevent CD137L from binding to CD137.

In some embodiments, the genetically modified animals can be used for determining whether an anti-CD137 antibody is an CD137 agonist or antagonist. In some embodiments, the methods as described herein are also designed to determine the effects of the agent (e.g., anti-CD137 antibodies) on CD137, e.g., whether the agent can stimulate T cells or inhibit T cells, whether the agent can stimulate NK cells or inhibit NK cells, whether the agent can increase the production of cytokines, whether the agent can recruit activated T lymphocytes to the tumor, and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CD137 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD137 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-CD137 antibody is designed for treating hepatocellular, ovarian, colon, or cervical carcinomas. In some embodiments, the anti-CD137 antibody is designed for treating advanced breast cancer, advanced ovarian cancer, and/or advanced refractory solid tumor. In some embodiments, the anti-CD137 antibody is designed for treating metastatic solid tumors, NSCLC, melanoma, non-Hodgkin lymphoma, colorectal cancer, and multiple myeloma.

In some embodiments, the anti-CD137 antibody is designed for treating various autoimmune diseases. Thus, the methods as described herein can be used to determine the effectiveness of an anti-CD137 antibody in inhibiting immune response.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD137 gene function, human CD137 antibodies, drugs for human CD137 targeting sites, the drugs or efficacies for human CD137 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD137 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (TNFRSF4 or OX40).

The methods of generating genetically modified animal model with two or more human or chimeric genes (e.g., humanized genes) can include the following steps:

(a) using the methods of introducing human CD137 gene or chimeric CD137 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD47, TIGIT, TIM-3, GITR, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/117984; each of which is incorporated herein by reference in its entirety.

In some embodiments, the CD137 humanization is directly performed on a genetically modified animal having a human or chimeric PD-1, CTLA-4, BTLA, PD-L1, CD27, CD28, CD47, TIGIT, TIM-3, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD137 antibody and an additional therapeutic agent for the treatment of cancer. The methods include administering the anti-CD137 antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD28, CD47, TIGIT, TIM-3, GITR, or OX40. In some embodiments, the additional therapeutic agent is an anti-CTLA4 antibody (e.g., ipilimumab), an anti-CD20 antibody (e.g., rituximab), an anti-EGFR antibody (e.g., cetuximab), and an anti-CD319 antibody (e.g., elotuzumab), or anti-PD-1 antibody (e.g., nivolumab).

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

C57BL/6 mice and Flp recombinase transgenic mice were purchased from the China Food and Drugs Research Institute National Rodent Experimental Animal Center.

BALB/c mice were obtained from Beijing Vital River Laboratory Animal Technology Co., Ltd.

B-hPD-1 mice and B-hPD-L1 mice were obtained from Beijing Biocytogen Co., Ltd.

BAC clones were purchased from Invitrogen (Catalog number: RPCI-11.0 and RPCI-23.C).

Reverse Transcription Kit was obtained from Takara (Catalog number: 6110A).

AIO kit was obtained from Beijing Biocytogen Co., Ltd. (Catalog number: BCG-DX-004).

BamHI, XhoI, NotI, KpnI, BstZ17I, NdeI, SalI, and SmaI restriction enzymes were purchased from NEB (Catalog numbers: R3136M, R0146S, R3189M, R0142S, R3594S, R0111S, R3138M, and R0141S).

E. coli TOP10 competent cells were purchased from the Tiangen Biotech (Beijing) Co. (Catalog number: CB104-02).

Mouse colon cancer cells MC38 were purchased from Shanghai Enzyme Research Biotechnology Co., Ltd.

Anti-mouse CD137 (4-1BB) monoclonal antibody (17B5) APC ("mCD137 APC" or "m4-1BB APC") was purchased from eBioscience (Catalog number: 17-1371-82).

Anti-human CD137 (4-1BB) monoclonal antibody (4B4 (4B4-1)) PE ("hCD137 PE" or "h4-1BB PE") was purchased from eBioscience (Catalog number: 12-1379-42).

PerCP/Cy5.5 anti-mouse TCR β chain (mTcRβ PerCP) antibody was purchased from Biolegend (Catalog number: 109228).

PE anti-mouse CD279 (PD-1) (mPD-1 PE) antibody was purchased from Biolegend (Catalog number: 109104).

FITC anti-human CD279 (PD-1) antibody (hPD-1 FITC) was purchased from Biolegend (Catalog number: 329904).

APC anti-mouse CD274 (B7-H1, PD-L1) antibody (mPD-L1 APC) was purchased from Biolegend (Catalog number: 124312).

PE anti-human CD274 (B7-H1, PD-L1) antibody (hPD-L1 PE) was purchased from Biolegend (Catalog number: 329706).

G418 medium was purchased from Thermo Fisher (Catalog number: 11811023).

Mouse anti-CD3 antibody was obtained from BD (Catalog number: 563123).

Flow cytometer was purchased from BD Biosciences (model: FACS Calibur™).

Example 1: Primer Design and PCR Amplification

Primers for amplifying 7 homologous recombination fragments (A1, A2-1, A2-2, A3, B, C1, C2) were designed and the primer sequences are shown in the table below.

TABLE 3

| Fragments | Length (bp) | Primer sequence (5'-3') |
|---|---|---|
| A1 | 405bp | F: cgatggtaccagtactgtggaactgcttaaatatggttg (SEQ ID NO: 1)<br>R: ctatgttgtaacagctgtttcccatggcgaaatgtcacatgcacag (SEQ ID NO: 2) |
| A2-1 | 490bp | F: ctgtgcatgtgacatttcgccatgggaaacagctgttacaacatag (SEQ ID NO: 3)<br>R: agcggtggctcacacctgtatactcgctgctatgccccca (SEQ ID NO: 4) |
| A2-2 | 516bp | F: tgggggcatagcagcgagtatacaggtgtgagccaccgct (SEQ ID NO: 5)<br>R: aggaacaaggtaaggacctgcaaagagtgtcctgcaaaacacagc (SEQ ID NO: 6) |
| A3 | 414bp | F: gctgtgttttgcaggacactctttgcaggtccttaccttgttcct (SEQ ID NO: 7)<br>R: cgatctcgagcaatatccttgtgggagcaagc (SEQ ID NO: 8) |
| B | 455bp | F: cgatggatccaggcctgcaatgcctggaggcagttgtat (SEQ ID NO: 9)<br>R: cgatgcggccgcagtactaggctggggcctagcaaac (SEQ ID NO: 10) |
| C1 | 382bp | F: gctggtaccggcgcgcctcgaggtcagaatcccaaggacagcag (SEQ ID NO: 11)<br>R: gaggggttcttagatatcccgtgctgtttatccactc (SEQ ID NO: 12) |
| C2 | 425bp | F: acagcacgggatatctaagaacccctccctacgtc (SEQ ID NO: 13)<br>R: tcctcttcagacctggcggccgcgtcctctactctctacccagttttg (SEQ ID NO: 14) |

KOD-plus DNA polymerase was used to amplify the seven homologous recombination fragments. Among them, BAC clones with mouse CD137 (Catalog number: RPCI23.C, Clone ID:448J14; "mouse BAC clones") were used as a template for A1, A3, B, C1, C2 homologous recombination fragments, and BAC clones with human CD137 (Catalog number: RPCI11.C, Clone ID: 208A7; "human BAC clones") were used as a template for A2-1 and A2-2 homologous recombination fragments. The conditions for the PCR amplification were shown in the tables below.

TABLE 4

The PCR reaction system (20 μL)

| Composition | Amount |
|---|---|
| 10× buffer for KOD-plus DNA polymerase | 2 μL |
| dNTP (2 mM) | 2 μL |
| MgSO$_4$ (25 mM) | 0.8 μL |
| Upstream primer F (10 μM) | 0.6 μL |
| Downstream primer R (10 μM) | 0.6 μL |
| BAC DNA templates | 50 ng |
| KOD-Plus DNA polymerase (1 U/μL) | 0.6 μL |
| H$_2$O | Add to 20 μL |

TABLE 5

The PCR reaction conditions

| Temperature | Time | Cycles |
|---|---|---|
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 57° C. | 30 sec | |
| 68° C. | 1 kb/min | |
| 68° C. | 10 min | 1 |
| 4° C. | 10 min | 1 |

The PCR products (DNA fragments) A1, A2-1, A2-2, A3, B, C1 and C2 were collected and were used to construct targeting vectors.

Example 2. Construction of Homologous Recombination Targeting Vector

The mouse CD137 gene and human CD137 gene are shown in FIG. 1. The targeting strategy is shown in FIG. 2.

The mouse CD137 gene (Gene ID: 21942) (based on the transcript of NCBI accession number NM_011612.2→NP_035742.1 whose mRNA sequence is set forth in SEQ ID NO: 15, and the corresponding amino acid sequence is set forth in SEQ ID NO: 16) has 8 exons. Among them, exon 1 and part of exon 2 do not encode amino acid sequences of mouse CD137 protein. Part of exon 2, exons 3-6, and part of exon 7 were replaced with the corresponding coding sequence of human homologous CD137 gene (Gene ID: 3604) (based on the transcript of NCBI accession number NM_001561.5→NP_001552.2, whose mRNA sequence is set forth in SEQ ID NO: 17, and the corresponding protein sequence is set forth in SEQ ID NO: 18). The neo gene was also added for positive clone selection. For the vector, the 5'-homology arm (SEQ ID NO: 19) has a length of 4847 bp, the 3'-homology arm has a length of 4728 bp (SEQ ID NO: 20), and the human DNA fragment has 6706 bp (SEQ ID NO: 21). The modified humanized CD137 was obtained by homologous recombination. The coding region sequence, mRNA sequence and the encoded amino acid sequence thereof of the humanized CD137 are respectively set forth in SEQ ID NO: 22, SEQ ID NO: 23, and SEQ ID NO: 24.

Targeting Vector

The targeting vector was obtained by the following steps:

(1). pBs-Neo-B plasmid was obtained by ligating fragment B and pBs-Neo vector by BamHI/NotI restriction enzymes. The sequence of pBs-Neo-B plasmid was then verified by sequencing.

(2). Fragment A1 and fragment A2-1 were ligated by overlap extension PCR (Phusion DNA Polymerases); Fragment A2-2 and fragment A3 were also ligated by overlap extension PCR (reaction system and conditions are shown in the tables below). The sequences of the products were verified by sequencing. The ligated fragments were further inserted into the pBs-Neo-B plasmid (KpnI/BstZ171/XhoI) to obtain the pBs-Neo-(A1+A2-1+A2-2+A3+B) plasmid.

(3). pBs-Neo-(A1+A2-1+A2-2+A3+B) plasmids were introduced into human BAC clones by electroporation. pBs-Neo-(AB) plasmids, which contains AB fragment (SEQ ID NO: 25), were obtained by homologous recombination. The AB fragment was shown in FIG. 2, and has human DNA fragment SEQ ID NO: 21.

(4). pBs-Neo-(AB) plasmids were introduced into mouse BAC clones by electroporation. Mouse BAC clones with AB fragments were obtained by homologous recombination.

(5). pDTA-down-C plasmids were obtained by ligating fragments C1 and C2 to pDTA-down plasmids (AIO kits). The sequences of the plasmids were further verified by sequencing.

(6). pDTA-down-C plasmids were introduced into mouse BAC clones containing AB fragments. pDTA-down-ABC plasmids containing 5'-homologous arm, AB fragments, and 3'-homologous arm were obtained by homologous recombination (FIG. 2).

TABLE 6

The PCR reaction system (20 μL)

| Composition | Amount |
| --- | --- |
| 5× Phusion HF Buffer | 4 μL |
| dNTP (10 mM) | 0.4 μL |
| Primer F (10 μM) | 1 μL |
| Primer R (10 μM) | 1 μL |
| DNA template | 5 ng |
| Phusion DNA polymerase(2 U/μL) | 0.2 μL |
| H$_2$O | Add to 20 μL |

TABLE 7

The PCR reaction conditions
PCR Conditions

| Temperature | Time | Cycles |
| --- | --- | --- |
| 98° C. | 30 sec | 1 |
| 98° C. | 10 sec | 35 |
| 58° C. | 25 sec | |
| 72° C. | 30 sec/kb | |
| 72° C. | 5-10 min | 1 |
| 4° C. | 10 min | 1 |

In step (2), when fragments A1 and A2-1 were ligated, Primer F in Table 6 was SEQ ID NO: 1, Primer R was SEQ ID NO: 4, and template DNA was the recovered PCR amplification product of A1 fragment and A2-1 fragment. When fragments A2-2 and A3 were ligated, Primer F was SEQ ID NO: 5, primer R was SEQ ID NO: 8, and template DNA was the recovered PCR amplification product of A2-2 fragment and A3 fragment. The electroporation process is described in detail below.

Electroporation

The BAC clones were added into LB liquid medium (5 mL) with appropriate antibiotics as shown in the table below. The bacteria were cultured at 30° C. for 12-16 hours at 250 rpm. The next day, the corresponding antibiotics (1:50) as shown in the table below were added into the LB liquid medium, and the bacteria were further cultured at 30° C., 250 rpm for 2-3 hours. When the OD value reached 0.15~0.2, 30 mL of culture medium was collected. 1.2 mL of arabinose (0.4%) was added. After 45-60 min of induction, the culture was kept on ice for 30 min. The culture was then aliquoted into 50 mL centrifuge tubes, centrifuged at 5000 rpm for 10 min at −1° C. The supernatant was discarded. ddH$_2$O (10 mL) was then added, and the solution was then centrifuged at 5000 rpm for 10 min at −1° C. The supernatant was discarded. After being washed for one more time, the bacteria were kept on ice.

15 μL of plasmids (0.2-0.3 ng/μL) was added into a 1.5 mL Eppendorf tube, and kept on ice. 85 μL of competent cells were then added, and were carefully mixed with the plasmids. The mixture was then transferred to cuvettes. The setting for the electroporator (BTX, ECM-630) was 1.3 kV, 50 μF, and 125Ω Immediately after electroporation, 800 μL of LB liquid medium was added. After culturing the bacteria at 150 rpm for 1 h at 30° C., the bacteria were plated on petri dishes with appropriate antibiotics as shown in the table below, and were then cultured for at least 30 hours.

TABLE 8

| Steps | Antibiotics for LB medium | Antibiotics for petri dishes |
| --- | --- | --- |
| Step (3) (Human BAC) | Chloramphenicol (Chl) | Carbenicillin (CBC) + Kanamycin (Kan) |
| Step (4) (Mouse BAC) | Chl | Chl + Kan |
| Step (6) (BAC containing AB fragments) | Chl + Kan | CBC + Kan | pBs-Neo Plasmids

Figure 4:
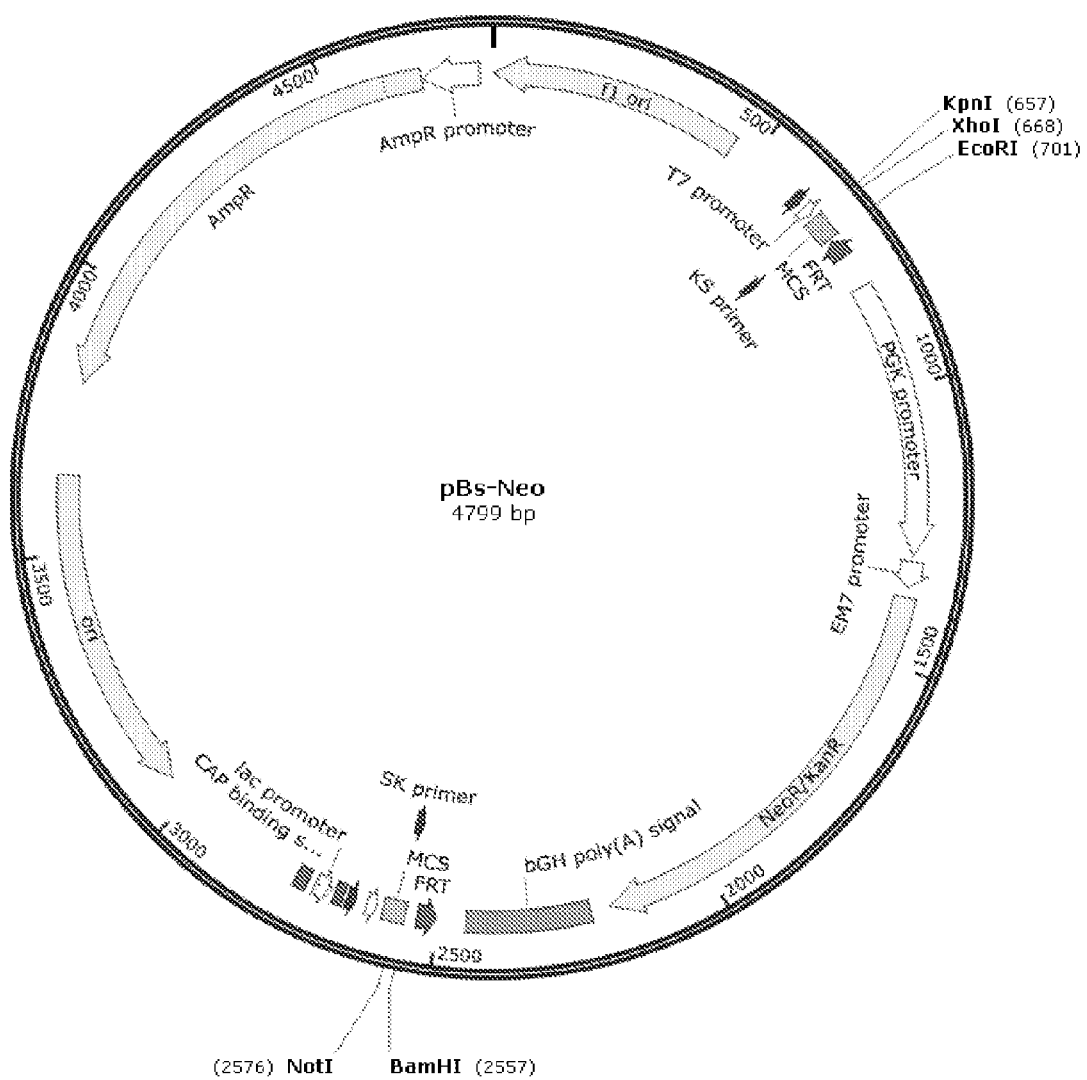
FIG. 4 is a schematic diagram showing the structure of pBs-Neo plasmid.

FIG. 4 shows pBs-Neo vector map. The plasmid backbone was obtained from Agilent (Cat. No. 212205). DNA fragment containing frt and neo gene (neomycin-resistance) (SEQ ID NO: 26) was synthesized and ligated to the vector backbone by restriction enzyme digestion (EcoRI/BamHI). The sequences of the plasmids were further verified by sequencing.

Example 3. Verification of pDTA-Down-ABC Vector

Figure 5:
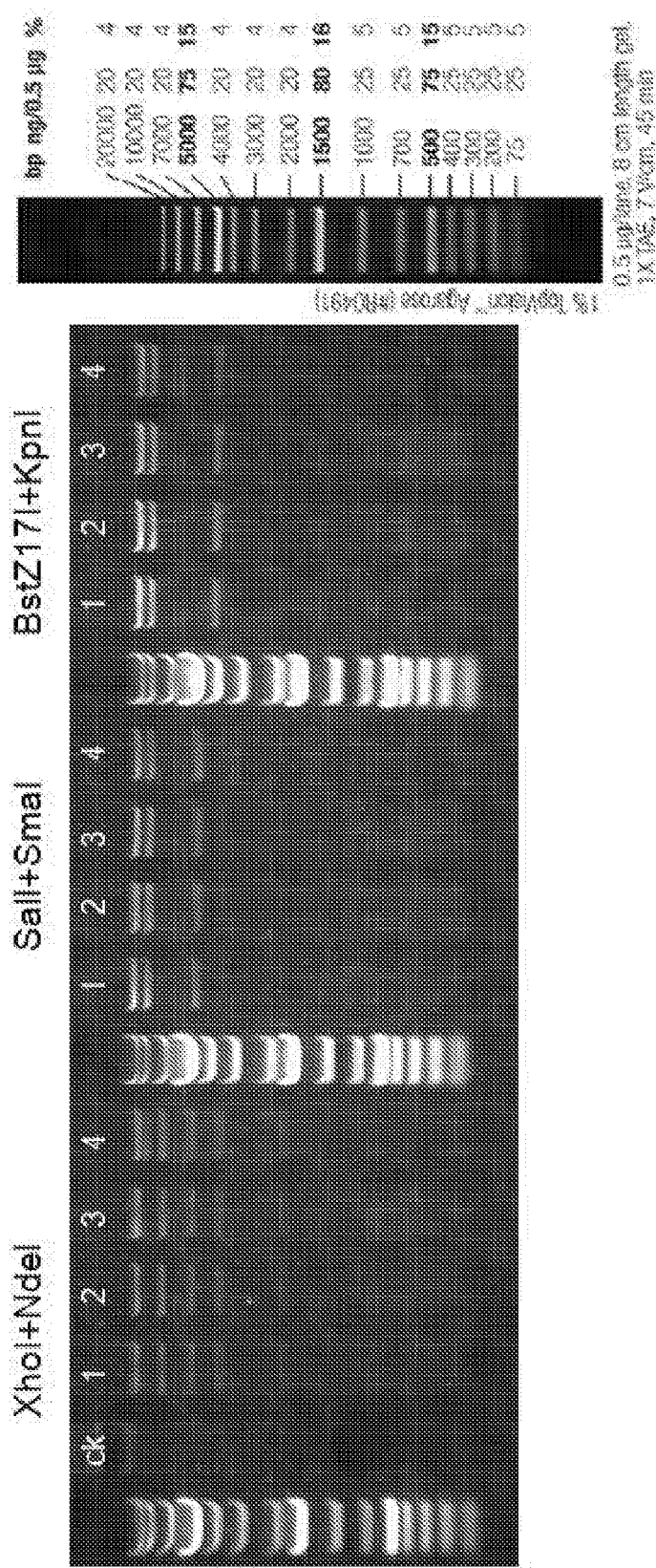
FIG. 5 shows the restriction enzymes digestion results of the targeting plasmid pDTA-down-ABC by three sets of restriction enzymes.
Figures 6A, 6B, 6C, 6D:
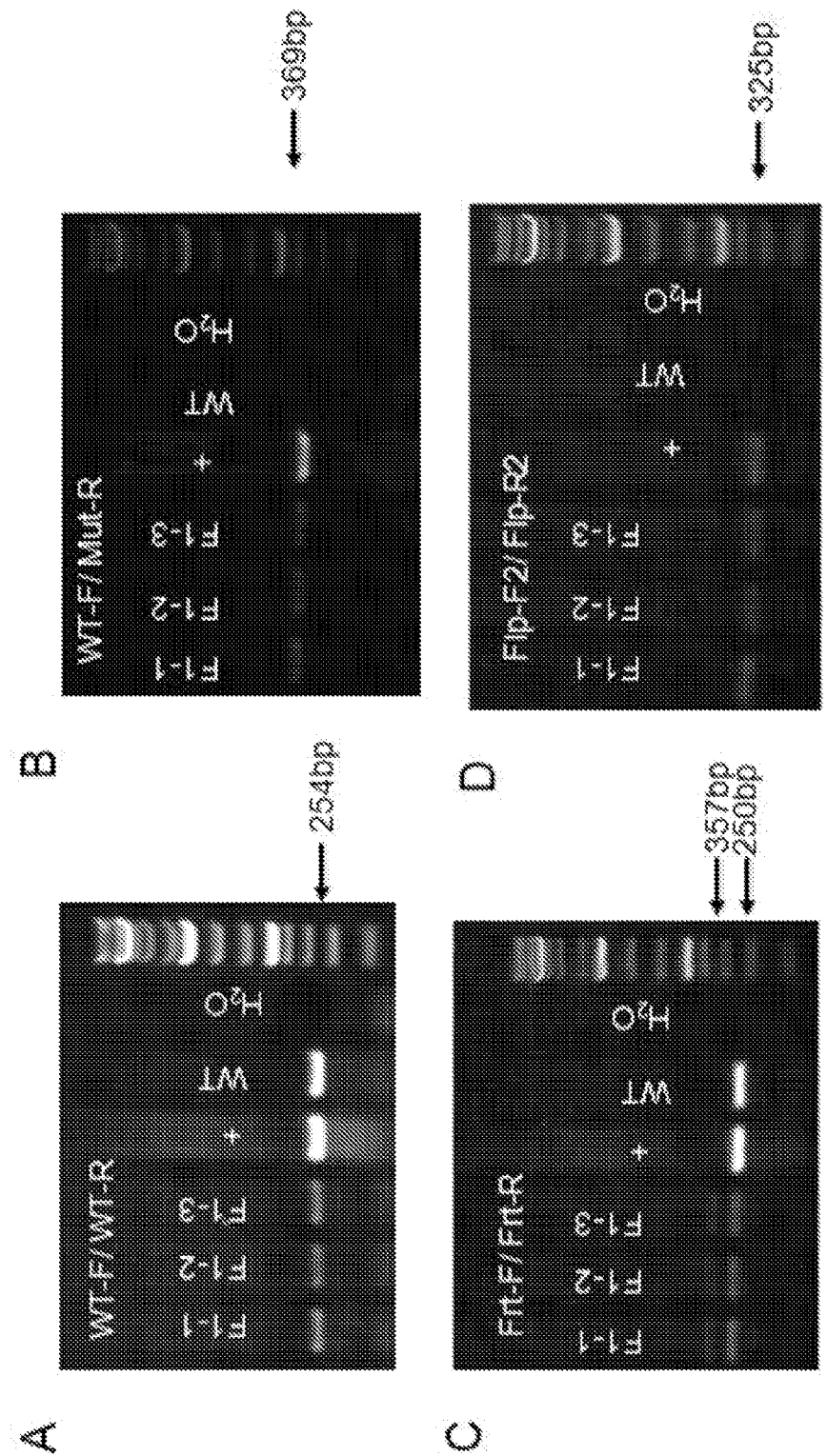
FIGS. 6A-6D show the PCR results using samples collected from the tails of F1 generation mice. WT stands for wildtype, and + stands for positive control. As shown in the figure, F1-1, F1-2 and F1-3 are heterozygous for humanized CD137.

Four pDTA-down-ABC clones were randomly selected and tested by three sets of restriction enzymes. Among them, XhoI+NdeI should generate 9010 bp+5834 bp+4165 bp+3058 bp+1448 bp+494 bp fragments; SalI+SmaI should generate 11641 bp+7563 bp+4083 bp+722 bp fragments; BstZ17I+KpnI should generate 12111 bp+7897 bp+3582 bp+419 bp fragments. The results for Plasmids 1, 2, and 3 were in line with the expectations (FIG. 5). The sequences of Plasmids 1 and 2 were further confirmed by sequencing.

Example 4. C57BL/6 Mouse Embryonic Stem Cell Culture, Transfection and Clone Screening Embryonic Stem Cell Culture C57BL/6 embryonic stem cells were cultured in petri dishes with feeder cells, and were incubated in an incubator at 37° C., 5% CO$_2$ with saturated humidity. The composition of the culture medium is shown in the table below.

TABLE 9

| Medium composition | Volume |
| --- | --- |
| Knockout DMEM | 500 ml |
| FBS | 90 ml |
| MEM NEAA | 6 ml |
| L-Glutamine | 6 ml |
| ESGRO LiF | 60 μL |
| β-Mercaptoethanol | 600 μL |

Transfection by Electroporation

C57BL/6 embryonic stem cells were confirmed to be in good condition prior to electroporation.

were collected and tested by PCR to determine whether the mouse is a humanized CD137 gene heterozygote. The primers for PCR are shown in the table below.

TABLE 10

| Primer | Sequence | Product length |
|---|---|---|
| WT-F | 5'-GTTTAGCAAGCATGCTATCAGTCAAGC-3' (SEQ ID NO: 27) | WT: 254 bp |
| WT-R | 5'-CTGAACTGAGTCTTCAACAGTCATGTC-3' (SEQ ID NO: 28) | |
| WT-F | 5'-GTTTAGCAAGCATGCTATCAGTCAAGC-3' (SEQ ID NO: 27) | Mut: 369 bp |
| Mut-R | 5'-CACACAGCTAGGTTGTAGCATCC-3' (SEQ ID NO: 29) | |
| Frt-F | 5'-GACACACGTCTGGAGTCAGAGGAC-3' (SEQ ID NO: 30) | Mut: 250 bp |
| Frt-R | 5'-CTCGCTATACAACTGCCTCCAGGC-3' (SEQ ID NO: 31) | WT: 357 bp |
| Flp-F2 | 5'-GACAAGCGTTAGTAGGCACATATAC-3' (SEQ ID NO: 32) | Mut: 325 bp |
| Flp-R2 | 5'-GCTCCAATTTCCCACAACATTAGT-3' (SEQ ID NO: 33) | |

The petri dishes with embryonic stem cells were retrieved from the incubator. The medium was removed. 5 ml PBS was added, and the petri dishes were washed twice. 1.5 ml 0.25% trypsin was added to each petri dish, and was incubated in 37° C. incubator for 3 minutes. 3.5 ml of ES medium per dish was then added to stop the digestion. The cells were then transferred to 50 ml centrifuge tubes to count cells. $1.2 \times 10^7$ cells were added into a new 50 ml centrifuge tube. The cells were centrifuged at 1200 rpm for 5 min at 4° C. The supernatant was then removed. An appropriate amount of RPMI medium (without phenol red) was added. The cells were then suspended and gently mixed with pDTA-down-ABC vector. The mixture was kept in ice water bath for 5 minutes, and was then transferred to cuvettes. The setting for electroporation was 280V, 500 g, and 10 ms. The cuvettes were kept in ice water bath for 5 min, and then kept at room temperature for 5 minutes. The cells were then transferred into a 50 ml centrifuge tube containing 40 ml of embryonic stem cell culture medium. The mixture was then divided, and added into four 100 mm petri dishes containing MMC feeder cells. These cells were then incubated at 37° C. in a 5% $CO_2$ incubator. After incubating these cells for 20 hours, the medium was replaced by G418 medium.

Clone Selection

After 20 hours of culturing, the medium was replaced by G418 medium for positive selection and negative selection. The cell colonies were then picked and transferred into 96-well plates. After the cells grew for a sufficient period of time, the cells were then transferred to 48-well, 6-well plates and 60-mm petri dishes, and the DNA of the cells was collected. PCR and Southern blotting were used to select the positive clones.

Example 5. Microinjection and Embryo Transfer

The positive embryonic stem cells in Example 4 were injected into BALB/c mouse blastocysts. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected blastocysts were then transferred to a culture medium and were cultured for a short time period, and then was transplanted into the oviduct of the recipient mouse to produce the chimeric mice (F0 generation). The chimeric mouse was then mated with Flp recombinase transgenic mice (FIG. 3), generating F1 generation (black or gray color). Black mice were selected. Genomic DNA from the tails of black mice The PCR conditions were
95° C. 5 min;
95° C. 30 sec, 62° C. 30 sec, 72° C. 25 sec, 35 cycles in total;
72° C. 10 min;
4° C. 10 min.

PCR was performed to determine whether the recombinant fragment was inserted at the correct genomic site. The primer pair WT-F and WT-R was used to amplify exon 2 of CD137 gene of wild-type mice. The primer pair Mut-F and WT-R was used to amplify the humanized exon 2 fragment.

The primer pair Frt-F and Frt-R was used to amplify neo fragments to determine whether the neo gene was removed. The primer pair Flp-F2 and Flp-R2 was used to confirm the presence of Flp fragments.

The PCR results of 3 positive mice were shown in FIGS. 6A-6D.

Example 6. Verification of Genetically Modified Humanized Mouse Model

A humanized heterozygous F1 generation mouse was selected. Two wildtype C57BL/6 mice were used as the control.

7.5 µg of mouse anti-CD3 antibody was injected intraperitoneally to the mice. The spleens were collected 16 hours after the injection, and the spleen samples were grinded. The samples were then passed through 70 µm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS.

Figures 7A, 7B, 7C, 7D, 7E, 7F:
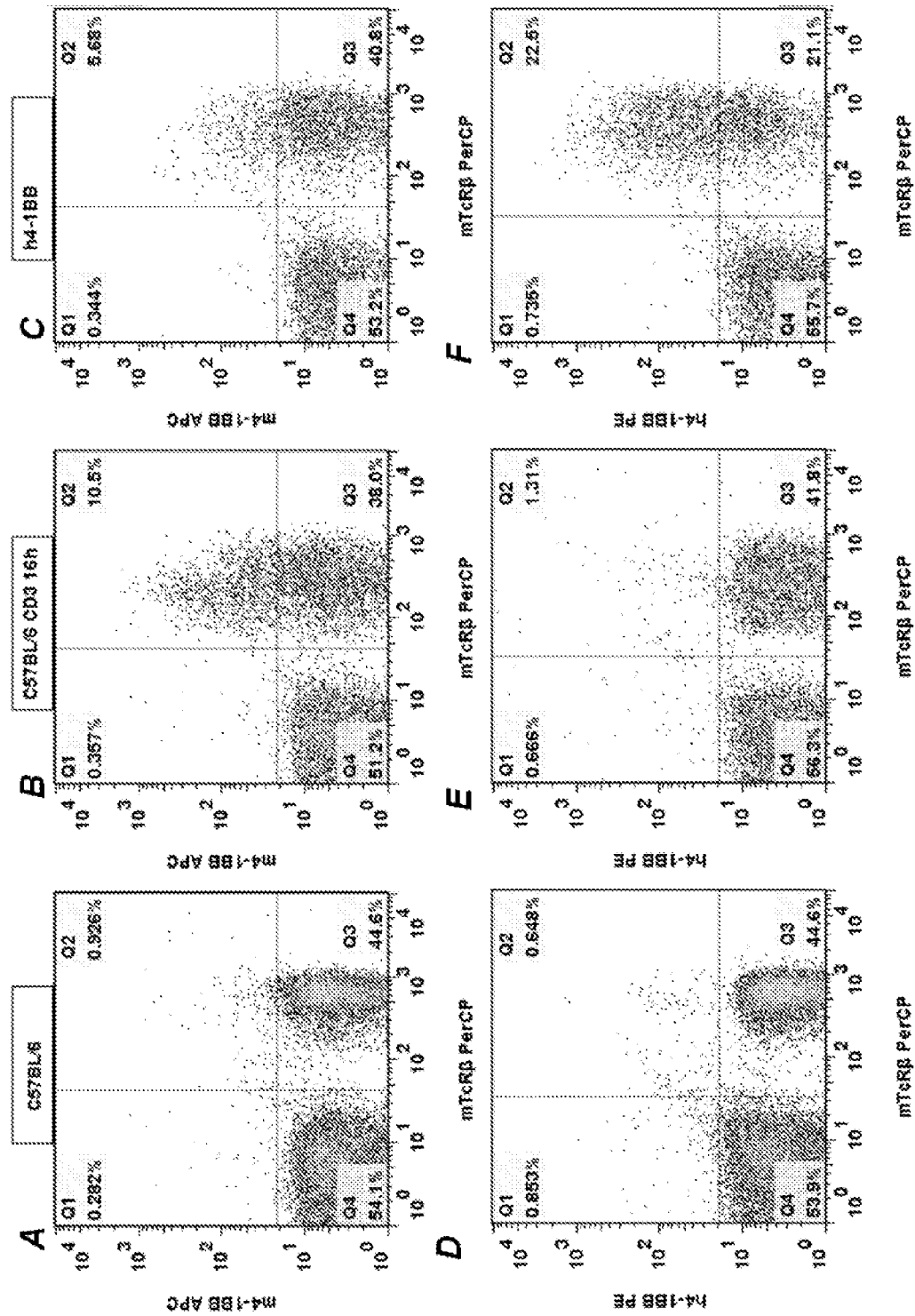
FIGS. 7A-7F are flow cytometry results for two C57BL/6 mice (FIGS. 7A-7B and 7D-7E) and one heterozygous humanized CD137 mouse (FIGS. 7C and 7F). Flow cytometry was performed with 1) antibody against mouse CD137 (m4-1BB APC)) and antibody against mouse TcRβ (mTcRβ PerCP) (FIGS. 7A-7C); and 2) antibody against human CD137 (h4-1BB PE), and antibody against mouse TcRβ (mTcRβ PerCP) (FIGS. 7D-7F). Compared to the control groups, no spleen cells stained with h4-1BB PE were observed in the spleen of C57BL/6 mice (FIGS. 7D and 7E); while spleen cells stained with h4-1BB PE were observed in the heterozygous humanized CD137 mouse (FIG. 7F).

FACS: Anti-mouse CD137 antibody (m4-1BB APC) and anti-mTCRβ antibody (TCRβ PerCP), or anti-human CD137 antibody (h4-1BB PE) and anti-mTCRβ antibody (TCRβ PerCP) were used to stain the cells. The cells were washed once with PBS and analyzed by flow cytometry. The results of flow cytometry (FIGS. 7A-7F) showed that the spleen of humanized heterozygous mouse (FIGS. 7C and 7F) had cells expressing mouse CD137 protein and humanized CD137 protein, while the spleen of the C57BL/6 control mice did not have detectable cells expressing human or humanized CD137 proteins (FIGS. 7D and 7E).

RT-PCR detection: RNA was extracted from the spleen cells, and cDNA was then obtained by reverse transcription using a reverse transcription kit.

Primers for mCD137 RT-PCR:

```
m4-1BB RT-PCR F2:
                                    (SEQ ID NO: 34)
5'-GAACGGTACTGGCGTCTGTC-3' and m4-1BB RT-PCR R2:
                                    (SEQ ID NO: 35)
5'-GGTCCTCCCTCTGGAGTCAC-3'
``` were used to amplify mouse CD137 fragment of 156 bp.
Primers for hCD137 RT-PCR:

```
h4-1BB RT-PCR F1:
                                    (SEQ ID NO: 36)
5'-CTGCACTCCAGGGTTTCACT-3' and h4-1BB RT-PCR R1:
                                    (SEQ ID NO: 37)
5'-AGTTTGTCCAGGGTCGACAG-3'
``` were used to amplify human CD137 fragment of 155 bp.

PCR reaction system was 20 µL, reaction conditions: 95° C., 5 min; (95° C., 30 sec; 60° C., 30 sec; 72° C., 30 sec, 35 cycles); 72° C., 10 min; and then keeping it at 4° C. GAPDH was used as an internal reference.

Figure 8:
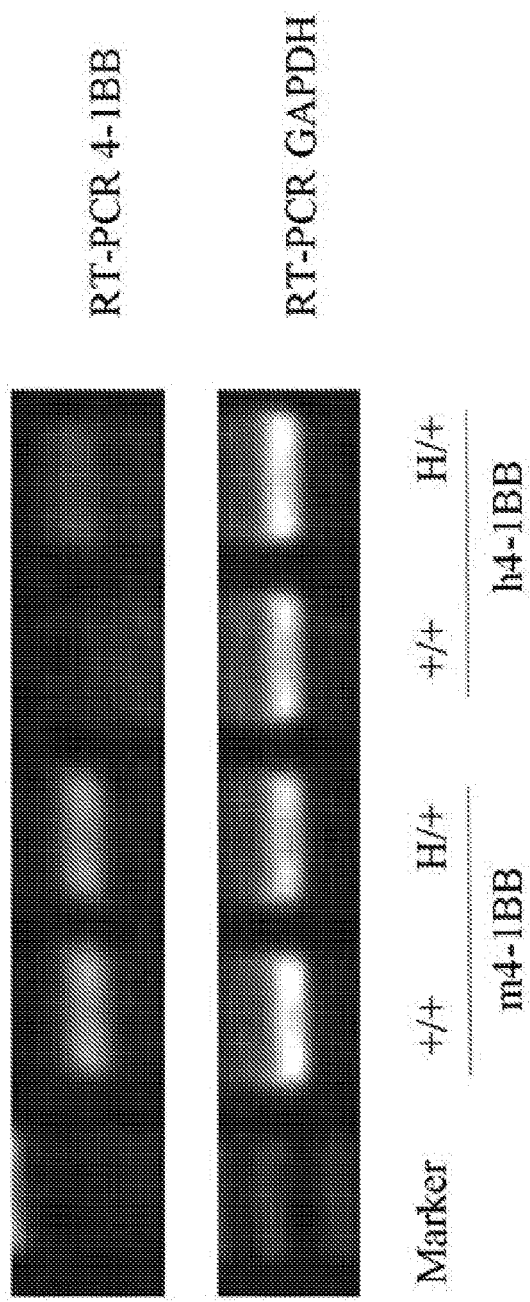
FIG. 8 shows results from RT-PCR for human CD137 (h4-1BB) and mouse CD137 (m4-1BB) mRNA. +/+ indicates wildtype C57BL/6 mice; H/+ indicates the F1 generation mouse that is heterozygous for humanized CD137; and GAPDH was used as a control.

The results are shown in FIG. 8. The mRNA expression of mouse CD137 was detected in the activated cells of wildtype C57BL/6 mice and F1 generation heterozygous mouse (H/+); while the mRNA expression of humanized CD137 was only detected in the activated cells of the F1 generation heterozygous mouse (H/+).

Figures 9A, 9B, 9C, 9D, 9E, 9F:
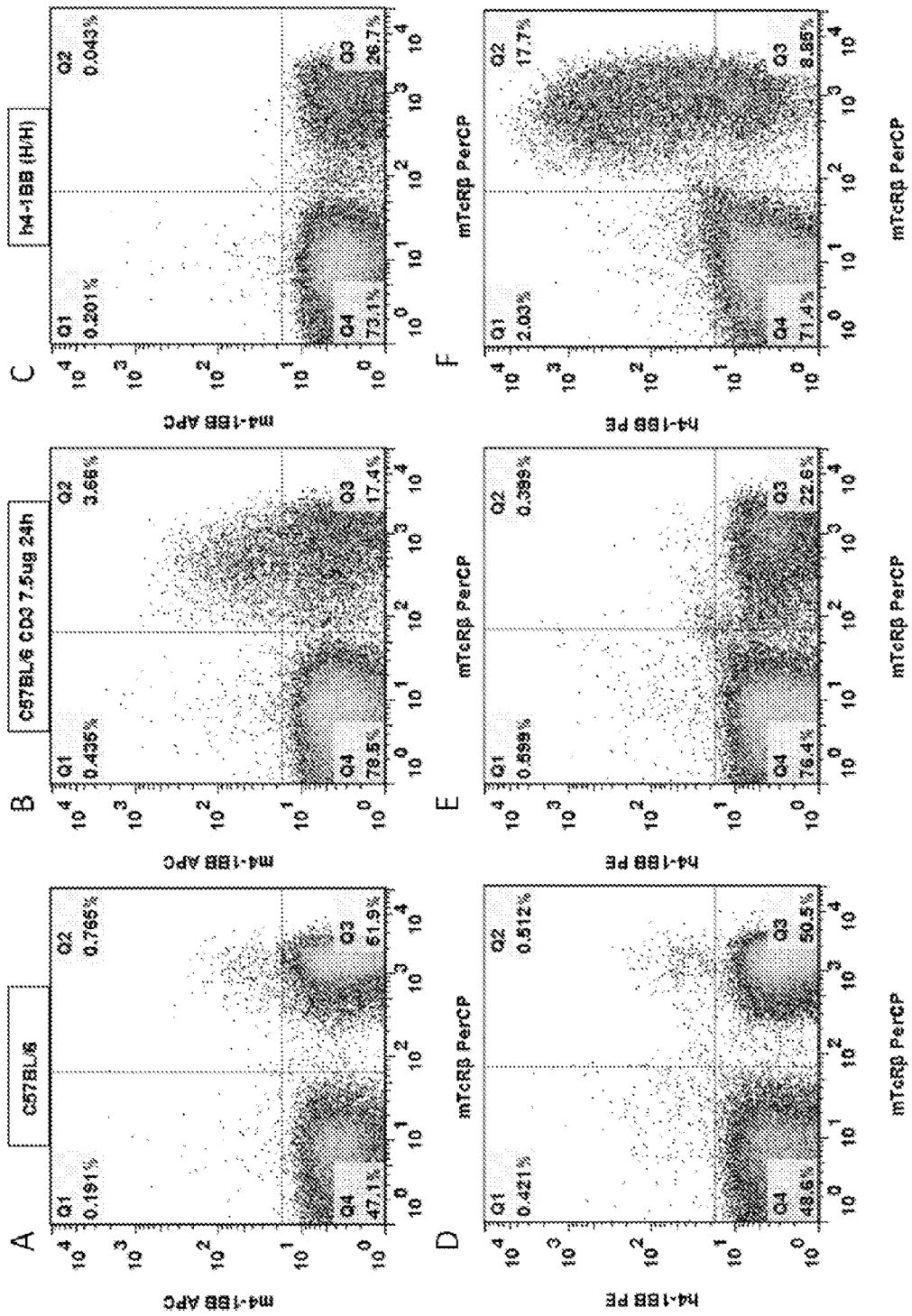
FIGS. 9A-9F are flow cytometry results. C57BL/6 wildtype mice were used in FIGS. 9A, 9B, 9D, and 9E. The mouse in FIG. 9A and FIG. 9D were not stimulated with anti-mCD3 antibody; and the mouse in FIG. 9B and FIG. 9E were stimulated with anti-mCD3 antibody. A humanized CD137 homozygous mouse was used in FIG. 9C and FIG. 9F, and was stimulated with anti-mCD3 antibody. Flow cytometry was performed with: 1) antibody against mouse CD137 (m4-1BB APC)) and antibody against mouse TcRβ (mTcRβ PerCP) (FIGS. 9A-9C); and 2) antibody against human CD137 (h4-1BB PE), and antibody against mouse TcRβ (mTcRβ PerCP) (FIGS. 9D-9F).
Figure 10:
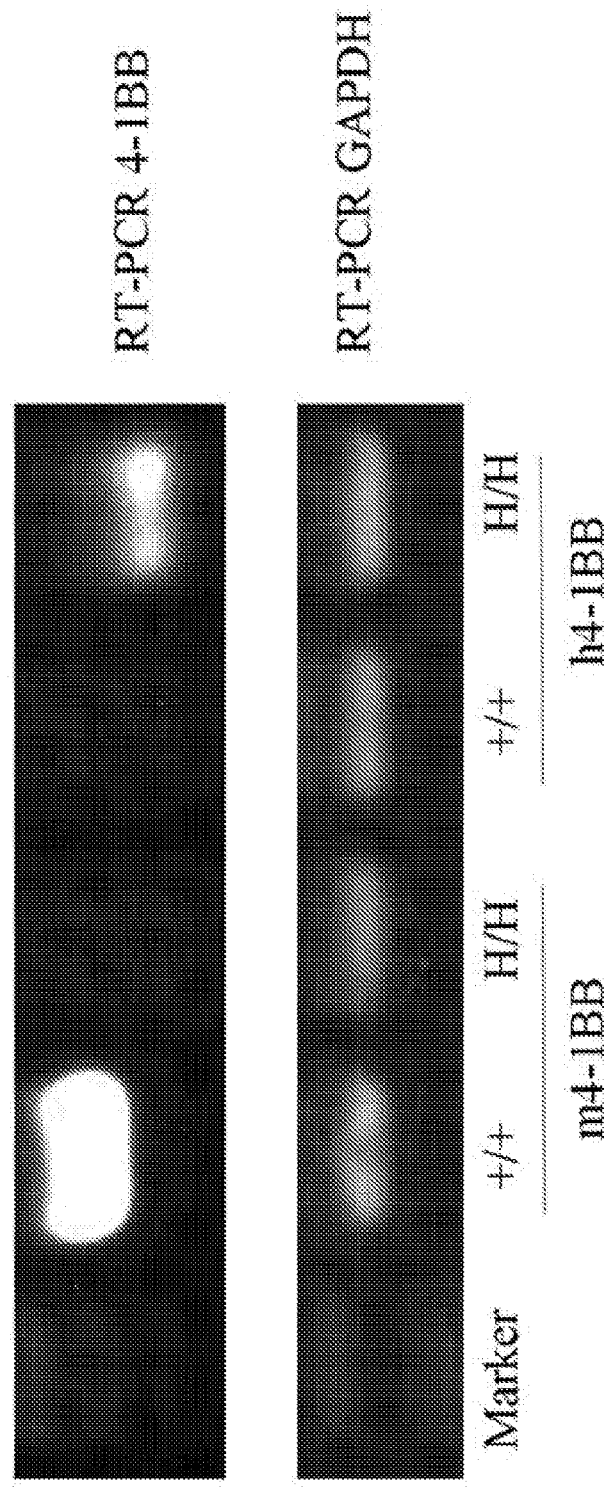
FIG. 10 shows results from RT-PCR for human CD137 (h4-1BB) and mouse CD137 (m4-1BB) mRNA. +/+ indicates wildtype C57BL/6 mice; H/H indicates homozygous humanized CD137 mice. GAPDH was used as a control.

The F1 heterozygous mice were further mated to each other to obtain F2 generation homozygous mice. The homozygous mice were tested by FACS and RT-PCR by the methods as described above. FACS results (FIGS. 9A-9F) show that cells expressing humanized CD137 protein can be detected in the humanized CD137 homozygous mouse (FIG. 9F), and mouse CD137 can be detected in C57BL/6 with or without anti-CD3 antibody stimulation. RT-PCR results were shown in FIG. 10. The mRNA expression of mouse CD137 was only detected in the activated cells of wildtype C57BL/6 mice (+/+) and the mRNA expression of humanized CD137 was only detected in the activated cells of the humanized F2 generation homozygous mice (H/H).

The results above show that the CD137 humanized mouse can express humanized CD137 protein and the humanized CD137 protein can be recognized by the anti-hCD137 antibody.

Example 7. Pharmacological Test of Humanized CD137 Heterozygous Animal Model

Humanized CD137 heterozygous mice (4-6 weeks) were subcutaneously injected with mouse colon cancer cell MC38 ($5\times10^5$/100 µl PBS), and when the tumor volume grew to about 100 mm$^3$, the mice were divided to a control group and treatment groups based on tumor size (n=5/group). The treatment groups were randomly selected for being treated by two different anti-human CD137 antibodies (Ab1 and Ab2) (0.3 or 3 mg/kg); the control group was injected with an equal volume of saline solution. The frequency of administration was twice a week (6 times of administrations in total). The tumor volume and the body weight were measured twice a week. Euthanasia was performed when the tumor reached 3000 mm$^3$.

Figure 11:
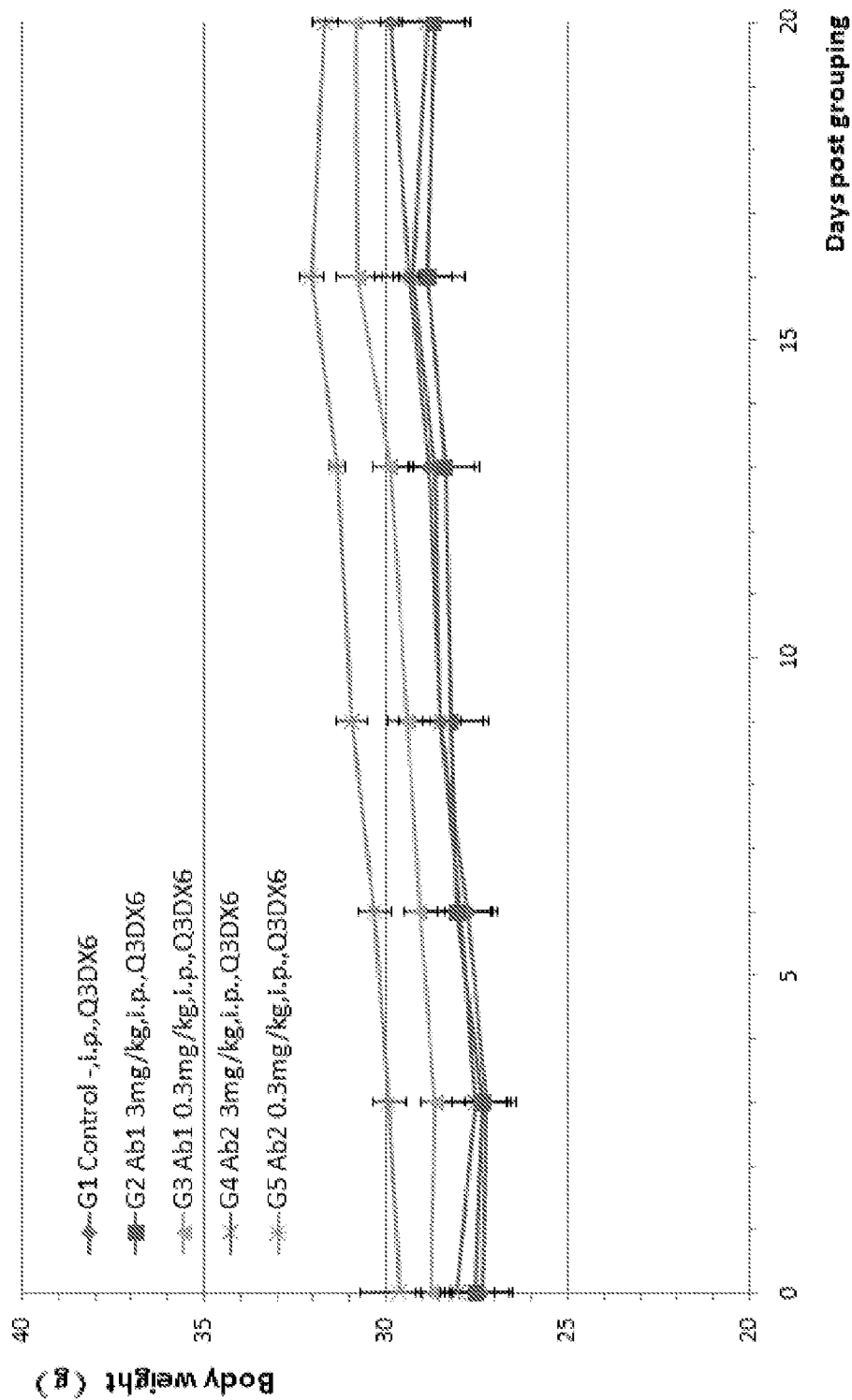
FIG. 11. Mouse colon cancer cells MC38 were injected into humanized CD137 heterozygous mice. Antitumor efficacy studies were performed with two different antibodies against human CD137 (AB-1, AB-2) at two different dosages (0.3 mg/kg and 3 mg/kg). The average weights of the G1 control group and the G2-G5 treatment groups are shown.
Figure 12:
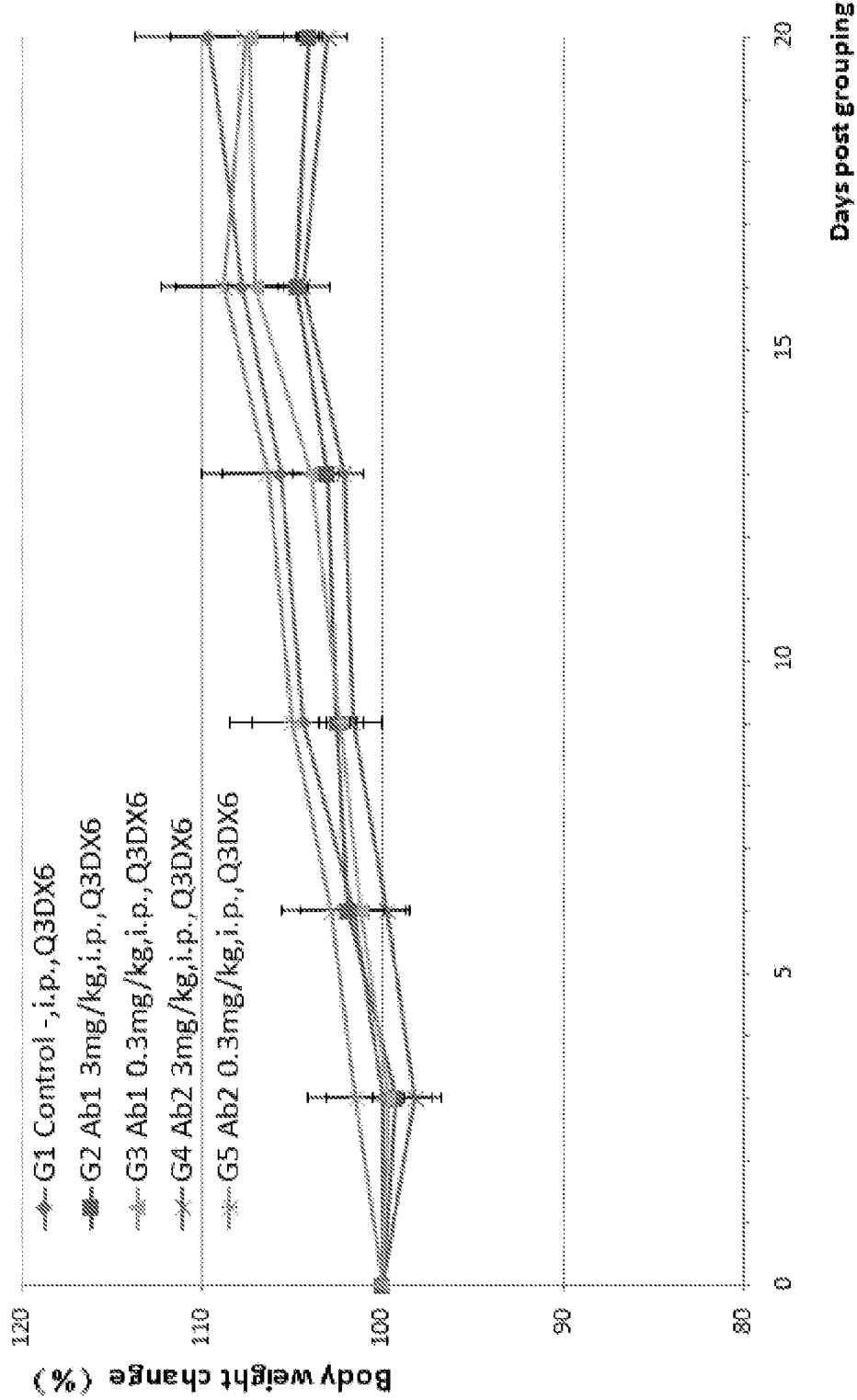
FIG. 12. Mouse colon cancer cells MC38 were injected into humanized CD137 heterozygous mice. Antitumor efficacy studies were performed with two different antibodies against human CD137 (AB-1, AB-2) at two different dosages (0.3 mg/kg and 3 mg/kg). The average weight change percentages of the G1 control group and the G2-G5 treatment groups are shown.

Overall, the animals in each group were healthy, and the body weights of all the treatment and control group mice slightly increased, and were not significantly different from each other (FIG. 11 and FIG. 12). The results indicated that the use of anti-human CD137 antibodies (Ab1 and Ab2) were well tolerated and did not cause obvious toxic effects. Table 11 shows results for this experiment, including the tumor volumes at the day of grouping (day 0), 13 days after the grouping (day 13), and at the end of the experiment (day 20), the survival rate of the mice, the number of tumor-free mice (non-existence of tumor), the Tumor Growth Inhibition value ($TGI_{TV}\%$), and the statistical differences (P value) in mouse body weights and tumor volume between the treatment and control groups.

TABLE 11

| | | Tumor volume (mm$^3$) | | | Survival | Non-existence of tumor | $TGI_{TV}\%$ | P value | |
|---|---|---|---|---|---|---|---|---|---|
| | | Day 0 | Day 13 | Day 20 | | | | Body weight | Tumor Volume |
| Control | G1 | 225 ± 24 | 971 ± 309 | 1825 ± 685 | 5/5 | 0/5 | N/A | N/A | N/A |
| Treatment | G2 (Ab1, 3 mg/kg) | 231 ± 37 | 569 ± 94 | 1120 ± 325 | 5/5 | 0/5 | 44.5 | 0.282 | 0.379 |
| | G3 (Ab1, 0.3 mg/kg) | 231 ± 27 | 947 ± 322 | 2000 ± 975 | 5/5 | 0/5 | 0 | 0.318 | 0.887 |
| | G4 (Ab2, 3 mg/kg) | 230 ± 22 | 404 ± 89 | 496 ± 108 | 5/5 | 0/5 | 83.4 | 0.398 | 0.091 |
| | G5 (Ab2, 0.3 mg/kg) | 228 ± 25 | 411 ± 145 | 733 ± 231 | 5/5 | 0/5 | 68.4 | 0.005 | 0.169 |

Figure 13:
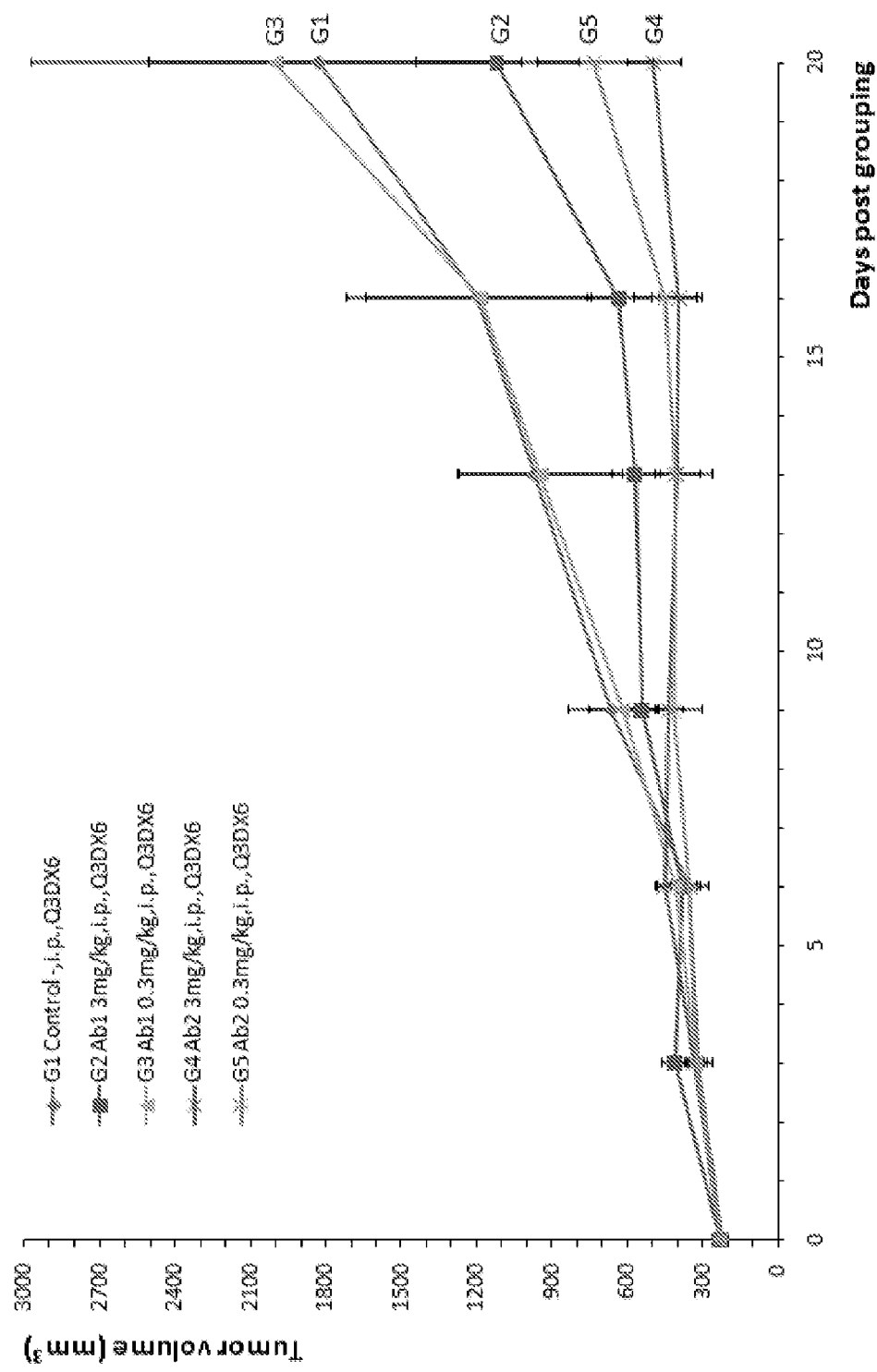
FIG. 13. Mouse colon cancer cells MC38 were injected into humanized CD137 heterozygous mice. Antitumor efficacy studies were performed with two different antibodies against human CD137 (AB-1, AB-2) at two different dosages (0.3 mg/kg and 3 mg/kg). The average volumes of tumors in the G1 control group and the G2-G5 treatment groups are shown.

The tumor in the control group continued growing during the experimental period; when compared with the control group mice, the tumor volumes in the treatment groups G2, G4, and G5 were smaller than the control group (FIG. 13).

With respect to the tumor volume, in the control group (G1), the average tumor volume was 1825±685 mm$^3$. The tumor volumes in the groups that were treated with Ab1 were 1120±325 mm$^3$ (G2, 3 mg/kg), 2000±975 mm$^3$ (G3, 0.3 mg/kg), and the tumor volumes in the groups that were treated with Ab2 were 496±108 mm$^3$ (G4, 3 mg/kg), 733±231 mm$^3$ (G5, 0.3 mg/kg). Furthermore, $TGI_{TV}\%$ are higher than 60% in both the G4 and G5 groups.

The results show that at the same dosage, anti-human CD137 antibody Ab2 have better tumor inhibitory effects than Ab1, and both Ab1 and Ab2 have better tumor inhibitory effects at a relatively high dosage.

Example 8. Pharmacological Test of Humanized CD137 Homozygous Animal Model

Humanized CD137 homozygous mice (4-8 weeks) were subcutaneously injected with MC38 cells ($5\times10^5$/100 µl PBS), and when the tumor volume grew to about 100 mm³, the mice were divided to a control group and a treatment group based on tumor size (n=6/group). The treatment group was treated with anti-human CD137 antibody Ab2 (3 mg/kg); the control group was injected with an equal volume of saline solution. The frequency of administration was one injection every three days, (6 times of administrations in total). The tumor volume and the body weight were measured twice a week. Euthanasia was performed when the tumor reached 3000 mm³.

Figure 14:
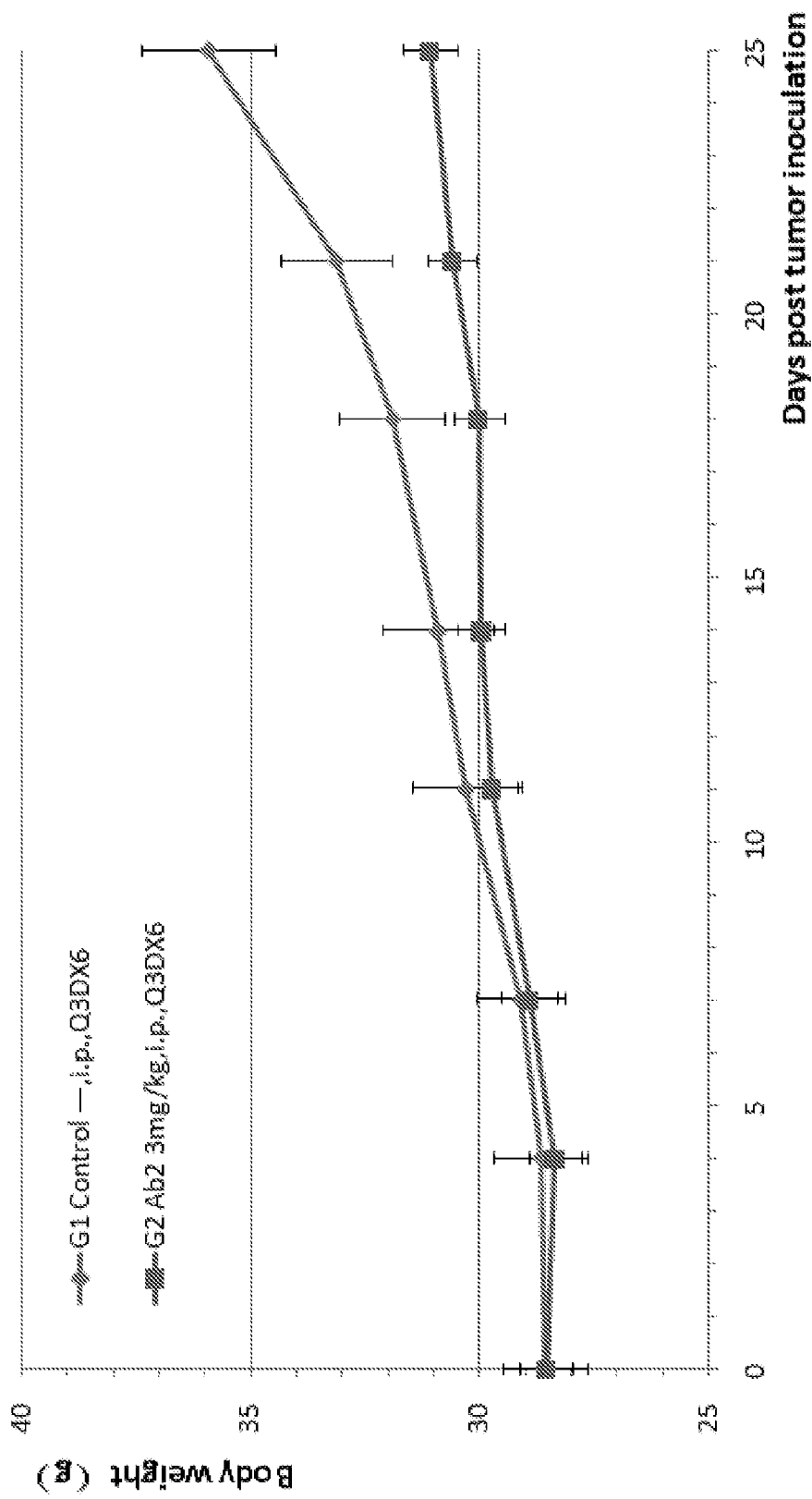
FIG. 14. Mouse colon cancer cells MC38 were injected into humanized CD137 homozygous mice. Antibody against human CD137 (AB-2) was administered to the mice (3 mg/kg). The average weights of the G1 control group and the G2 treatment group are shown.
Figure 15:
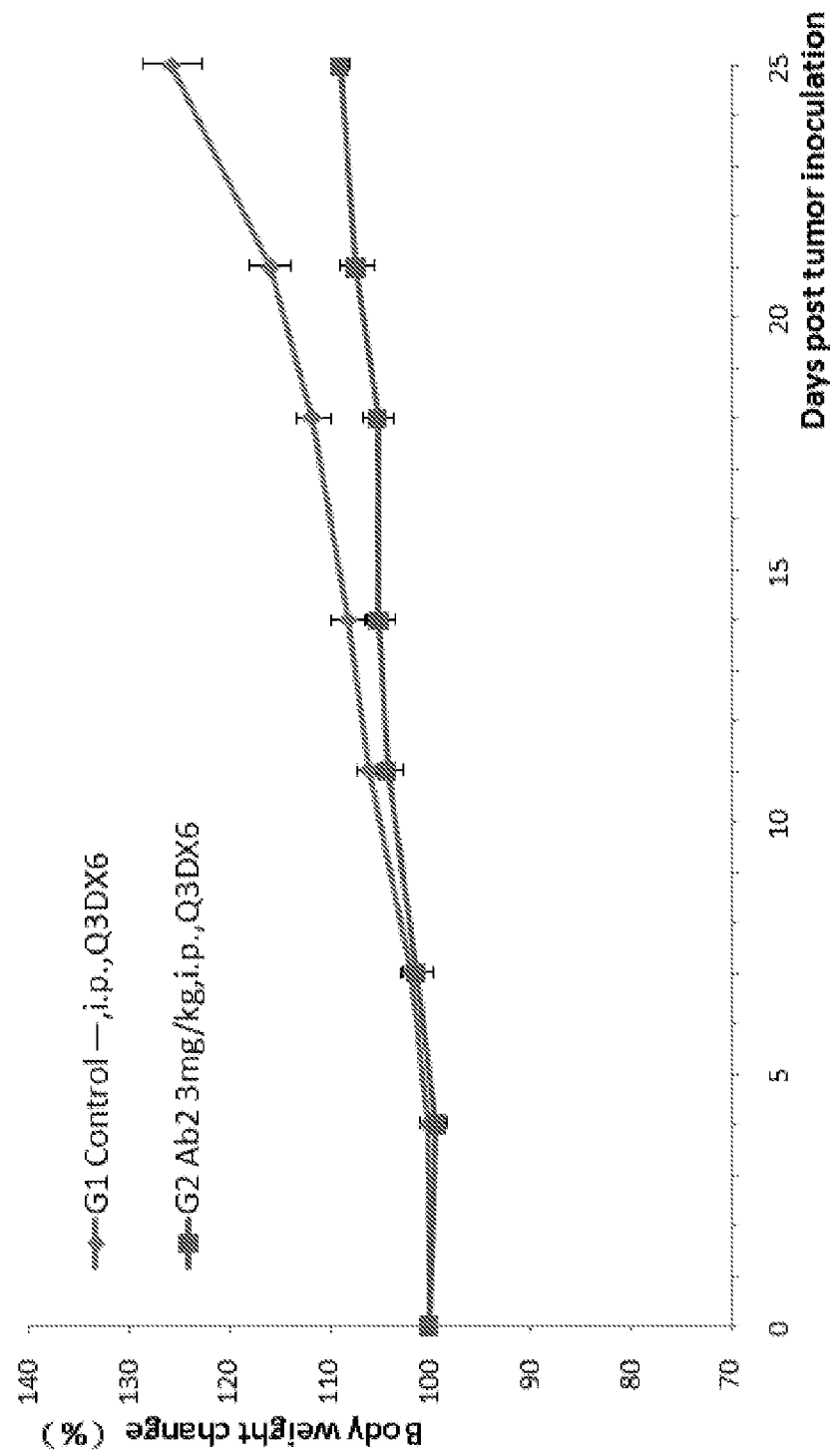
FIG. 15. Mouse colon cancer cells MC38 were injected into humanized CD137 homozygous mice. Antibody against human CD137 (AB-2) was administered to the mice (3 mg/kg). The average weight change percentages of the G1 control group and the G2 treatment group are shown.

Overall, the animals in both groups were healthy, and the body weights of all the treatment and control group mice increased (FIG. 14 and FIG. 15). The results indicated that anti-human CD137 antibody Ab2 was well tolerated and did not cause obvious toxic effects.

Table 12 shows results for this experiment, including the tumor volumes at the day of grouping (day 0), 18 days after the grouping (day 18), and at the end of the experiment (day 25), the survival rate of the mice, the number of tumor-free mice (non-existence of tumor), and the statistical differences (P value) in mouse body weights and tumor volume between the treatment and control groups.

TABLE 12

| | | Tumor volume (mm³) | | | Survival | Non-existence of tumor | P value Body weight | P value Tumor Volume |
|---|---|---|---|---|---|---|---|---|
| | | Day 0 | Day 18 | Day 25 | | | | |
| Control | G1 | 175 ± 3 | 1675 ± 241 | 3501 ± 458 | 6/6 | 0/6 | N/A | N/A |
| Treatment | G2 (Ab2) | 175 ± 3 | 79 ± 51 | 84 ± 76 | 6/6 | 3/6 | 102.7 | 0.012 |

Figure 16:
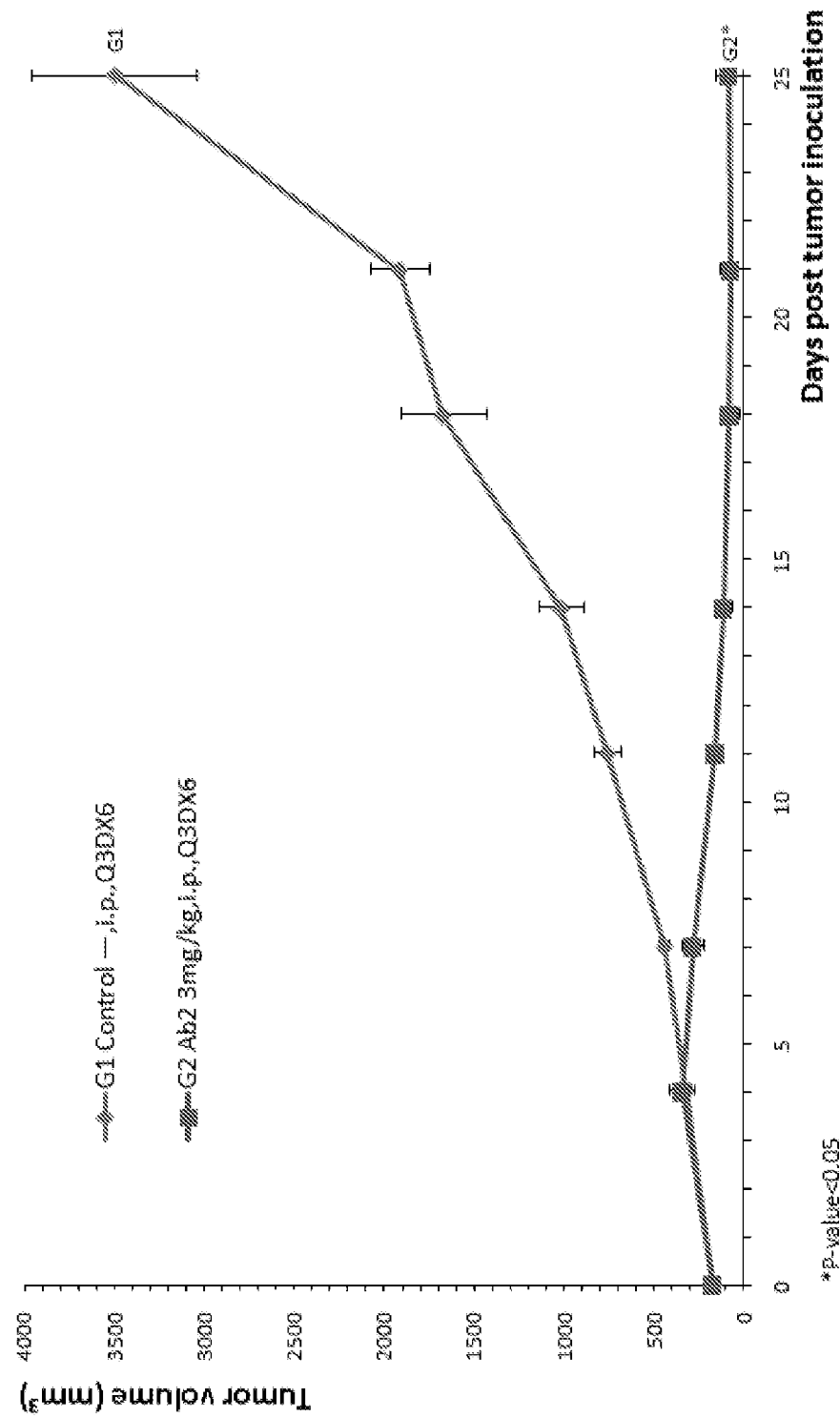
FIG. 16. Mouse colon cancer cells MC38 were injected into humanized CD137 homozygous mice. Antibody against human CD137 (AB-2) was administered to the mice (3 mg/kg). The average volumes of tumors in the G1 control group and the G2 treatment group are shown.

The tumor in the control group continued growing during the experimental period; when compared with the control group mice, the tumor volume in the treatment group was significantly smaller than the control group (FIG. 16). Particularly, 3 mice in the treatment group at the end of the experiment did not have tumors.

With respect to the tumor volume, in the control group (G1), the average tumor volume was 3501±458 mm³. The tumor volume in the treatment group was 84±76 mm³. Furthermore, $TGI_{TV}\%$ in the treatment group is 102.7%. The results indicated that Ab2 was effective for treating tumors in humanized CD137 homozygous mice.

In summary, the CD137 humanized mice can be used for screening human CD137 antibodies for treating tumors.

Example 9. Mice with Humanized CD137 and Humanized PD-1

Mice containing the humanized CD137 gene (e.g., animal model with humanized CD137 prepared using the methods as described in the present disclosure) can also be used to prepare an animal model with double-humanized or multi-humanized genes. For example, in Example 4, the embryonic stem cell used in the microinjection and embryo transfer process can be selected from the embryos of other genetically modified mice, so as to obtain double- or multiple-gene modified mouse models.

In addition, the humanized CD137 animal model homozygote or heterozygote can be mated with other genetically modified homozygous or heterozygous animal models, and the progeny is then screened; according to the Mendelian law, there is a chance to obtain the double-gene or multiple-gene modified heterozygous animal models, and then the obtained heterozygous can be mated with each other to finally obtain the double-gene or multiple-gene modified homozygotes.

In the case of the generating double humanized CD137/PD-1 mouse, since the mouse CD137 gene and PD-1 gene are located on different chromosomes, the double humanized CD137/PD-1 mouse was obtained by crossing the CD137 humanized mice with B-hPD-1 mice (mice with humanized PD-1 gene).

Figures 17A, 17B, 17C, 17D:
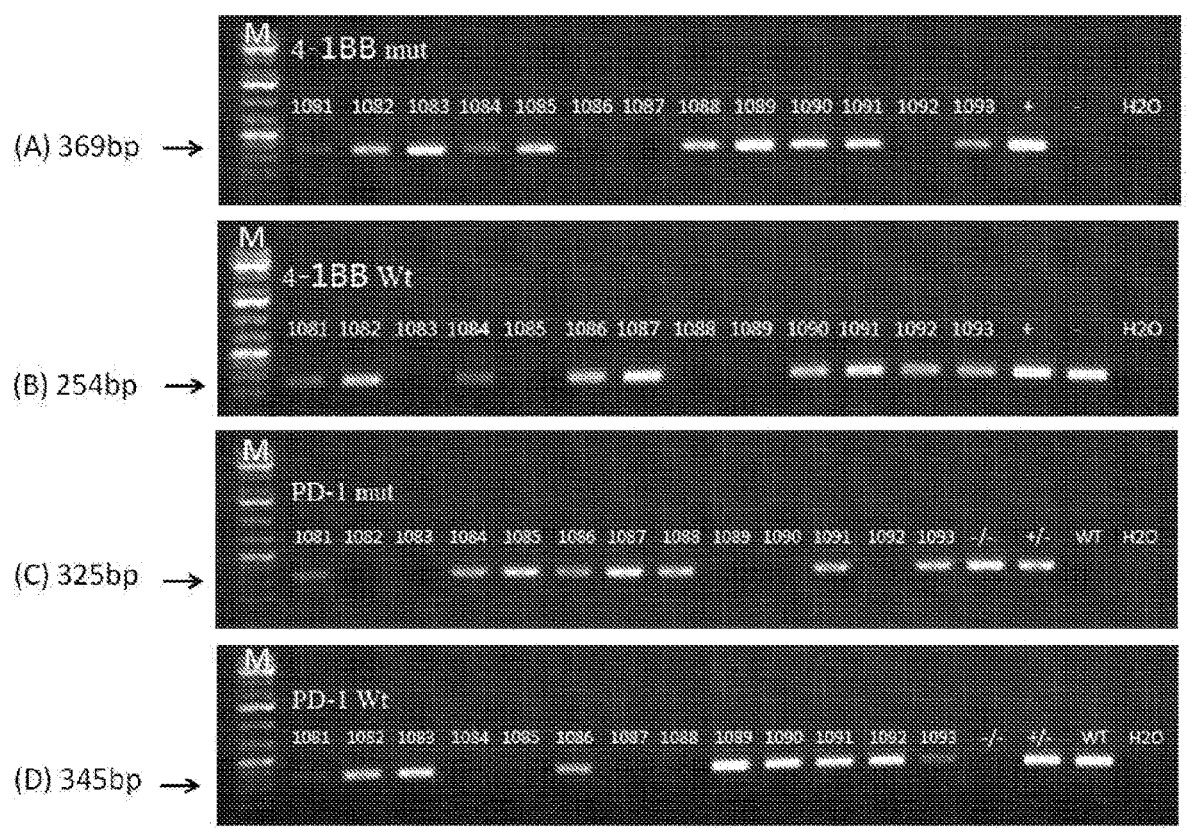
FIGS. 17A-17D are results from PCR.

PCR analysis was performed on the mouse tail genomic DNA of double humanized CD137/PD-1 mice using four pairs of primers. The specific sequences and product lengths are shown in the table below. The reaction system and reaction conditions are shown in Table 14 and Table 15. The results for a number of humanized CD137/PD-1 mice are shown in FIGS. 17A-17D, wherein FIGS. 17A and 17B show that the mice numbered 1083, 1085, 1088, 1089 were homozygous for humanized CD137. FIGS. 17C and 17D show that the mice numbered 1081, 1086, 1091, and 1093 were heterozygous for humanized PD-1, and the mice numbered 1084, 1085, 1087, and 1088 were homozygous for humanized PD-1. The combined results show that the mice numbered 1085 and 1088 were homozygous for both humanized CD137 and humanized PD-1 ($CD137^{H/H}/PD-1^{H/H}$), mice numbered 1081, 1091, and 1093 were heterozygous for both humanized CD137 and humanized PD-1 ($CD137^{H/+}/PD-1^{H/+}$), and mouse numbered 1084 was $CD137^{H/+}/PD-1^{H/H}$ mouse.

TABLE 13

Primer sequences

| Primer | Sequence | Product length |
|---|---|---|
| CD137 WT | F: 5'-gtttagcaagcatgctatcagtcaagc-3' (SEQ ID NO: 27)<br>R: 5'-ctgaactgagtcttcaacagtcatgtc-3' (SEQ ID NO: 28) | WT: 254 bp |
| CD137 MUT | F: 5'-gtttagcaagcatgctatcagtcaagc-3' (SEQ ID NO:27)<br>R: 5'-cacacagctaggttgtagcatcc-3' (SEQ ID NO: 29) | Mut: 369 bp |

TABLE 13-continued

Primer sequences

| Primer | Sequence | Product length |
|---|---|---|
| PD-1 MUT | F: 5'-cttccacatgagcgtggtcagggcc-3' (SEQ ID NO: 38)<br>R: 5'-ccaagggactattttagatgggcag-3' (SEQ ID NO: 39) | Mut: 325 bp |
| PD-1 WT | F: 5'-gaagctacaagctcctaggtaggggg-3' (SEQ ID NO: 40)<br>R: 5'-acgggttggctcaaaccattaca-3' (SEQ ID NO: 41) | WT: 345 bp |

TABLE 14

PCT reaction

| Composition | Volume |
|---|---|
| 2× Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| ddH$_2$O | Add to 20 μL |

TABLE 15

PCR amplification reaction condition

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

The expression of the double humanized CD137/PD-1 mice was further examined. A double humanized CD137/PD-1 homozygote (9 weeks old) was selected for the study. Two wildtype C57BL/6 mice were selected as controls. Mice were injected with 7.5 μg of mouse anti-CD3 antibody intraperitoneally. After 24 hours, the mice were euthanized, and then the spleens of the mice were collected. The obtained spleen cell samples were then analyzed by FACS and RT-PCR.

FACS: Expression of CD137 proteins in double humanized CD137/PD-1 mice was analyzed using the same methods as described above. The samples were stained with either 1) mouse anti-mCD137 antibody (m4-1BB APC) and anti-mTcRβ antibody (mTcRβ PerCP); or 2) anti-human CD137 antibody (h4-1BB PE) and anti-mTcRβ antibody (mTcRβ PerCP) for determining the expression of mouse or human CD137. The samples were also stained with either 1) mouse anti-mPD-1 antibody (mPD-1 PE) and anti-mTcRβ antibody (mTcRβ PerCP); or 2) anti-hPD-1 antibody (hPD-1 FITC) and anti-mTcRβ antibody (mTcRβ PerCP) for determining the expression of mouse or human PD-1. The stained samples were washed in PBS and analyzed by flow cytometry. Results are shown in FIGS. 18A-18F, and FIGS. 19A-19F.

Figures 18A, 18B, 18C, 18D, 18E, 18F:
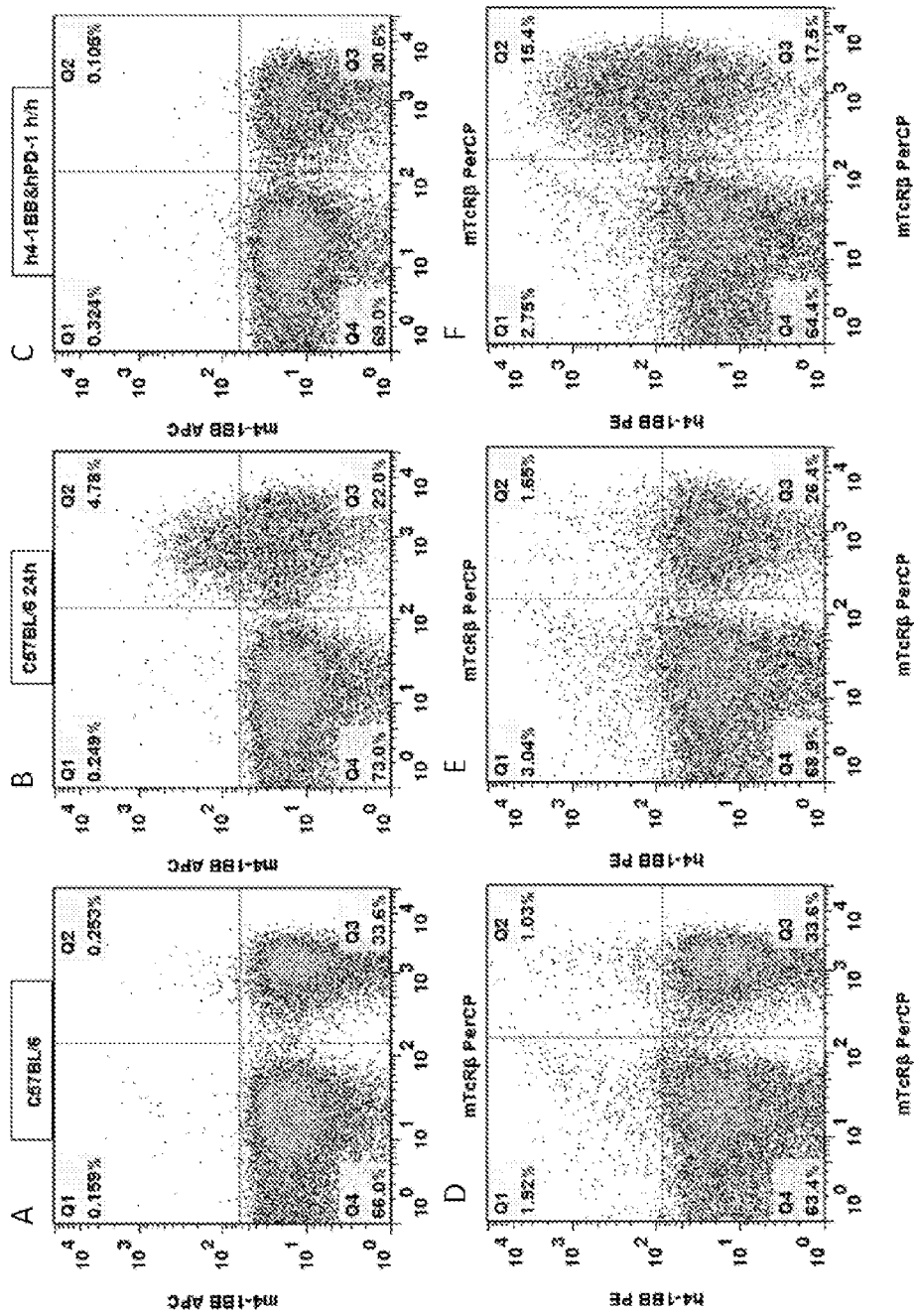
FIGS. 18A-18F are results of flow cytometry analysis.
Figures 19A, 19B, 19C, 19D, 19E, 19F:
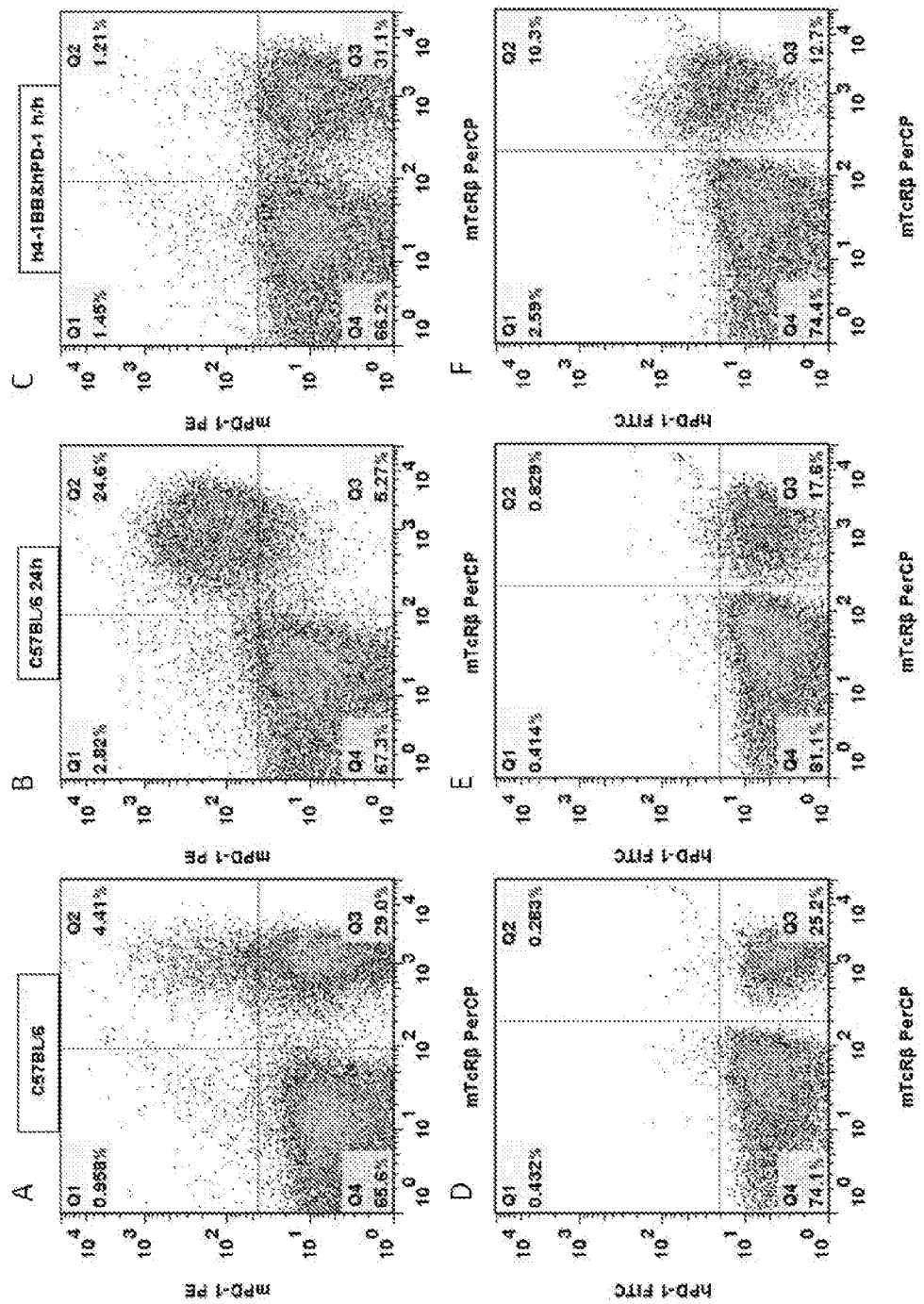
FIGS. 19A-19F are results of flow cytometry analysis.

Cells expressing humanized CD137 and humanized PD-1 proteins were detected in the spleens of double humanized CD137/PD-1 homozygotes (FIG. 18F and FIG. 19F). Humanized CD137 and humanized PD-1 were not detected in the spleens of C57BL/6 mice either with anti-CD3 antibody stimulation or without anti-CD3 antibody stimulation.

RT-PCR detection: Total RNA was extracted from the spleen cells of wildtype C57BL/6 mice and double humanized CD137/PD-1 homozygotes. cDNA was then obtained by reverse transcription using a reverse transcription kit.

m4-1BB RT-PCR F1: 5'-CCGTGCAGAACTCCTGT-GAT-3' (SEQ ID NO:42) and m4-1BB RT-PCR R1: 5'-GTTTTGCAACCCTGCTTCGT-3' (SEQ ID NO:43) were used to amplify a mouse CD137 fragment of 286 bp.

h4-1BB RT-PCR F1 (SEQ ID NO:36) and h4-1BB RT-PCR R1 (SEQ ID NO:37) were used amplify a humanized CD137 fragment of 155 bp.

mPD-1 RT-PCR F3: 5'-CCTGGCT-CACAGTGTCAGAG-3' (SEQ ID NO: 44) and mPD-1 RT-PCR R3: 5'-CAGGGCTCTCCTCGATTTTT-3' (SEQ ID NO: 45) were used to amplify a mouse PD-1 fragment of approximately 297 bp.

hPD-1 RT-PCR F3: 5'-CCCTGCTCGTGGTGACCGAA-3' (SEQ ID NO: 46) and hPD-1 RT-PCR R3: 5'-GCAGGCTCTCTTTGATCTGC-3' (SEQ ID NO: 47) were used to amplify a human PD-1 fragment of approximately 297 bp.

PCR reaction system was 20 reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 20:
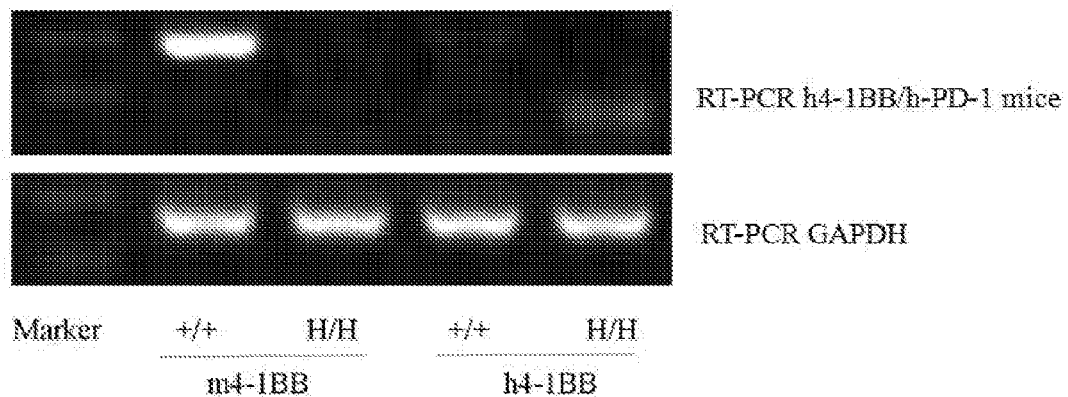
FIG. 20 shows results from RT-PCR for human CD137 (h4-1BB) and mouse CD137 (m4-1BB) mRNA. +/+ indicates wildtype C57BL/6 mice; H/H indicates mice that are homozygous for both humanized CD137 and humanized PD-1; and GAPDH was used as a control.
Figure 21:
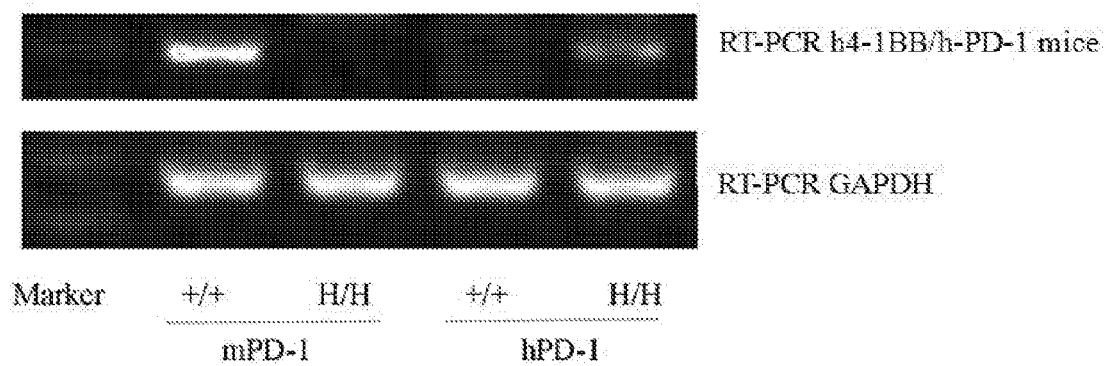
FIG. 21 shows results from RT-PCR for human PD-1 (hPD-1) and mouse PD-1 (mPD-1) mRNA. +/+ indicates wildtype C57BL/6 mice; H/H indicates mice that are homozygous for both humanized CD137 and humanized PD-1; and GAPDH was used as a control.

The results were shown in FIG. 20 and FIG. 21. The mRNA of mouse CD137 and mouse PD-1 were detected in the activated cells of wildtype C57BL/6 mice (+/+); while the mRNAs of humanized CD137 and humanized PD-1 were detected in the activated cells of double humanized CD137/PD-1 homozygotes (CD137$^{H/H}$/PD-1$^{H/H}$ or H/H as shown in FIG. 20 and FIG. 21).

Example 10. Mice with Humanized CD137 and Humanized PD-L1

As another example, double humanized CD137/PD-L1 mice were generated. Since the mouse CD137 gene and PD-L1 gene are located on different chromosomes, the double humanized CD137/PD-L1 mice were obtained by crossing humanized CD137 mice with humanized PD-L1 mice (e.g. B-hPD-L1, mice with humanized PD-L1 gene) by in vitro fertilization (IVF). The progeny were screened and further mated to eventually obtain double humanized CD137/PD-L1 mice.

Figures 22A, 22B, 22C, 22D:
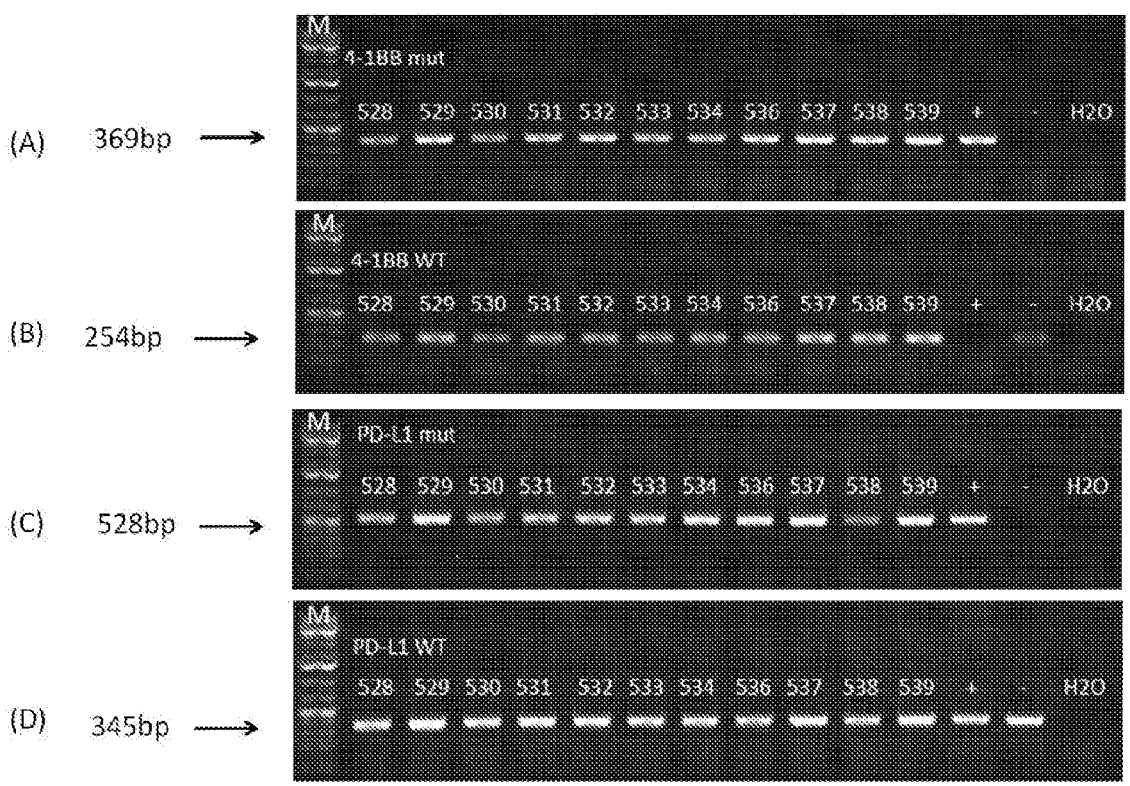
FIGS. 22A-22D show the result of PCR.

PCR analysis was performed on the mouse tail genomic DNA of double humanized CD137/PD-L1 mice using four pairs of primers. The specific sequences and product lengths are shown in Table 16. The reaction system and reaction conditions are shown in Table 14 and Table 15. The results for a number of humanized CD137/PD-L1 mice are shown in FIGS. 22A-22D, wherein FIGS. 22A and 22B show that the mice numbered 528-539 were heterozygous for humanized CD137. FIGS. 22C and 22D show that the mice numbered 528-539 were heterozygous for humanized PD-L1. The combined results show that the mice numbered 528-539 were all heterozygous for both humanized CD137 and humanized PD-L1 (CD137$^{H/+}$/PD-L1$^{H/+}$).

TABLE 16

Primer sequences

| Primer | Sequence | Product length |
|---|---|---|
| CD137 WT | F: 5'-gtttagcaagcatgctatcagtcaagc-3' (SEQ ID NO: 27)<br>R: 5'-ctgaactgagtcttcaacagtcatgtc-3' (SEQ ID NO: 28) | WT: 254 bp |
| CD137 MUT | F: 5'-gtttagcaagcatgctatcagtcaagc-3' (SEQ ID NO: 27)<br>R: 5'-cacacagctaggttgtagcatcc-3' (SEQ ID NO: 29) | Mut: 369 bp |
| PD-L1 MUT | 5'-ccagggaggtggcccactgataata-3' (SEQ ID NO: 48)<br>5'-cacccctgcatcctgcaatttcaca-3' (SEQ ID NO: 49) | Mut: 528 bp |
| PD-L1 WT | 5'-ccagggaggtggcccactgataata-3' (SEQ ID NO: 48)<br>5'-actaacgcaagcaggtccagctccc-3' (SEQ ID NO: 50) | WT: 345 bp |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises at least one chromosome comprising, at an endogenous CD137 gene locus, a replacement of a nucleic acid sequence encoding a portion of the extracellular region of an endogenous CD137 protein with a nucleic acid sequence encoding a portion of the extracellular region of a human CD137 protein, wherein the mouse detectably expresses a chimeric CD137 protein comprising a humanized CD137 extracellular region and an endogenous CD137 cytoplasmic region on the surface of activated T cells, wherein the sequence encoding the chimeric CD137 protein is operably linked to an endogenous regulatory element at the endogenous CD137 gene locus in the at least one chromosome, wherein the expressed chimeric CD137 protein can be recognized by an anti-human CD137 antibody, and wherein the anti-human CD137 antibody can increase immune response in the mouse, wherein the chimeric CD137 protein comprises SEQ ID NO: 24.

2. The mouse of claim 1, wherein the mouse does not express endogenous CD137.

3. The mouse of claim 1, wherein the mouse further comprises a sequence encoding an additional human or chimeric protein.

4. The mouse of claim 3, wherein the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (OX40).

5. The genetically-modified, mouse of claim 1, wherein the mouse has a tumor, and the anti-human CD137 antibody inhibits tumor growth in the mammal.

6. A method of determining effectiveness of an anti-CD137 antibody for treating cancer, comprising:
   administering the anti-CD137 antibody to the mouse of claim 1, wherein the mouse has a tumor; and
   determining inhibitory effects of the anti-CD137 antibody to the tumor.

7. The method of claim 6, wherein the tumor comprises one or more human tumor cells that are injected into the mouse.

8. A genetically-modified, non-human mammal that is made by a method comprising:
   (1) providing a plasmid comprising a human CD137 gene fragment, flanked by a 5' homology arm and a 3' homology arm, wherein the 5' and 3' homology arms target the endogenous CD137 gene, wherein the human CD137 gene fragment comprises SEQ ID NO: 21;
   (2) modifying the genome of a fertilized egg or an embryonic stem cell by contacting the genome of the fertilized egg or the embryonic stem cell with the plasmid of step (1);
   (3) transplanting the fertilized egg obtained in step (2) into the oviduct of a pseudo-pregnant female non-human mammal or transplanting the embryonic stem cell obtained in step (2) into a blastocyst, which is then transplanted into the oviduct of a pseudo-pregnant female non-human to produce a genetically-modified non-human that functionally expresses a chimeric CD137 protein comprising a humanized CD137 extracellular region and an endogenous CD137 cytoplasmic region on the surface of activated T cells, wherein the sequence encoding the chimeric CD137 protein is operably linked to an endogenous regulatory element at the endogenous CD137 gene locus; and (4) mating the mammal obtained in step (3) to obtain a homozygote.

9. The genetically-modified, non-human mammal of claim 8, wherein the 5' homology arm comprises SEQ ID NO: 19.

10. The genetically-modified, non-human mammal of claim 8, wherein the 3' homology arm comprises SEQ ID NO: 20.

11. The genetically-modified, non-human mammal of claim 8, wherein the mammal is a mouse.

\* \* \* \* \*

UNITED STATES PATENT AND TRADEMARK OFFICE
CERTIFICATE OF CORRECTION

PATENT NO. : 11,154,040 B2
APPLICATION NO. : 16/434456
DATED : October 26, 2021
INVENTOR(S) : Yuelei Shen et al.

It is certified that error appears in the above-identified patent and that said Letters Patent is hereby corrected as shown below:

On the Title Page

In Column 1 Item (30) (Foreign Application Priority Data), Line 3, delete "20171147325.1" and insert -- 201711473251.1 --, therefor.

In Column 2 Item (56) (Other Publications), Line 19, delete "Testing" and insert -- Festing --, therefor.

In the Claims

In Column 96, Line 42, In Claim 4, delete "(0X40)." and insert -- (OX40). --, therefor.

In Column 97, Line 4, In Claim 8, after "non-human" insert -- mammal --.

In Column 97, Line 5, In Claim 8, after "non-human" insert -- mammal --.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*